United States Patent
Ahmar et al.

(10) Patent No.: US 12,084,407 B2
(45) Date of Patent: Sep. 10, 2024

(54) CANNABIGEROL DERIVATIVES AND USE THEREOF AS CANNABINOID RECEPTOR MODULATORS

(71) Applicant: CANOPY GROWTH CORPORATION, Smiths Falls (CA)

(72) Inventors: Siawash Ahmar, Toronto (CA); Krishna Kumar Gnanasekaran, Mississauga (CA); Jeffrey Alan Omeara, Halton Hills (CA)

(73) Assignee: CANOPY GROWTH CORPORATION, Smith Falls (CA)

( * ) Notice: Subject to any disclaimer, the term of this patent is extended or adjusted under 35 U.S.C. 154(b) by 0 days.

(21) Appl. No.: 17/780,047

(22) PCT Filed: Nov. 25, 2020

(86) PCT No.: PCT/CA2020/051607
§ 371 (c)(1),
(2) Date: May 26, 2022

(87) PCT Pub. No.: WO2021/102567
PCT Pub. Date: Jun. 3, 2021

(65) Prior Publication Data
US 2023/0150927 A1    May 18, 2023

Related U.S. Application Data

(60) Provisional application No. 62/940,545, filed on Nov. 26, 2019, provisional application No. 63/110,479, filed on Nov. 6, 2020.

(51) Int. Cl.
| | |
|---|---|
| C07C 311/29 | (2006.01) |
| A61P 3/00 | (2006.01) |
| C07C 309/75 | (2006.01) |
| C07C 311/51 | (2006.01) |
| C07C 317/22 | (2006.01) |
| C07D 205/06 | (2006.01) |
| C07D 205/12 | (2006.01) |
| C07D 207/408 | (2006.01) |
| C07D 211/54 | (2006.01) |
| C07D 213/71 | (2006.01) |
| C07D 233/84 | (2006.01) |
| C07D 235/16 | (2006.01) |
| C07D 235/28 | (2006.01) |
| C07D 239/40 | (2006.01) |
| C07D 249/08 | (2006.01) |
| C07D 249/10 | (2006.01) |
| C07D 263/32 | (2006.01) |
| C07D 277/30 | (2006.01) |
| C07D 295/15 | (2006.01) |
| C07D 295/26 | (2006.01) |
| C07D 305/08 | (2006.01) |
| C07D 307/64 | (2006.01) |
| C07D 487/10 | (2006.01) |

(52) U.S. Cl.
CPC ............. *C07C 311/29* (2013.01); *A61P 3/00* (2018.01); *C07C 309/75* (2013.01); *C07C 311/51* (2013.01); *C07C 317/22* (2013.01); *C07D 205/06* (2013.01); *C07D 205/12* (2013.01); *C07D 207/408* (2013.01); *C07D 211/54* (2013.01); *C07D 213/71* (2013.01); *C07D 233/84* (2013.01); *C07D 235/16* (2013.01); *C07D 235/28* (2013.01); *C07D 239/40* (2013.01); *C07D 249/08* (2013.01); *C07D 249/10* (2013.01); *C07D 263/32* (2013.01); *C07D 277/30* (2013.01); *C07D 295/15* (2013.01); *C07D 295/26* (2013.01); *C07D 305/08* (2013.01); *C07D 307/64* (2013.01); *C07D 487/10* (2013.01); *C07C 2601/02* (2017.05); *C07C 2601/04* (2017.05); *C07C 2601/14* (2017.05)

(58) Field of Classification Search
None
See application file for complete search history.

(56) References Cited

U.S. PATENT DOCUMENTS

| | | |
|---|---|---|
| 2022/0242844 A1 | 8/2022 | Omeara et al. |
| 2022/0242856 A1 | 8/2022 | Ahmar et al. |
| 2022/0259221 A1 | 8/2022 | Omeara et al. |
| 2022/0259233 A1 | 8/2022 | Omeara et al. |
| 2022/0267239 A1 | 8/2022 | Omeara et al. |
| 2022/0324806 A1 | 10/2022 | Ahmar et al. |
| 2022/0340582 A1 | 10/2022 | Ahmar et al. |
| 2022/0348586 A1 | 11/2022 | Ahmar et al. |
| 2023/0024212 A1 | 1/2023 | Gunning et al. |
| 2023/0059582 A1 | 2/2023 | Omeara et al. |
| 2023/0122510 A1 | 4/2023 | Ahmar et al. |
| 2023/0134776 A1 | 5/2023 | Ahmar et al. |
| 2023/0286906 A1 | 9/2023 | Ahmar et al. |

FOREIGN PATENT DOCUMENTS

| | | |
|---|---|---|
| WO | WO 2007/144628 | 12/2007 |
| WO | WO 2015/128200 | 9/2015 |

OTHER PUBLICATIONS

Grant & Hackh's Chemical Dictionary (5th Ed. 1987) at p. 148.*
Written Opinion in International Application No. PCT/CA2020/051607, Feb. 18, 2021, pp. 1-7.

* cited by examiner

*Primary Examiner* — Po-Chih Chen
(74) *Attorney, Agent, or Firm* — SALIWANCHIK, LLOYD & EISENSCHENK

(57) ABSTRACT

The synthesis of a range of pentylbezene-1,3-diol compounds of formula I is disclosed. These compounds bind to cannabinoid 1 and 2 receptors (CB1 and CB2), and are thus presumed to be useful in modulating the activity of such receptors. Accordingly, the use of such synthetic cannabinoids in the treatment of various disorders mediated by CB1 and CB2 is contemplated.

17 Claims, No Drawings

CANNABIGEROL DERIVATIVES AND USE THEREOF AS CANNABINOID RECEPTOR MODULATORS

BACKGROUND OF THE DISCLOSURE

Cross-Reference to Related Applications

This application is the U.S. National Stage Application of International Patent Application No. PCT/CA2020/051607, filed on Nov. 25, 2020, which claims priority to and benefit of U.S. Provisional Patent Application Ser. No. 62/940,545 filed on Nov. 26, 2019 and U.S. Provisional Patent Application Ser. No. 63/110,479 filed on Nov. 6, 2020, each of which is hereby incorporated by reference in its entirety.

FIELD OF THE DISCLOSURE

This disclosure relates generally to cannabinoid derivatives, pharmaceutical compositions comprising them, and methods of using the cannabinoid derivatives.

TECHNICAL BACKGROUND

Every individual has an endocannabinoid system comprised of chemical receptors in the brain, immune system, and central nervous system, for example including the cannabinoid 1 (CB1) receptor and cannabinoid 2 (CB2) receptor. The endocannabinoid system regulates many important physiological processes and several components of the endocannabinoid system, such as receptors, transporters, endocannabinoids and enzymes involved in the synthesis and degradation of endocannabinoids, are under active investigation as targets to treat a diverse array of indications.

CB1 and CB2 receptors are a class of cell membrane receptors belonging to the G protein-coupled receptor (GPCR) superfamily. The CB1 and CB2 receptors are distinguished from each other by their amino acid sequence, tissue distribution, signaling mechanisms, and ability to bind sub-type specific ligands. The CB1 receptor is mainly expressed in the central nervous system (CNS), lungs, liver, adipose tissue, and kidneys, and the CB2 receptor is mainly localized in immune cells (e.g. macrophages and T-cells), on cells that are involved in bone formation and bone loss, and in the gastrointestinal system. These receptors have been associated with many human diseases including obesity, diabetes, fibrosis, liver diseases, cardiovascular disease, cancer, pain, inflammation, MS spasticity, and glaucoma, among others.

Cannabinoids are compounds active on cannabinoid receptors in humans and have been implicated in many of the pharmacological benefits on the diseases noted above. Cannabinoids of plant origin, also known as phytocannabinoids, are abundant in *Cannabis*. Medical use of cannabis and associated phytocannabinoids is becoming widely accepted in many countries, including the United States, as an alternative form of medicine. Many states have legalized its use for qualified medical conditions such as chronic pain, epilepsy, sleep disorders, anxiety, cancer, glaucoma, nausea, amyotrophic lateral sclerosis (ALS), Alzheimer's disease, Crohn's disease, Post-traumatic Stress Disorder (PTSD), arthritis, fibromyalgia, and others.

In addition to the CB1 and CB2 receptors, other receptors have also been implicated in modulating the activity of cannabinoids in the human and/or animal body. For example, the serotonin receptors, such as 5HT1A and 5HT2A, are likewise GPCRs that have been identified as cannabinoid targets. The serotonin receptors modulate the release of many neurotransmitters, including glutamate, GABA, dopamine, epinephrine/norepinephrine and acetylcholine, as well as many hormones. Like the CB1 and CB2 receptors, the serotonin receptors influence various biological and neurological processes, such as anxiety, appetite, cognition, and mood, among others. Other receptors identified as being influenced by cannabinoid or cannabinoid-like compounds include GPR18, GPR55, GPR119, TRPV1, TRPV2, PPARs (e.g. PPARγ), and the μ-opioid receptors. Indeed, binding of these receptors may be responsible for off-target effects of cannabinoids.

One of the most common ways that cannabinoids are used for medicinal use in many countries is through smoking of *cannabis*. Although proven to be beneficial in certain indications, smoking medical *cannabis* has disadvantages. For example, the smoke from the plant matter comprises carcinogens and other toxins in addition to the desired cannabinoids. Heavy *cannabis* use through smoking has also been associated with accelerated pulmonary decline, lung damage, and emphysema. Another disadvantage of smoking medical *cannabis* is difficulty in maintaining control over the proper dosing of medicinal *cannabis* due to active ingredients fluctuations (e.g., the amounts of active ingredients may differ depending on the differences present in plant varietals as well as changing growing conditions which result in intravarietal variations). Finally, consumption through smoking has a relatively low bioavailability of target compounds compared to other delivery methods.

A less common way to utilize *cannabis* for medical use is to extract beneficial cannabinoids from *cannabis*. Many extraction processes have been developed for isolating and purifying natural cannabinoids. But there has been difficulty in isolating individual cannabinoids at high levels of purity, both for active ingredients for use in medicine and product manufacturing and/or as standards for use in research and development.

Therefore, there exists a need for novel ligands of cannabinoid receptors that have the potential for therapeutic benefit.

SUMMARY OF THE DISCLOSURE

One aspect of the present disclosure relates to compounds of formula (I):

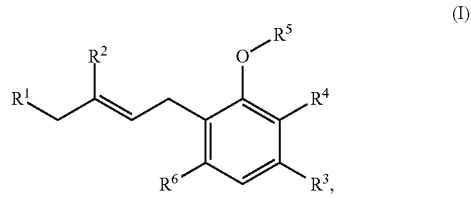

or an enantiomer, diastereomer, racemate, tautomer, or metabolite thereof, or of a pharmaceutically acceptable salt, a solvate or hydrate of the compound, enantiomer, diastereomer, racemate, tautomer, or metabolite, wherein $R^1$ is hydrogen, halo, $C_1$-$C_8$ alkyl, $C_2$-$C_8$ alkenyl, $C_2$-$C_8$ alkynyl, —$CO_2H$, —($C_0$-$C_4$ alkyl)-C(O)O($C_1$-$C_6$ alkyl), —($C_0$-$C_4$ alkyl)-OC(O)O—($C_1$-$C_6$ alkyl), —($C_0$-$C_4$ alkyl)-N($R^{1b}$)—C(O)—O—($C_1$-$C_6$ alkyl), —($C_0$-$C_4$ alkyl)-O—C(O)—N$R^{1b}R^{1c}$, —($C_0$-$C_4$ alkyl)-N($R^{1b}$)—C(O)—N$R^{1b}R^{1c}$, —$OR^{1a}$, —($C_1$-$C_4$ alkyl)$OR^{1a}$, —$SR^{1a}$, —($C_1$-$C_4$ alkyl)S(O)$_{0\text{-}2}R^{1a}$, —NR$^{1b}$R$^{1c}$, —(C$_1$-C$_4$ alkyl)NR$^{1b}$R$^{1c}$, —(C$_1$-C$_4$ alkyl)C(O)NR$^{1b}$R$^{1c}$, —(C$_0$-C$_4$ alkyl)-aryl, —(C$_0$-C$_4$ alkyl)-heteroaryl, —(C$_0$-C$_4$ alkyl)-cycloalkyl, or —(C$_0$-C$_4$ alkyl)-heterocycloalkyl, wherein R$^{1a}$, R$^{1b}$, and R$^{1c}$ are independently hydrogen, C$_1$-C$_4$ alkyl, or —C(O)(C$_1$-C$_4$) alkyl; R$^2$ is hydrogen, halo, C$_1$-C$_8$ alkyl, C$_2$-C$_8$ alkenyl, C$_2$-C$_8$ alkynyl, —CO$_2$H, —(C$_0$-C$_4$ alkyl)-C(O)O(C$_1$-C$_6$ alkyl), —(C$_0$-C$_4$ alkyl)-OC(O)O—(C$_1$-C$_6$ alkyl), —(C$_1$-C$_4$ alkyl)OR$^{2a}$, —(C$_1$-C$_4$ alkyl)SR$^{2a}$, —NR$^{2b}$R$^{2c}$, —(C$_1$-C$_4$ alkyl)NR$^{2b}$R$^{2c}$, —(C$_1$-C$_4$ alkyl)C(O)NR$^{2b}$R$^{2c}$, —(C$_0$-C$_4$ alkyl)-aryl, —(C$_0$-C$_4$ alkyl)-heteroaryl, —(C$_0$-C$_4$ alkyl)-cycloalkyl, or —(C$_0$-C$_4$ alkyl)-heterocycloalkyl, wherein R$^{2a}$, R$^{2b}$, and R$^{2c}$ are independently hydrogen, C$_1$-C$_4$ alkyl, or —C(O)(C$_1$-C$_4$) alkyl;

R$^3$ is hydrogen, C$_1$-C$_{12}$ alkyl, C$_2$-C$_{12}$ alkenyl, C$_2$-C$_{12}$ alkynyl, —(OCH$_2$CH$_2$)$_{0-6}$O(C$_1$-C$_8$ alkyl), —(C$_0$-C$_4$ alkyl)-NR$^{3a}$R$^{3b}$, —(C$_0$-C$_4$ alkyl)-aryl, —(C$_0$-C$_4$ alkyl)-heteroaryl, —(C$_0$-C$_4$ alkyl)-cycloalkyl or —(C$_0$-C$_4$ alkyl)-heterocycloalkyl, wherein R$^{3a}$ and R$^{3b}$ are each independently hydrogen or C$_1$-C$_6$ alkyl;

R$^4$ is

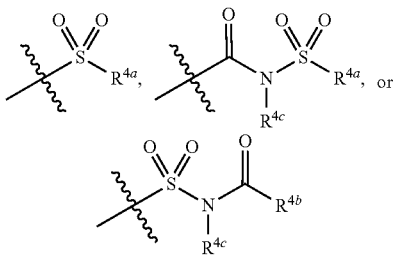

wherein

R$^{4a}$ is C$_1$-C$_8$ alkyl, C$_2$-C$_8$ alkenyl, C$_2$-C$_8$ alkynyl, —OR$^{4e}$, —(C$_1$-C$_4$ alkyl)OR$^{4e}$, —(C$_1$-C$_4$ alkyl)-C(O)(C$_1$-C$_4$ alkyl), —(C$_0$-C$_4$ alkyl)-aryl, —(C$_0$-C$_4$ alkyl)-heteroaryl, —(C$_0$-C$_4$ alkyl)-cycloalkyl, —(C$_0$-C$_4$ alkyl)-heterocycloalkyl, —NR$^{4d}$R$^{4e}$, or —(C$_1$-C$_4$ alkyl)NR$^{4d}$R$^{4e}$, and R$^{4b}$ is C$_1$-C$_8$ alkyl, C$_2$-C$_8$ alkenyl, C$_2$-C$_8$ alkynyl, —CH$_2$—(OCH$_2$CH$_2$)$_{0-6}$O(C$_1$-C$_8$ alkyl), —(C$_1$-C$_4$ alkyl)OR$^{4e}$, —(C$_1$-C$_4$ alkyl)-C(O)(C$_1$-C$_4$ alkyl), —(C$_1$-C$_4$ alkyl)-C(O)O(R$^{4e}$), —(C$_0$-C$_4$ alkyl)-aryl, —(C$_0$-C$_4$ alkyl)-heteroaryl, —(C$_0$-C$_4$ alkyl)-cycloalkyl, —(C$_0$-C$_4$ alkyl)-heterocycloalkyl, or —(C$_1$-C$_4$ alkyl)NR$^{4d}$R$^{4e}$, wherein R$^{4d}$ is hydrogen, C$_1$-C$_6$ alkyl, C$_2$-C$_6$ alkenyl, —(C$_1$-C$_4$ alkyl)-C(O)(C$_1$-C$_4$ alkyl), —(C$_1$-C$_4$ alkyl)-C(O)O(R$^{4e}$), —(C$_1$-C$_4$ alkyl)-OC(O)(R$^{4e}$), —(C$_0$-C$_4$ alkyl)-aryl, —(C$_0$-C$_4$ alkyl)-heteroaryl, —(C$_0$-C$_4$ alkyl)-cycloalkyl, or —(C$_0$-C$_4$ alkyl)-heterocycloalkyl, R$^{4e}$ is hydrogen, C$_1$-C$_4$ alkyl, or aryl, and R$^{4c}$ is hydrogen or C$_1$-C$_4$ alkyl;

R$^5$ is hydrogen, C$_1$-C$_8$ alkyl, —(C$_1$-C$_4$ alkyl)-O—(C$_1$-C$_4$ alkyl), —C(O)(C$_1$-C$_4$ alkyl), —C(O)O(C$_1$-C$_4$ alkyl), —C(O)NH$_2$, —C(O)NH(C$_1$-C$_4$ alkyl), —C(O)N(C$_1$-C$_4$ alkyl)$_2$, —(C$_1$-C$_4$ alkyl)C(O)O(C$_1$-C$_4$ alkyl), or —(C$_1$-C$_4$ alkyl)OC(O)(C$_1$-C$_4$ alkyl); and R$^6$ is hydrogen or —OR$^{6a}$, wherein R$^{6a}$ is hydrogen, C$_1$—C alkyl, —(C$_1$-C$_4$ alkyl)-O—(C$_1$-C$_4$ alkyl), —C(O)(C$_1$-C$_4$ alkyl), —C(O)O(C$_1$-C$_4$ alkyl), —C(O)NH$_2$, —C(O)NH(C$_1$-C$_4$ alkyl), —C(O)N(C$_1$-C$_4$ alkyl)$_2$, —(C$_1$-C$_4$ alkyl)C(O)O(C$_1$-C$_4$ alkyl), or —(C$_1$-C$_4$ alkyl)OC(O)(C$_1$-C$_4$ alkyl);

wherein each alkyl, alkenyl and alkynyl is unsubstituted, halogenated (e.g., fluorinated, chlorinated), substituted with one or two hydroxyl or C$_1$-C$_6$ alkoxy groups, or substituted with one or two oxo groups;

each cycloalkyl has 3-10 ring carbons and is saturated or partially unsaturated, and optionally includes one or two fused cycloalkyl rings, each fused ring having 3-8 ring members, and is substituted with 0-6 R$^7$;

each heterocycloalkyl has 3-10 ring members and 1-3 heteroatoms where each is independently nitrogen, oxygen or sulfur and is saturated or partially unsaturated, and optionally includes one or two fused cycloalkyl rings, each having 3-8 ring members, and is substituted with 0-6 R$^7$;

each aryl is a phenyl or a naphthyl, and optionally includes one or two fused cycloalkyl or heterocycloalkyl rings, each fused cycloalkyl or heterocycloalkyl ring having 4-8 ring members, and is substituted with 0-5 R$^8$;

each heteroaryl is a 5-6 membered monocyclic heteroaryl ring having 1-4 heteroatoms, where each is independently nitrogen, oxygen or sulfur or a 8-10 membered bicyclic heteroaryl having 1-5 heteroatoms where each is independently nitrogen, oxygen or sulfur, and optionally includes one or two fused cycloalkyl or heterocycloalkyl rings, each fused cycloalkyl or heterocycloalkyl ring having 4-8 ring members, and is substituted with 0-5 R$^8$, in which each R$^7$ is independently oxo, C$_1$-C$_4$ alkyl, —C$_1$, —F, —Br, —CN, —SF$_5$, —N$_3$, nitro, —SR$^A$, —S(O)$_{1-2}$R$^A$, OR$^A$, —(C$_0$-C$_3$ alkyl)-OR$^B$, —NR$^B$R$^A$, —C(O)R$^A$, —C(O)NR$^B$R$^A$, —NR$^B$C(O)R$^A$, —C(S)NR$^B$R$^A$, —NR$^B$C(S)R$^A$, —O$_2$R$^A$, —OC(O)R$^A$, C(O)SR A, —SC(O)R$^A$, —C(S)OR$^A$, —OC(S)R$^A$, C(S)SR A, —S(S)R$^A$, —S(O)$_{1-2}$OR$^A$, —OS(O)$_{1-2}$R$^A$, S(O)$_{1-2}$NR$^B$R$^A$, —NR$^B$S(O)$_2$R$^A$, —OCO$_2$R$^A$, —OC(O)NR$^B$R$^A$, —NR$^B$CO$_2$R$^A$, —NR$^B$C(O)NR$^B$R$^A$, —SCO$_2$R$^A$, —OC(O)SR$^A$, —SC(O)SR$^A$, —SC(O)NR$^B$R$^A$, —NR$^B$C(S)OR$^A$, —OC(S)OR$^A$, —OC(S)NR$^B$R$^A$, —NR$^B$C(S)OR$^A$, —NR$^B$C(S)NR$^B$R$^A$, —SC(S)OR$^A$, —OC(S)SR$^A$, —SC(S)SR$^A$, —SC(S)NR$^B$R$^A$, —NR$^B$C(S)SR$^A$, —NR$^B$C(NR$^B$)NR$^B$R$^A$, —NR$^B$S(O)$_{1-2}$NR$^B$R$^A$, phenyl, C$_3$-C$_8$ cycloalkyl, a five to six-membered heteroaryl, or a five to six-membered heterocycloalkyl; and each R$^8$ is independently optionally-substituted C$_1$-C$_4$ alkyl, —C$_1$, —F, —Br, —CN, —SF$_5$, —N$_3$, nitro, —SR$^A$, —S(O)$_{1-2}$R$^A$, —OR$^A$, —(C$_0$-C$_3$ alkyl)-OR$^B$, —NR$^B$R$^A$, —C(O)R$^A$, —C(O)NR$^B$R$^A$, —NR$^B$C(O)R$^A$, —C(S)NR$^B$R$^A$, —NR$^B$C(S)R$^A$, —O$_2$R$^A$, —OC(O)R$^A$, —SO$_3$H, —C(O)SR$^A$, —SC(O)R$^A$, —C(S)OR$^A$, —OC(S)R$^A$, —A(S)SR$^A$, —SC(S)R$^A$, —S(O)$_{1-2}$OR$^A$, OS(O)$_{1-2}$R$^A$, —S(O)$_{1-2}$NR$^B$R$^A$, —NR$^B$S(O)$_{1-2}$R$^A$, OCO$_2$R$^A$, —OC(O)NR$^B$R$^A$, —NR$^B$CO$_2$R$^A$, —NR$^B$C(O)NR$^B$R$^A$, —O$_2$R$^A$, —OC(O)SR$^A$, —SC(O)SR$^A$, —SC(O)NR$^B$R$^A$, —NR$^B$C(O)SR$^A$, —OC(S)OR$^A$, —OC(S)NR$^B$R$^A$, —NR$^B$C(S)OR$^A$, —NR$^B$C(S)NR$^B$R$^A$, AS_(S)OR$^A$, —OC(S)SR$^A$, AS(S)SR$^A$, —SC(S)NR$^B$R$^A$, —NR$^B$C(S)SR$^A$, —NR$^B$C(NR$^B$)NR$^B$R$^A$, —NR$^B$S(O)$_{1-2}$NR$^B$R$^A$; phenyl, C$_3$-C$_8$ cycloalkyl, a five to six-membered heteroaryl, or a five to six-membered heterocycloalkyl;

wherein each $R^A$ is independently H or $C_1$-$C_3$ alkyl, and each $R^B$ is independently H, $C_1$-$C_3$ alkyl, $C_1$-$C_3$ fluoroalkyl, $C_1$-$C_3$ hydroxyalkyl, —S(O)$_{1\text{-}2}$($C_1$-$C_3$ alkyl), —C(O)($C_1$-$C_3$ alkyl) or —CO$_2$($C_1$-$C_3$ alkyl), or $R^A$ and $R^B$ together with the nitrogen atom to which they are attached come together to form an unsubstituted heterocycloalkyl ring comprised of 3-6 ring members.

In another aspect, the present disclosure relates to pharmaceutical compositions comprising a compound (e.g., a compound of formula (I)) as described herein, or an enantiomer, diastereomer, racemate, tautomer, or metabolite thereof, or a pharmaceutically acceptable salt, solvate or hydrate of the compound, enantiomer, diastereomer, racemate, tautomer, or metabolite. In an embodiment, the pharmaceutical compositions comprise a pharmaceutically acceptable excipient, diluent, or carrier.

In another aspect, the present disclosure relates to a method for treating or preventing a disease, such as a disease associated with a cannabinoid 1 receptor (e.g. CB1, CB2, 5HT1A, 5HT2A, GPR18, GPR55, GPR119, TRPV1, TRPV2, PPARγ, or a μ-opioid receptor), in a subject in need thereof. In an embodiment, the method includes administering to the subject a therapeutically effective amount of a compound as described herein, or an enantiomer, diastereomer, racemate, tautomer, or metabolite thereof, or a pharmaceutically acceptable salt, solvate or hydrate of the compound, enantiomer, diastereomer, racemate, tautomer, or metabolite. In an embodiment, the method includes administering to the subject a pharmaceutical composition as described herein.

In certain embodiments, the diseases that may be treated or prevented with the compounds or compositions as described herein include, but are not limited to attention-deficit/hyperactivity disorder (ADHD)/attention-deficit disorder (ADD), alcohol use disorder, allergic asthma, amyotrophic lateral sclerosis (ALS), Alzheimer's, anorexia (e.g. human immunodeficiency virus (HIV)-related cachexia), anxiety disorders (e.g., social anxiety disorder, specific phobia, test anxiety, generalized anxiety disorder), arthritis, atherosclerosis, autism, bipolar disorder, burns, cancer, cancer pain, Charcot-Marie-Tooth disease, chronic inflammatory demyelinating polyneuropathies, chronic allograft nephropathy, cocaine use disorder, complex regional pain syndrome, congestive heart failure, depression, fibromyalgia, fragile X syndrome/fragile X-associated tremor and ataxia syndrome (FXTAS), frontotemporal dementias (behavioural variant), gingivitis pyrexia, glaucoma, glioblastoma, glomerulonephropathy, Huntington's disease, hypertrophic scars, inflammatory bowel disease (IBD)/irritable bowel syndrome (IBS), inflammation, Inflammatory myopathies, ischemia, kidney fibrosis, keloids, leukodystrophies, liver fibrosis, liver cirrhosis, lung fibrosis, migraine, multiple sclerosis, myocardial infarction, nausea (e.g. chemotherapy-induced nausea and vomiting (CINV), motion sickness), neuropathic pain (e.g., postherpetic neuralgia, painful diabetic neuropathy), nightmare disorder, non-alcoholic fatty liver disease, obesity, obsessive-compulsive disorder, opioid sparing, opioid use disorder, osteoarthritis, osteoporosis, pain (e.g. acute or chronic pain), Parkinson's, post-concussion syndrome/traumatic brain injury, psychosis/schizophrenia, posttraumatic stress disorder (PTSD), regulation of bone mass, rapid eye movement (REM) sleep behaviour disorder, reperfusion injury, Rett syndrome, rheumatoid arthritis, skin conditions (e.g. acne, psoriatic arthritis), sleep disorders (e.g., insomnia, restless legs syndrome (RLS)), spinocerebellar ataxias, systemic fibrosis, systemic sclerosis, thermal injury, tobacco use disorder/nicotine dependence, Tourette's, tumors, and trigeminal neuralgia.

In another aspect, the present disclosure relates to use of a compound as described herein, or an enantiomer, diastereomer, racemate, tautomer, or metabolite thereof, or a pharmaceutically acceptable salt, solvate or hydrate of the compound, enantiomer, diastereomer, racemate, tautomer, or metabolite, for the treatment or prevention of a disease associated with a cannabinoid receptor (e.g. CB1, CB2, 5HT1A, 5HT2A, GPR18, GPR55, GPR119, TRPV1, TRPV2, PPARγ, or a μ-opioid receptor).

In another aspect, the present disclosure relates to use of a pharmaceutical composition as described herein for the treatment or prevention of a disease associated with a cannabinoid receptor (e.g. CB1, CB2, 5HT1A, 5HT2A, GPR18, GPR55, GPR119, TRPV1, TRPV2, PPARγ, or a μ-opioid receptor).

In another aspect, the present disclosure relates to use of a compound as described herein, or an enantiomer, diastereomer, racemate, tautomer, or metabolite thereof, or a pharmaceutically acceptable salt, solvate or hydrate of the compound, enantiomer, diastereomer, racemate, tautomer, or metabolite, for selectively modulating the activity of a CB1 or CB2 receptor.

In another aspect, the present disclosure relates to use of a pharmaceutical composition as described herein, for selectively modulating the activity of a CB1 or CB2 receptor.

Other aspects and embodiments of the disclosure are evident in view of the detailed description provided herein.

DETAILED DESCRIPTION

The present disclosure provides compounds capable of acting as ligands to one or more cannabinoid receptors and/or prodrugs thereof. As used herein, "cannabinoid receptor" refers to a broad class of receptors that bind, interact with and/or are influenced functionally by cannabinoids or cannabinoid-like compounds. Without limitation, cannabinoid receptors may include CB1, CB2, 5HT1A, 5HT2A, GPR18, GPR55, GPR119, TRPV1, TRPV2, PPARs (e.g. PPARγ) or μ-opioid receptors. In an embodiment, the present disclosure further relates to compounds, pharmaceutical compositions, methods and uses having the potential for treating or preventing one or more diseases associated with a cannabinoid receptor.

The compounds of the present disclosure can be defined generically as with respect to formula (I) as appropriate,

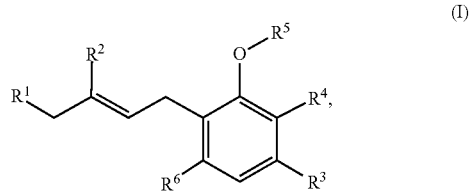

or in various subgenera compounds in which within the structural formula (I), $R^1$, $R^2$, $R^3$, $R^5$, $R^6$, $R^4$, and $R^{4a}$, $R^{4b}$, and $R^{4c}$ are optionally independently selected from the groups (Ia) to (Ie), (1a) to (1q), (2a) to (2s), (3a) to (3p), (4a) to (4c), (5a) to (5e), (6a) to (6e), and (7a) to (7gg) defined herein below (e.g., wherein the compound is of a structural formula as defined in any combination of the embodiments below):

In certain embodiments of the compounds as otherwise described herein, $R^1$ is selected from one of the following groups (1a)-(1q):

(1a) hydrogen, halo, $C_1$-$C_8$ alkyl, $C_2$-$C_8$ alkenyl, —$CO_2H$, —($C_0$-$C_4$ alkyl)-C(O)O($C_1$-$C_6$ alkyl), —$OR^{1a}$, —($C_1$-$C_4$ alkyl)$OR^{1a}$, —$SR^{1a}$, —($C_1$-$C_4$alkyl)$SR^{1a}$, —$NR^{1b}R^{1c}$, —($C_1$-$C_4$ alkyl)$NR^{1b}R^{1c}$, —($C_1$-$C_4$ alkyl)C(O)$NR^{1b}R^{1c}$, —($C_0$-$C_4$ alkyl)-aryl, —($C_0$-$C_4$ alkyl)-heteroaryl, —($C_0$-$C_4$ alkyl)-cycloalkyl, or —($C_0$-$C_4$ alkyl)-heterocycloalkyl;

(1b) The compound according to claim 1, wherein $R^1$ is hydrogen, —F, —$C_1$, $C_1$-$C_8$ alkyl, $C_2$-$C_8$ alkenyl, —$CO_2H$, —($C_0$-$C_4$ alkyl)-C(O)O($C_1$-$C_6$ alkyl), —($C_0$-$C_4$ alkyl)-aryl, —($C_0$-$C_4$ alkyl)-heteroaryl, —($C_0$-$C_4$ alkyl)-cycloalkyl, or —($C_0$-$C_4$ alkyl)-heterocycloalkyl;

(1c) hydrogen, —F, —$C_1$, $C_1$-$C_6$ alkyl, $C_2$-$C_6$ alkenyl, —$CO_2H$, or —($C_0$-$C_2$ alkyl)-C(O)O($C_1$-$C_6$ alkyl);

(1d) hydrogen;

(1e) hydrogen, $C_2$-$C_5$ alkyl, or $C_2$-$C_5$ alkenyl;

(1f) $C_1$-$C_6$ alkyl or $C_2$-$C_6$ alkenyl;

(1g) $C_1$-$C_6$ alkyl optionally substituted with hydroxy;

(1h) $C_1$-$C_6$ alkyl, e.g. methyl, ethyl, or propyl (such as isopropyl or n-propyl); (ii) $C_2$-$C_6$ alkenyl, e.g. isopropenyl;

(1j) $C_4$-$C_5$ alkenyl, e.g., but-2-en-1-yl or 3-methylbut-2-en-1-yl;

(1k) —$CO_2H$ or —C(O)O($C_1$-$C_4$ alkyl);

(1l) —$CO_2H$;

(1m) —$CH_2OH$;

(1n) —($C_0$-$C_4$ alkyl)-aryl, —($C_0$-$C_4$ alkyl)-heteroaryl, —($C_0$-$C_4$ alkyl)-cycloalkyl, or —($C_0$-$C_4$ alkyl)-heterocycloalkyl;

(1o) —$OR^{1a}$, —($C_1$-$C_4$ alkyl)$OR^{1a}$, —$SR^{1a}$, —($C_1$-$C_4$ alkyl)$SR^{1a}$, —$NR^{1b}R^{1c}$, —($C_1$-$C_4$ alkyl)$NR^{1b}R^{1c}$, or —($C_1$-$C_4$ alkyl)C(O)$NR^{1b}R^{1c}$;

(1p) —$OR^{1a}$, —($C_1$-$C_4$ alkyl)$OR^{1a}$, —$NR^{1b}R^{1c}$, —($C_1$-$C_4$ alkyl)$NR^{1b}R^{1c}$, or —($C_1$-$C_4$ alkyl)C(O)$NR^{1b}R^{1c}$;

(1q) as defined in (1o) and (1p), wherein $R^{1a}$, $R^{1b}$, and $R^{1c}$ are independently hydrogen or $C_1$-$C_4$ alkyl.

In certain embodiments of the compounds as otherwise described herein, $R^2$ is selected from one of the following groups (2a)-(2s):

(2a) hydrogen, halo, $C_1$-$C_8$ alkyl, $C_2$-$C_8$ alkenyl, —$CO_2H$, —($C_0$-$C_4$ alkyl)-C(O)O($C_1$-$C_6$ alkyl), —($C_1$-$C_4$ alkyl)$OR^{2a}$, —($C_1$-$C_4$ alkyl)$SR^{2a}$, —$NR^{2b}R^{2o}$, —($C_1$-$C_4$ alkyl)$NR^{2b}R^{2c}$, —($C_1$-$C_4$ alkyl)C(O)$NR^{2b}R^{2o}$, —($C_0$-$C_4$ alkyl)-aryl, —($C_0$-$C_4$ alkyl)-heteroaryl, —($C_0$-$C_4$ alkyl)-cycloalkyl, or —($C_0$-$C_4$ alkyl)-heterocycloalkyl;

(2b) hydrogen, —F, —$C_1$, $C_1$-$C_8$ alkyl, $C_2$-$C_8$ alkenyl, —$CO_2H$, —($C_1$-$C_4$ alkyl)-OH, —($C_0$-$C_4$ alkyl)-C(O)O($C_1$-$C_6$ alkyl), —($C_0$-$C_4$ alkyl)-aryl, —($C_0$-$C_4$ alkyl)-heteroaryl, —($C_0$-$C_4$ alkyl)-cycloalkyl, or —($C_0$-$C_4$ alkyl)-heterocycloalkyl;

(2c) hydrogen, —F, —$C_1$, $C_1$-$C_6$ alkyl, $C_2$-$C_6$ alkenyl, —($C_1$-$C_2$ alkyl)-OH, —$CO_2H$, or —($C_0$-$C_2$ alkyl)-C(O)O($C_1$-$C_6$ alkyl) (e.g., —$CO_2$($C_1$-$C_4$ alkyl));

(2d) hydrogen;

(2e) $C_1$-$C_4$ alkyl or $C_2$-$C_4$ alkenyl;

(2f) hydrogen, $C_1$-$C_4$ alkyl or $C_2$-$C_4$ alkenyl;

(2g) $C_1$-$C_4$ alkyl optionally substituted with hydroxy;

(2h) $C_1$-$C_4$ alkyl, e.g. methyl, ethyl, or propyl (such as isopropyl or n-propyl);

(2i) $C_2$-$C_4$ alkenyl, e.g. isopropenyl;

(2j) —$CO_2H$ or —C(O)O($C_1$-$C_4$ alkyl);

(2k) —$CO_2H$;

(2l) —$CH_2OH$;

(2m) —($C_0$-$C_4$ alkyl)-aryl, —($C_0$-$C_4$ alkyl)-heteroaryl, —($C_0$-$C_4$ alkyl)-cycloalkyl, or —($C_0$-$C_4$ alkyl)-heterocycloalkyl;

(2n) —$OR^{2a}$, —($C_1$-$C_4$ alkyl)$OR^{2a}$, —$SR^{2a}$, —($C_1$-$C_4$ alkyl)$SR^{2a}$, —$NR^{2b}R^{2c}$, —($C_1$-$C_4$ alkyl)$NR^{2b}R^{2c}$, or —($C_1$-$C_4$ alkyl)C(O)$NR^{2b}R^2C$;

(2o) —$OR^{2a}$, —($C_1$-$C_4$ alkyl)$OR^{2a}$, —$NR^{2b}R^{2c}$, —($C_1$-$C_4$ alkyl)$NR^{2b}R^{2c}$, or —($C_1$-$C_4$ alkyl)C(O)$NR^{2b}R^{2c}$;

(2p) —$OR^{2a}$;

(2q) —$NR^{2b}R^{2c}$;

(2r) as defined in (2n)-(2q), wherein $R^{2a}$, $R^{2b}$, and $R^{2c}$ are independently hydrogen, $C_1$-$C_4$ alkyl, or —C(O)$CH_3$;

(2s) as defined in (2n)-(2q), wherein $R^{2a}$, $R^2$b, and $R^{2c}$ are independently hydrogen or $C_1$-$C_4$ alkyl.

In certain embodiments of the compounds as otherwise described herein, $R^3$ is selected from one of the following groups (3a)-(3p):

(3a) hydrogen, $C_1$-$C_{12}$ alkyl, $C_2$-$C_{12}$ alkenyl, $C_2$-$C_{12}$ alkynyl, —(OCH$_2$CH$_2$)$_{0-6}$OCH$_3$, —($C_0$-$C_4$ alkyl)-aryl, —($C_0$-$C_4$ alkyl)-heteroaryl, —($C_0$-$C_4$ alkyl)-cycloalkyl or —($C_0$-$C_4$ alkyl)-heterocycloalkyl;

(3b) hydrogen, $C_1$-$C_{12}$ alkyl, —($C_0$-$C_4$ alkyl)-heteroaryl, —($C_0$-$C_4$ alkyl)-cycloalkyl or —($C_0$-$C_4$ alkyl)-heterocycloalkyl;

(3c) hydrogen, $C_1$—C alkyl, —($C_1$-$C_4$ alkyl)-heteroaryl or —($C_1$-$C_4$ alkyl)-heterocycloalkyl;

(3d) hydrogen, $C_4$-$C_9$ alkyl, —($C_1$-$C_2$ alkyl)-heteroaryl or —($C_1$-$C_2$ alkyl)-heterocycloalkyl;

(3e) hydrogen or $C_1$-$C_{10}$ alkyl;

(3f) hydrogen;

(3g) $C_2$-$C_9$ alkyl, e.g., unsubstituted n-$C_2$-$C_9$ alkyl;

(3h) $C_4$-$C_6$ alkyl, e.g., unsubstituted n-$C_4$-$C_6$ alkyl;

(3i) n-pentyl;

(3j) 1, 1-dimethylheptyl;

(3k) n-propyl;

(3l) —($C_0$-$C_4$ alkyl)-aryl, —($C_0$-$C_4$ alkyl)-heteroaryl, —($C_0$-$C_4$ alkyl)-cycloalkyl or —($C_0$-$C_4$ alkyl)-heterocycloalkyl;

(3m) —($C_0$-$C_4$ alkyl)-heterocycloalkyl, wherein the heterocycloalkyl has 3-8 ring members and 1-3 heteroatoms that are nitrogen, oxygen or sulfur and is substituted with 0-4 $R^7$;

(3n) —($C_0$-$C_4$ alkyl)-heterocycloalkyl, wherein the heterocycloalkyl has 3-8 ring members and 1-3 heteroatoms that are nitrogen, oxygen or sulfur and is substituted with 0-4 $R^7$, wherein the heterocycloalkyl is piperidinyl, pyrrolidinyl, azetidinyl, or aziridinyl;

(3o) —($C_0$-$C_4$ alkyl)-heterocycloalkyl, wherein the heterocycloalkyl has 3-8 ring members and 1-3 heteroatoms that are nitrogen, oxygen or sulfur and is substituted with 0-4 $R^7$, wherein the heterocycloalkyl is azetidinyl and is substituted with 1-2 $R^7$, which are independently oxo, $C_1$-$C_4$alkyl, $C_1$, F, Br, —C(O)$R^A$, or —$O_2R^A$, wherein $R^A$ is H or $C_1$-$C_3$ alkyl;

(3p) —($C_0$-$C_4$ alkyl)-heterocycloalkyl, wherein the heterocycloalkyl has 3-8 ring members and 1-3 heteroatoms that are nitrogen, oxygen or sulfur and is substituted with 0-4 $R^7$, wherein $R^7$, is —C(O)$CH_3$.

In certain embodiments of the compounds as otherwise described herein, $R^5$ are independently selected from one of the following groups (4a)-(4c):

(4a) hydrogen, $C_1$-$C_6$ alkyl, —($C_1$-$C_4$ alkyl)-O—($C_1$-$C_4$ alkyl), —C(O)($C_1$-$C_4$ alkyl), —C(O)O($C_1$-$C_4$ alkyl), —C(O)$NH_2$, —C(O)NH($C_1$-$C_4$ alkyl), or —C(O)N($C_1$-$C_4$ alkyl)$_2$;

(4b) hydrogen, $C_1$-$C_6$ alkyl, or —($C_1$-$C_4$ alkyl)-O—($C_1$-$C_4$ alkyl);

(4c) hydrogen.

In certain embodiments of the compounds as otherwise described herein, $R^6$ are independently selected from one of the following groups (5a)-(5e):

(5a) hydrogen;
(5b) —$OR^{6a}$;
(5c) —$OR^{6a}$, wherein $R^{6a}$ is hydrogen, $C_1$-$C_6$ alkyl, —($C_1$-$C_4$ alkyl)-O—($C_1$-$C_4$ alkyl), —C(O)($C_1$-$C_4$ alkyl), —C(O)O($C_1$-$C_4$ alkyl), —C(O)$NH_2$, —C(O)NH($C_1$-$C_4$ alkyl), or —C(O)N($C_1$-$C_4$ alkyl)$_2$;
(5d) —$OR^{6a}$, wherein $R^{6a}$ is hydrogen, $C_1$-$C_6$ alkyl, or —($C_1$-$C_4$ alkyl)-O—($C_1$-$C_4$ alkyl);
(5e) —OH.

In certain embodiments of the compounds as otherwise described herein, the compound has the structural formulae (Ia)-(Ie):

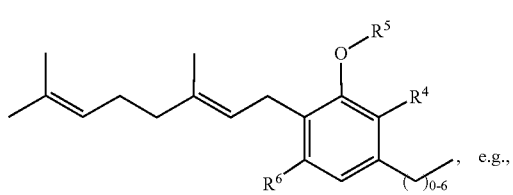

(Ia), e.g.,

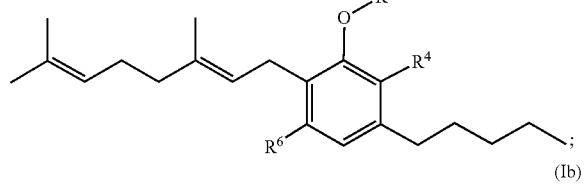

(Ib);

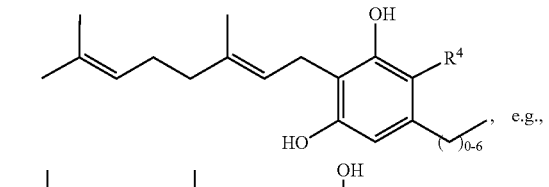

(Ic), e.g.,

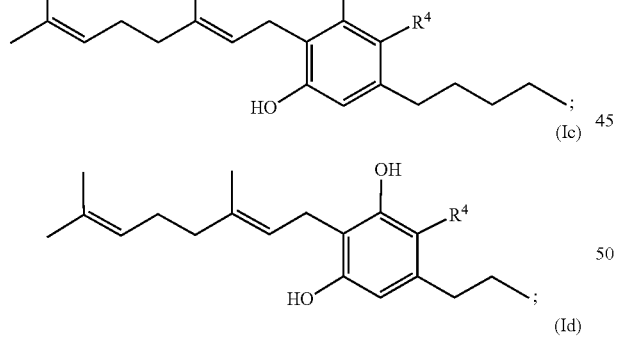

(Id);

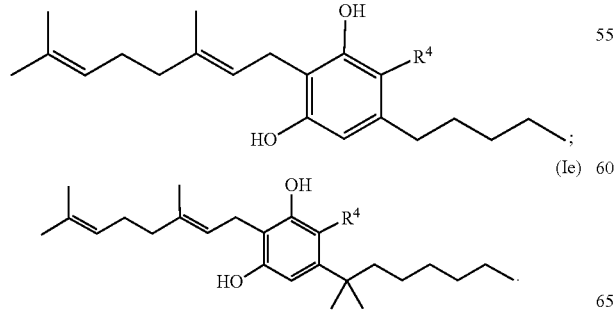

(Ie)

In certain embodiments of the compounds as otherwise described herein, $R^4$ is selected from one of the following groups (6a)-(6e):

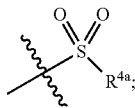

(6a)

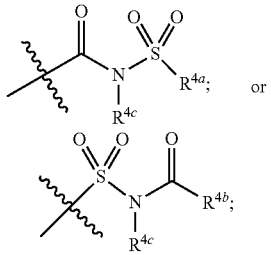

(6b); or

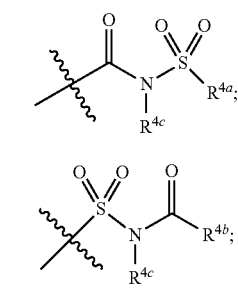

(6c)

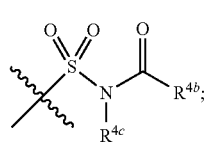

(6d);

(6e) sulfo, methylsulfonyl, cyclopropylsulfonyl, tert-butylsulfonyl, benzylsulfonyl, phenylsulfonyl, (4-nitrophenyl)sulfonyl, pyridin-3-ylsulfonyl, furan-2-ylsulfonyl, (1H-imidazol-4-yl)sulfonyl, oxetan-3-ylsulfonyl, perfluorophenylsulfonyl, (4-oxocyclohexyl)sulfonyl, (2-(2,5-dioxopyrrolidin-1-yl)ethyl)sulfonyl, (2-(dimethylamino)ethyl)sulfonyl, (1-acetylpiperidin-3-yl)sulfonyl, (2-chloropyrimidin-5-yl)sulfonyl, sulfamoyl, N-methylsulfamoyl, N,N-dimethylsulfamoyl, N-cyclopropylsulfamoyl, N-isopropylsulfamoyl, N-phenylsulfamoyl, N-benzylsulfamoyl, (4-methylpiperazin-1-yl)sulfonyl, piperidin-1-ylsulfonyl, morpholinosulfonyl, N-(pyridin-3-yl)sulfamoyl, N-(pyrimidin-2-yl)sulfamoyl, N-(2-oxopropyl)sulfamoyl, (3-oxoazetidin-1-yl)sulfonyl, N-(oxetan-2-ylmethyl)sulfamoyl, (2-azaspiro[3.3]heptan-2-yl)sulfonyl, (2,6-diazaspiro[3.3]heptan-2-yl)sulfonyl, N-(1-carboxyethyl)sulfamoyl, N-(1-methoxy-1-oxopropan-2-yl)sulfamoyl, N-(3-morpholinopropanoyl)sulfamoyl, N-(3-carboxypropanoyl)sulfamoyl, N-(3-(4-methylpiperazin-1-yl)propanoyl)sulfamoyl, N-glycylsulfamoyl, N-(2-(2-methoxyethoxy)acetyl)sulfamoyl, N-serylsulfamoyl, N-alanylsulfamoyl, (3-amino-2-methylpropanoyl)sulfamoyl, N-acetylsulfamoyl, N-(3-oxobutanoyl)sulfamoyl, N-(2-(3-methyl-1H-1,2,4-triazol-5-yl)acetyl)sulfamoyl, N-(1H-1,2,4-triazole-5-carbonyl)sulfamoyl, N-(cyclobutanecarbonyl)sulfamoyl, N-benzoylsulfamoyl, N-nicotinoylsulfamoyl, N-(2-phenylacetyl)sulfamoyl, N-(2-(furan-2-yl)acetyl)sulfamoyl, N-(2-(oxazol-2-yl)acetyl)sulfamoyl, N-(2-(thiazol-2-yl)acetyl)sulfamoyl, N-(2-(1H-benzo[d]imidazole-2-yl)acetyl)sulfamoyl, (phenylsulfonyl)carbamoyl, (cyclohexylsulfonyl)carbamoyl, (prop-1-en-1-ylsulfonyl)carbamoyl, ((1H-benzo[d]imidazol-2-yl)sulfonyl)carbamoyl.

In certain embodiments of the compounds as otherwise described herein, $R^{4a}$, $R^{4b}$, or $R^{4c}$ is selected from one of the following groups (7a)-(7gg) as appropriate:

(7a) as defined in (6a)-(6c), wherein $R^{4a}$ is $C_1$-$C_8$ alkyl, $C_2$-$C_8$ alkenyl, —$OR^{4e}$, —($C_1$-$C_4$ alkyl)$OR^{4e}$, —($C_1$-$C_4$ alkyl)-C(O)($C_1$-$C_4$ alkyl), —($C_0$-$C_4$ alkyl)-aryl, —($C_0$-$C_4$ alkyl)-heteroaryl, —($C_0$-$C_4$ alkyl)-cycloalkyl, —($C_0$-$C_4$ alkyl)-heterocycloalkyl, —$NR^{4d}R^{4e}$, or —($C_1$-$C_4$ alkyl)$NR^{4d}R^{4e}$;

(7b) as defined in (6a)-(6c), wherein $R^{4a}$ is $C_1$-$C_8$ alkyl, $C_2$-$C_8$ alkenyl, or —$OR^{4e}$;

(7c) as defined in (6a)-(6c), wherein $R^{4a}$ is $C_2$-$C_6$ alkenyl (e.g., propenyl or 3-methoxyprop-1-en-1-yl);

(7d) as defined in (6a)-(6c), wherein $R^{4a}$ is $C_1$-$C_4$ alkyl (e.g., methyl or tert-butyl);

(7e) as defined in (6a)-(6c), wherein $R^{4a}$ is —$OR^{4e}$ (e.g., —OH or —ONa);

(7f) as defined in (6a)-(6c), wherein $R^{4a}$ is $C_1$-$C_8$ alkyl, $C_2$-$C_8$ alkenyl, —($C_0$-$C_4$ alkyl)-aryl, —($C_0$-$C_4$ alkyl)-heteroaryl, —($C_0$-$C_4$ alkyl)-cycloalkyl, or —($C_0$-$C_4$ alkyl)-heterocycloalkyl;

(7g) as defined in (6a)-(6c), wherein $R^{4a}$ is —($C_0$-$C_4$ alkyl)-aryl, —($C_0$-$C_4$ alkyl)-heteroaryl, —($C_0$-$C_4$ alkyl)-cycloalkyl, or —($C_0$-$C_4$ alkyl)-heterocycloalkyl;

(7h) as defined in (6a)-(6c), wherein $R^{4a}$ is monocyclic —($C_0$—C, alkyl)-aryl (e.g., phenyl or benzyl), monocyclic or bicyclic —($C_0$—C, alkyl)-heteroaryl (e.g., pyridiyl, triazolyl, oxazolyl, furanyl, imidazolyl, pyrimidinyl. or benzimidazolyl), monocyclic —($C_0$—C, alkyl)-cycloalkyl. (e.g. cyclopropyl, cyclopropanyl or cyclohexyl) or monocyclic —($C_0$-$C_2$ alkyl)-heterocycloalkyl (e.g., oxetanylmethyl, azetidinyl, azaspiro[3.3]heptanyl, diazaspiro[3.3]heptanyl, oxetanyl, morpholinyl, piperazinyl, pyrrolidinyl, or piperidinyl);

(7i) as defined in (6a)-(6c), wherein $R^{4a}$ is monocyclic —($C_0$—C, alkyl)-aryl (e.g., phenyl or benzyl) or monocyclic —($C_0$—C, alkyl)-cycloalkyl. (e.g. cyclopropyl, cyclopropanyl or cyclohexyl);

(7j) as defined in (6a)-(6c), wherein $R^{4a}$ is monocyclic or bicyclic —($C_0$—C, alkyl)-heteroaryl (e.g., pyridiyl, triazolyl, oxazolyl, furanyl, imidazolyl, pyrimidinyl. or benzimidazolyl) or monocyclic —($C_0$-$C_2$ alkyl)-heterocycloalkyl (e.g., oxetanylmethyl, azetidinyl, azaspiro[3.3]heptanyl, diazaspiro[3.3]heptanyl, oxetanyl, morpholinyl, piperazinyl, pyrrolidinyl, or piperidinyl);

(7k) as defined in (7h)-(7j), wherein $R^8$ is independently $C_1$-$C_4$ alkyl, —F, —$C_1$, nitro, amino, methoxymethyl, cyclopropyl, phenyl, pyridyl, or —$NR^B C(O)R^A$, wherein $R^B$ is hydrogen or methyl and $R^A$ is hydrogen or $C_1$-$C_4$ alkyl;

(7l) as defined in (7h)-(7k), wherein each $R^7$ is independently $C_1$-$C_4$ alkyl, methoxymethyl, —F, —$C_1$, hydroxy, oxo, cyclopropyl, phenyl, or pyridyl;

(7m) as defined in (6a)-(6c), wherein $R^{4a}$ is —($C_1$-$C_4$ alkyl)$NR^{4d}R^{4e}$ (e.g., wherein $R^{4d}$ and $R^{4a}$ are independently H or $C_1$-$C_4$ alkyl, such as (dimethylamino)ethyl, aminopropan-2-yl, aminoethyl or 1-amino-2-hydroxyethyl);

(7n) as defined in (6a)-(6c), wherein $R^{4a}$ is —$NR^{4d}R^{4e}$;

(7o) as defined in (6a)-(6c), wherein $R^{4a}$ is $NR^{4d}R^{4e}$, wherein $R^{4d}$ is hydrogen, $C_1$-$C_4$ alkyl, —($C_1$-$C_4$ alkyl)-C(O)O($R^{4e}$), —($C_0$-$C_2$ alkyl)-aryl, —($C_0$-$C_2$ alkyl)-heteroaryl, —($C_0$-$C_2$ alkyl)-cycloalkyl, or —($C_0$-$C_2$ alkyl)-heterocycloalkyl and $R^{4e}$ is hydrogen or $C_1$-$C_4$ alkyl;

(7p) as defined in (6a)-(6c), wherein $R^{4a}$ is —$NR^{4d}R^{4e}$, wherein $R^{4d}$ is hydrogen, $C_1$-$C_4$ alkyl, or $C_2$-$C_4$ alkenyl and $R^{4e}$ is hydrogen or methyl;

(7q) as defined in (6a)-(6c), wherein $R^{4a}$ is —$NR^{4d}R^{4e}$, wherein $R^{4d}$ is —($C_0$-$C_1$ alkyl)-aryl, —($C_0$—C, alkyl)-heteroaryl, —($C_0$—C, alkyl)-cycloalkyl, or —($C_0$—C, alkyl)-heterocycloalkyl and $R^{4e}$ is hydrogen or methyl;

(7r) as defined in (6b) or (6d), wherein $R^{4b}$ is $C_1$—C alkyl, $C_2$-$C_8$ alkenyl, —$CH_2$—(OCH$_2$CH$_2$)$_{0-6}$O($C_1$-$C_6$ alkyl), —($C_1$-$C_4$ alkyl)-C(O)O($R^{4e}$), —($C_1$-$C_4$ alkyl)$OR^{4e}$, —($C_1$-$C_4$ alkyl)-C(O)($C_1$-$C_4$ alkyl), —($C_0$-$C_4$ alkyl)-aryl, —($C_0$-$C_4$ alkyl)-heteroaryl, —($C_0$-$C_4$ alkyl)-cycloalkyl, —($C_0$-$C_4$ alkyl)-heterocycloalkyl, or —($C_1$-$C_4$ alkyl)$NR^{4d}R^{4e}$;

(7s) as defined in (6b) or (6d), wherein $R^{4b}$ is $C_1$—C alkyl, $C_2$-$C_8$ alkenyl, or —($C_1$-$C_4$ alkyl)$OR^{4e}$;

(7t) as defined in (6b) or (6d), wherein $R^{4b}$ is $C_1$-$C_4$ alkyl, e.g., methyl;

(7u) as defined in (6b) or (6d), wherein $R^{4b}$ is —$CH_2$—(OCH$_2$CH$_2$)$_{0-4}$O($C_1$-$C_6$ alkyl), —($C_1$-$C_4$ alkyl)-C(O)O ($R^{4e}$) (e.g., —($C_1$-$C_4$ alkyl)-C(O)OH), or —($C_1$-$C_4$ alkyl)-C(O)($C_1$-$C_4$ alkyl) (e.g., —$CH_2C(O)CH_3$);

(7v) as defined in (6b) or (6d), wherein $R^{4b}$ is $C_1$—C alkyl, $C_2$-$C_8$ alkenyl, —($C_0$-$C_4$ alkyl)-aryl, —($C_0$-$C_4$ alkyl)-heteroaryl, —($C_0$-$C_4$ alkyl)-cycloalkyl, or —($C_0$-$C_4$ alkyl)-heterocycloalkyl;

(7w) as defined in (6b) or (6d), wherein $R^{4b}$ is —($C_0$-$C_4$ alkyl)-aryl, —($C_0$-$C_4$ alkyl)-heteroaryl, —($C_0$-$C_4$ alkyl)-cycloalkyl, or —($C_0$-$C_4$ alkyl)-heterocycloalkyl;

(7x) as defined in (6b) or (6d), wherein $R^{4b}$ monocyclic —($C_0$—C, alkyl)-aryl (e.g., phenyl or benzyl), monocyclic or bicyclic —($C_0$—C, alkyl)-heteroaryl (e.g., pyridiyl, triazolyl, oxazolyl, furanyl, imidazolyl, pyrimidinyl. or benzimidazolyl), monocyclic —($C_0$—C, alkyl)-cycloalkyl. (e.g. cyclopropyl, cyclopropanyl or cyclohexyl) or monocyclic —($C_0$-$C_2$ alkyl)-heterocycloalkyl (e.g., oxetanylmethyl, azetidinyl, azaspiro[3.3]heptanyl, diazaspiro[3.3]heptanyl, oxetanyl, morpholinyl, piperazinyl, pyrrolidinyl, or piperidinyl);

(7y) as defined in (6b) or (6d), wherein $R^{4b}$ is monocyclic —($C_0$—C, alkyl)-aryl (e.g., phenyl or benzyl) or monocyclic —($C_0$—C, alkyl)-cycloalkyl. (e.g. cyclopropyl, cyclopropanyl or cyclohexyl);

(7z) as defined in (6b) or (6d), wherein $R^{4b}$ is monocyclic or bicyclic —($C_0$—C, alkyl)-heteroaryl (e.g., pyridiyl, triazolyl, oxazolyl, furanyl, imidazolyl, pyrimidinyl. or benzimidazolyl) or monocyclic —($C_0$-$C_2$ alkyl)-heterocycloalkyl (e.g., oxetanylmethyl, azetidinyl, azaspiro[3.3]heptanyl, diazaspiro[3.3]heptanyl, oxetanyl, morpholinyl, piperazinyl, pyrrolidinyl, or piperidinyl);

(7aa) as defined in (7v)-(7z), wherein each $R^8$ is independently $C_1$-$C_4$ alkyl, —F, —$C_1$, nitro, amino, methoxymethyl, cyclopropyl, phenyl, pyridyl, or —$NR^B C(O)R^A$, wherein $R^B$ is hydrogen or methyl and $R^A$ is hydrogen or $C_1$-$C_4$ alkyl;

(7bb) as defined in (7v)-(7aa), wherein each $R^7$ is independently $C_1$-$C_4$ alkyl, methoxymethyl, —F, —$C_1$, hydroxy, oxo, cyclopropyl, phenyl, or pyridyl;

(7cc) as defined in (6b) or (6d), wherein $R^{4b}$ is —($C_1$-$C_4$ alkyl)$NR^{4d}R^{4e}$ (e.g., wherein $R^{4d}$ and $R^{4a}$ are independently H or $C_1$-$C_4$ alkyl, such as (dimethylamino)ethyl, aminopropan-2-yl, aminoethyl or 1-amino-2-hydroxyethyl);

(7dd) as defined in (6b)-(6d) or (7a)-(7y), wherein $R^{4a}$ is hydrogen;

(7ee) as defined in (6b)-(6d) or (7a)-(7y), wherein $R^{4a}$ is $C_1$-$C_4$ alkyl, e.g., methyl.

(7ff) as defined in (7a), (7m), (7r), or (7cc), wherein $R^{4d}$ is hydrogen or $C_1$-$C_6$ alkyl (e.g., methyl, ethyl, or propyl).

(7gg) as defined in (7a), (7m), (7r), or (7cc), wherein $R^{4e}$ is hydrogen, methyl, or aryl.

Various particular embodiment nos. 1-477 of compounds of the present disclosure include compounds of formula (I), each as defined in each of the following rows (or enantiomers, diastereomers, racemates, tautomers, or metabolites thereof, or pharmaceutically acceptable salts, solvates or hydrates of the compounds, enantiomers, diastereomers, racemates, tautomers, or metabolites), wherein each entry is a group number as defined above:

| Embodiment | $R^1$ | $R^2$ | $R^3$ | $R^5$ | $R^6$ | $R^4$ | $R^{4a}$ | $R^{4b}$ | $R^{4c}$ |
|---|---|---|---|---|---|---|---|---|---|
| 1 | (1d) | (2c) | (3a) | (4b) | (5d) | (6a) | (7a) | — | — |
| 2 | (1d) | (2c) | (3a) | (4b) | (5d) | (6a) | (7b), (7g) | — | — |
| 3 | (1d) | (2c) | (3a) | (4b) | (5d) | (6c) | (7a) | — | (7dd) |
| 4 | (1d) | (2c) | (3a) | (4b) | (5d) | (6c) | (7b), (7g) | — | (7dd) |
| 5 | (1d) | (2c) | (3a) | (4b) | (5d) | (6d) | — | (7r) | (7dd) |
| 6 | (1d) | (2c) | (3a) | (4b) | (5d) | (6d) | — | (7s), (7w) | (7dd) |
| 7 | (1d) | (2c) | (3a) | (4b) | (5e) | (6a) | (7a) | — | — |
| 8 | (1d) | (2c) | (3a) | (4b) | (5e) | (6a) | (7b), (7g) | — | — |
| 9 | (1d) | (2c) | (3a) | (4b) | (5e) | (6c) | (7a) | — | (7dd) |
| 10 | (1d) | (2c) | (3a) | (4b) | (5e) | (6c) | (7b), (7g) | — | (7dd) |
| 11 | (1d) | (2c) | (3a) | (4b) | (5e) | (6d) | — | (7r) | (7dd) |
| 12 | (1d) | (2c) | (3a) | (4b) | (5e) | (6d) | — | (7s), (7w) | (7dd) |
| 13 | (1d) | (2c) | (3a) | (4c) | (5d) | (6a) | (7a) | — | — |
| 14 | (1d) | (2c) | (3a) | (4c) | (5d) | (6a) | (7b), (7g) | — | — |
| 15 | (1d) | (2c) | (3a) | (4c) | (5d) | (6c) | (7a) | — | (7dd) |
| 16 | (1d) | (2c) | (3a) | (4c) | (5d) | (6c) | (7b), (7g) | — | (7dd) |
| 17 | (1d) | (2c) | (3a) | (4c) | (5d) | (6d) | — | (7r) | (7dd) |
| 18 | (1d) | (2c) | (3a) | (4c) | (5d) | (6d) | — | (7s), (7w) | (7dd) |
| 19 | (1d) | (2c) | (3a) | (4c) | (5e) | (6a) | (7a) | — | — |
| 20 | (1d) | (2c) | (3a) | (4c) | (5e) | (6a) | (7b), (7g) | — | — |
| 21 | (1d) | (2c) | (3a) | (4c) | (5e) | (6c) | (7a) | — | (7dd) |
| 22 | (1d) | (2c) | (3a) | (4c) | (5e) | (6c) | (7b), (7g) | — | (7dd) |
| 23 | (1d) | (2c) | (3a) | (4c) | (5e) | (6d) | — | (7r) | (7dd) |
| 24 | (1d) | (2c) | (3a) | (4c) | (5e) | (6d) | — | (7s), (7w) | (7dd) |
| 25 | (1d) | (2c) | (3d) | (4b) | (5d) | (6a) | (7a) | — | — |
| 26 | (1d) | (2c) | (3d) | (4b) | (5d) | (6a) | (7b), (7g) | — | — |
| 27 | (1d) | (2c) | (3d) | (4b) | (5d) | (6c) | (7a) | — | (7dd) |
| 28 | (1d) | (2c) | (3d) | (4b) | (5d) | (6c) | (7b), (7g) | — | (7dd) |
| 29 | (1d) | (2c) | (3d) | (4b) | (5d) | (6d) | — | (7r) | (7dd) |
| 30 | (1d) | (2c) | (3d) | (4b) | (5d) | (6d) | — | (7s), (7w) | (7dd) |
| 31 | (1d) | (2c) | (3d) | (4b) | (5e) | (6a) | (7a) | — | — |
| 32 | (1d) | (2c) | (3d) | (4b) | (5e) | (6a) | (7b), (7g) | — | — |
| 33 | (1d) | (2c) | (3d) | (4b) | (5e) | (6c) | (7a) | — | (7dd) |
| 34 | (1d) | (2c) | (3d) | (4b) | (5e) | (6c) | (7b), (7g) | — | (7dd) |
| 35 | (1d) | (2c) | (3d) | (4b) | (5e) | (6d) | — | (7r) | (7dd) |
| 36 | (1d) | (2c) | (3d) | (4b) | (5e) | (6d) | — | (7s), (7w) | (7dd) |
| 37 | (1d) | (2c) | (3d) | (4c) | (5d) | (6a) | (7a) | — | — |
| 38 | (1d) | (2c) | (3d) | (4c) | (5d) | (6a) | (7b), (7g) | — | — |
| 39 | (1d) | (2c) | (3d) | (4c) | (5d) | (6c) | (7a) | — | (7dd) |
| 40 | (1d) | (2c) | (3d) | (4c) | (5d) | (6c) | (7b), (7g) | — | (7dd) |
| 41 | (1d) | (2c) | (3d) | (4c) | (5d) | (6d) | — | (7r) | (7dd) |
| 42 | (1d) | (2c) | (3d) | (4c) | (5d) | (6d) | — | (7s), (7w) | (7dd) |
| 43 | (1d) | (2c) | (3d) | (4c) | (5e) | (6a) | (7a) | — | — |
| 44 | (1d) | (2c) | (3d) | (4c) | (5e) | (6a) | (7b), (7g) | — | — |
| 45 | (1d) | (2c) | (3d) | (4c) | (5e) | (6c) | (7a) | — | (7dd) |
| 46 | (1d) | (2c) | (3d) | (4c) | (5e) | (6c) | (7b), (7g) | — | (7dd) |
| 47 | (1d) | (2c) | (3d) | (4c) | (5e) | (6d) | — | (7r) | (7dd) |
| 48 | (1d) | (2c) | (3d) | (4c) | (5e) | (6d) | — | (7s), (7w) | (7dd) |
| 49 | (1d) | (2c) | (3g), (3i), (3j), (3k) | (4b) | (5d) | (6a) | (7a) | — | — |
| 50 | (1d) | (2c) | (3g), (3i), (3j), (3k) | (4b) | (5d) | (6a) | (7b), (7g) | — | — |
| 51 | (1d) | (2c) | (3g), (3i), (3j), (3k) | (4b) | (5d) | (6c) | (7a) | — | (7dd) |
| 52 | (1d) | (2c) | (3g), (3i), (3j), (3k) | (4b) | (5d) | (6c) | (7b), (7g) | — | (7dd) |
| 53 | (1d) | (2c) | (3g), (3i), (3j), (3k) | (4b) | (5d) | (6d) | — | (7r) | (7dd) |
| 54 | (1d) | (2c) | (3g), (3i), (3j), (3k) | (4b) | (5d) | (6d) | — | (7s), (7w) | (7dd) |
| 55 | (1d) | (2c) | (3g), (3i), (3j), (3k) | (4b) | (5e) | (6a) | (7a) | — | — |
| 56 | (1d) | (2c) | (3g), (3i), (3j), (3k) | (4b) | (5e) | (6a) | (7b), (7g) | — | — |
| 57 | (1d) | (2c) | (3g), (3i), (3j), (3k) | (4b) | (5e) | (6c) | (7a) | — | (7dd) |
| 58 | (1d) | (2c) | (3g), (3i), (3j), (3k) | (4b) | (5e) | (6c) | (7b), (7g) | — | (7dd) |

-continued

| Embodiment | $R^1$ | $R^2$ | $R^3$ | $R^5$ | $R^6$ | $R^4$ | $R^{4a}$ | $R^{4b}$ | $R^{4c}$ |
|---|---|---|---|---|---|---|---|---|---|
| 59 | (1d) | (2c) | (3g), (3i), (3j), (3k) | (4b) | (5e) | (6d) | — | (7r) | (7dd) |
| 60 | (1d) | (2c) | (3g), (3i), (3j), (3k) | (4b) | (5e) | (6d) | — | (7s), (7w) | (7dd) |
| 61 | (1d) | (2c) | (3g), (3i), (3j), (3k) | (4c) | (5d) | (6a) | (7a) | — | — |
| 62 | (1d) | (2c) | (3g), (3i), (3j), (3k) | (4c) | (5d) | (6a) | (7b), (7g) | — | — |
| 63 | (1d) | (2c) | (3g), (3i), (3j), (3k) | (4c) | (5d) | (6c) | (7a) | — | (7dd) |
| 64 | (1d) | (2c) | (3g), (3i), (3j), (3k) | (4c) | (5d) | (6c) | (7b), (7g) | — | (7dd) |
| 65 | (1d) | (2c) | (3g), (3i), (3j), (3k) | (4c) | (5d) | (6d) | — | (7r) | (7dd) |
| 66 | (1d) | (2c) | (3g), (3i), (3j), (3k) | (4c) | (5d) | (6d) | — | (7s), (7w) | (7dd) |
| 67 | (1d) | (2c) | (3g), (3i), (3j), (3k) | (4c) | (5e) | (6a) | (7a) | — | — |
| 68 | (1d) | (2c) | (3g), (3i), (3j), (3k) | (4c) | (5e) | (6a) | (7b), (7g) | — | — |
| 69 | (1d) | (2c) | (3g), (3i), (3j), (3k) | (4c) | (5e) | (6c) | (7a) | — | (7dd) |
| 70 | (1d) | (2c) | (3g), (3i), (3j), (3k) | (4c) | (5e) | (6c) | (7b), (7g) | — | (7dd) |
| 71 | (1d) | (2c) | (3g), (3i), (3j), (3k) | (4c) | (5e) | (6d) | — | (7r) | (7dd) |
| 72 | (1d) | (2c) | (3g), (3i), (3j), (3k) | (4c) | (5e) | (6d) | — | (7s), (7w) | (7dd) |
| 73 | (1d) | (2g) | (3a) | (4b) | (5d) | (6a) | (7a) | — | — |
| 74 | (1d) | (2g) | (3a) | (4b) | (5d) | (6a) | (7b), (7g) | — | — |
| 75 | (1d) | (2g) | (3a) | (4b) | (5d) | (6c) | (7a) | — | (7dd) |
| 76 | (1d) | (2g) | (3a) | (4b) | (5d) | (6c) | (7b), (7g) | — | (7dd) |
| 77 | (1d) | (2g) | (3a) | (4b) | (5d) | (6d) | — | (7r) | (7dd) |
| 78 | (1d) | (2g) | (3a) | (4b) | (5d) | (6d) | — | (7s), (7w) | (7dd) |
| 79 | (1d) | (2g) | (3a) | (4b) | (5e) | (6a) | (7a) | — | — |
| 80 | (1d) | (2g) | (3a) | (4b) | (5e) | (6a) | (7b), (7g) | — | — |
| 81 | (1d) | (2g) | (3a) | (4b) | (5e) | (6c) | (7a) | — | (7dd) |
| 82 | (1d) | (2g) | (3a) | (4b) | (5e) | (6c) | (7b), (7g) | — | (7dd) |
| 83 | (1d) | (2g) | (3a) | (4b) | (5e) | (6d) | — | (7r) | (7dd) |
| 84 | (1d) | (2g) | (3a) | (4b) | (5e) | (6d) | — | (7s), (7w) | (7dd) |
| 85 | (1d) | (2g) | (3a) | (4c) | (5d) | (6a) | (7a) | — | — |
| 86 | (1d) | (2g) | (3a) | (4c) | (5d) | (6a) | (7b), (7g) | — | — |
| 87 | (1d) | (2g) | (3a) | (4c) | (5d) | (6c) | (7a) | — | (7dd) |
| 88 | (1d) | (2g) | (3a) | (4c) | (5d) | (6c) | (7b), (7g) | — | (7dd) |
| 89 | (1d) | (2g) | (3a) | (4c) | (5d) | (6d) | — | (7r) | (7dd) |
| 90 | (1d) | (2g) | (3a) | (4c) | (5d) | (6d) | — | (7s), (7w) | (7dd) |
| 91 | (1d) | (2g) | (3a) | (4c) | (5e) | (6a) | (7a) | — | — |
| 92 | (1d) | (2g) | (3a) | (4c) | (5e) | (6a) | (7b), (7g) | — | — |
| 93 | (1d) | (2g) | (3a) | (4c) | (5e) | (6c) | (7a) | — | (7dd) |
| 94 | (1d) | (2g) | (3a) | (4c) | (5e) | (6c) | (7b), (7g) | — | (7dd) |
| 95 | (1d) | (2g) | (3a) | (4c) | (5e) | (6d) | — | (7r) | (7dd) |
| 96 | (1d) | (2g) | (3a) | (4c) | (5e) | (6d) | — | (7s), (7w) | (7dd) |
| 97 | (1d) | (2g) | (3d) | (4b) | (5d) | (6a) | (7a) | — | — |
| 98 | (1d) | (2g) | (3d) | (4b) | (5d) | (6a) | (7b), (7g) | — | — |
| 99 | (1d) | (2g) | (3d) | (4b) | (5d) | (6c) | (7a) | — | (7dd) |
| 100 | (1d) | (2g) | (3d) | (4b) | (5d) | (6c) | (7b), (7g) | — | (7dd) |
| 101 | (1d) | (2g) | (3d) | (4b) | (5d) | (6d) | — | (7r) | (7dd) |
| 102 | (1d) | (2g) | (3d) | (4b) | (5d) | (6d) | — | (7s), (7w) | (7dd) |
| 103 | (1d) | (2g) | (3d) | (4b) | (5e) | (6a) | (7a) | — | — |
| 104 | (1d) | (2g) | (3d) | (4b) | (5e) | (6a) | (7b), (7g) | — | — |
| 105 | (1d) | (2g) | (3d) | (4b) | (5e) | (6c) | (7a) | — | (7dd) |
| 106 | (1d) | (2g) | (3d) | (4b) | (5e) | (6c) | (7b), (7g) | — | (7dd) |
| 107 | (1d) | (2g) | (3d) | (4b) | (5e) | (6d) | — | (7r) | (7dd) |
| 108 | (1d) | (2g) | (3d) | (4b) | (5e) | (6d) | — | (7s), (7w) | (7dd) |
| 109 | (1d) | (2g) | (3d) | (4c) | (5d) | (6a) | (7a) | — | — |
| 110 | (1d) | (2g) | (3d) | (4c) | (5d) | (6a) | (7b), (7g) | — | — |
| 111 | (1d) | (2g) | (3d) | (4c) | (5d) | (6c) | (7a) | — | (7dd) |
| 112 | (1d) | (2g) | (3d) | (4c) | (5d) | (6c) | (7b), (7g) | — | (7dd) |
| 113 | (1d) | (2g) | (3d) | (4c) | (5d) | (6d) | — | (7r) | (7dd) |
| 114 | (1d) | (2g) | (3d) | (4c) | (5d) | (6d) | — | (7s), (7w) | (7dd) |
| 115 | (1d) | (2g) | (3d) | (4c) | (5e) | (6a) | (7a) | — | — |
| 116 | (1d) | (2g) | (3d) | (4c) | (5e) | (6a) | (7b), (7g) | — | — |
| 117 | (1d) | (2g) | (3d) | (4c) | (5e) | (6c) | (7a) | — | (7dd) |
| 118 | (1d) | (2g) | (3d) | (4c) | (5e) | (6c) | (7b), (7g) | — | (7dd) |
| 119 | (1d) | (2g) | (3d) | (4c) | (5e) | (6d) | — | (7r) | (7dd) |
| 120 | (1d) | (2g) | (3d) | (4c) | (5e) | (6d) | — | (7s), (7w) | (7dd) |

-continued

| Embodiment | R¹ | R² | R³ | R⁵ | R⁶ | R⁴ | R⁴ᵃ | R⁴ᵇ | R⁴ᶜ |
|---|---|---|---|---|---|---|---|---|---|
| 121 | (1d) | (2g) | (3g), (3i), (3j), (3k) | (4b) | (5d) | (6a) | (7a) | — | — |
| 122 | (1d) | (2g) | (3g), (3i), (3j), (3k) | (4b) | (5d) | (6a) | (7b), (7g) | — | — |
| 123 | (1d) | (2g) | (3g), (3i), (3j), (3k) | (4b) | (5d) | (6c) | (7a) | — | (7dd) |
| 124 | (1d) | (2g) | (3g), (3i), (3j), (3k) | (4b) | (5d) | (6c) | (7b), (7g) | — | (7dd) |
| 125 | (1d) | (2g) | (3g), (3i), (3j), (3k) | (4b) | (5d) | (6d) | — | (7r) | (7dd) |
| 126 | (1d) | (2g) | (3g), (3i), (3j), (3k) | (4b) | (5d) | (6d) | — | (7s), (7w) | (7dd) |
| 127 | (1d) | (2g) | (3g), (3i), (3j), (3k) | (4b) | (5e) | (6a) | (7a) | — | — |
| 128 | (1d) | (2g) | (3g), (3i), (3j), (3k) | (4b) | (5e) | (6a) | (7b), (7g) | — | — |
| 129 | (1d) | (2g) | (3g), (3i), (3j), (3k) | (4b) | (5e) | (6c) | (7a) | — | (7dd) |
| 130 | (1d) | (2g) | (3g), (3i), (3j), (3k) | (4b) | (5e) | (6c) | (7b), (7g) | — | (7dd) |
| 131 | (1d) | (2g) | (3g), (3i), (3j), (3k) | (4b) | (5e) | (6d) | — | (7r) | (7dd) |
| 132 | (1d) | (2g) | (3g), (3i), (3j), (3k) | (4b) | (5e) | (6d) | — | (7s), (7w) | (7dd) |
| 133 | (1d) | (2g) | (3g), (3i), (3j), (3k) | (4c) | (5d) | (6a) | (7a) | — | — |
| 134 | (1d) | (2g) | (3g), (3i), (3j), (3k) | (4c) | (5d) | (6a) | (7b), (7g) | — | — |
| 135 | (1d) | (2g) | (3g), (3i), (3j), (3k) | (4c) | (5d) | (6c) | (7a) | — | (7dd) |
| 136 | (1d) | (2g) | (3g), (3i), (3j), (3k) | (4c) | (5d) | (6c) | (7b), (7g) | — | (7dd) |
| 137 | (1d) | (2g) | (3g), (3i), (3j), (3k) | (4c) | (5d) | (6d) | — | (7r) | (7dd) |
| 138 | (1d) | (2g) | (3g), (3i), (3j), (3k) | (4c) | (5d) | (6d) | — | (7s), (7w) | (7dd) |
| 139 | (1d) | (2g) | (3g), (3i), (3j), (3k) | (4c) | (5e) | (6a) | (7a) | — | — |
| 140 | (1d) | (2g) | (3g), (3i), (3j), (3k) | (4c) | (5e) | (6a) | (7b), (7g) | — | — |
| 141 | (1d) | (2g) | (3g), (3i), (3j), (3k) | (4c) | (5e) | (6c) | (7a) | — | (7dd) |
| 142 | (1d) | (2g) | (3g), (3i), (3j), (3k) | (4c) | (5e) | (6c) | (7b), (7g) | — | (7dd) |
| 143 | (1d) | (2g) | (3g), (3i), (3j), (3k) | (4c) | (5e) | (6d) | — | (7r) | (7dd) |
| 144 | (1d) | (2g) | (3g), (3i), (3j), (3k) | (4c) | (5e) | (6d) | — | (7s), (7w) | (7dd) |
| 145 | (1e) | (2c) | (3a) | (4b) | (5d) | (6a) | (7a) | — | — |
| 146 | (1e) | (2c) | (3a) | (4b) | (5d) | (6a) | (7b), (7g) | — | — |
| 147 | (1e) | (2c) | (3a) | (4b) | (5d) | (6c) | (7a) | — | (7dd) |
| 148 | (1e) | (2c) | (3a) | (4b) | (5d) | (6c) | (7b), (7g) | — | (7dd) |
| 149 | (1e) | (2c) | (3a) | (4b) | (5d) | (6d) | — | (7r) | (7dd) |
| 150 | (1e) | (2c) | (3a) | (4b) | (5d) | (6d) | — | (7s), (7w) | (7dd) |
| 151 | (1e) | (2c) | (3a) | (4b) | (5e) | (6a) | (7a) | — | — |
| 152 | (1e) | (2c) | (3a) | (4b) | (5e) | (6a) | (7b), (7g) | — | — |
| 153 | (1e) | (2c) | (3a) | (4b) | (5e) | (6c) | (7a) | — | (7dd) |
| 154 | (1e) | (2c) | (3a) | (4b) | (5e) | (6c) | (7b), (7g) | — | (7dd) |
| 155 | (1e) | (2c) | (3a) | (4b) | (5e) | (6d) | — | (7r) | (7dd) |
| 156 | (1e) | (2c) | (3a) | (4b) | (5e) | (6d) | — | (7s), (7w) | (7dd) |
| 157 | (1e) | (2c) | (3a) | (4c) | (5d) | (6a) | (7a) | — | — |
| 158 | (1e) | (2c) | (3a) | (4c) | (5d) | (6a) | (7b), (7g) | — | — |
| 159 | (1e) | (2c) | (3a) | (4c) | (5d) | (6c) | (7a) | — | (7dd) |
| 160 | (1e) | (2c) | (3a) | (4c) | (5d) | (6c) | (7b), (7g) | — | (7dd) |
| 161 | (1e) | (2c) | (3a) | (4c) | (5d) | (6d) | — | (7r) | (7dd) |
| 162 | (1e) | (2c) | (3a) | (4c) | (5d) | (6d) | — | (7s), (7w) | (7dd) |
| 163 | (1e) | (2c) | (3a) | (4c) | (5e) | (6a) | (7a) | — | — |
| 164 | (1e) | (2c) | (3a) | (4c) | (5e) | (6a) | (7b), (7g) | — | — |
| 165 | (1e) | (2c) | (3a) | (4c) | (5e) | (6c) | (7a) | — | (7dd) |
| 166 | (1e) | (2c) | (3a) | (4c) | (5e) | (6c) | (7b), (7g) | — | (7dd) |
| 167 | (1e) | (2c) | (3a) | (4c) | (5e) | (6d) | — | (7r) | (7dd) |
| 168 | (1e) | (2c) | (3a) | (4c) | (5e) | (6d) | — | (7s), (7w) | (7dd) |
| 169 | (1e) | (2c) | (3d) | (4b) | (5d) | (6a) | (7a) | — | — |
| 170 | (1e) | (2c) | (3d) | (4b) | (5d) | (6a) | (7b), (7g) | — | — |
| 171 | (1e) | (2c) | (3d) | (4b) | (5d) | (6c) | (7a) | — | (7dd) |
| 172 | (1e) | (2c) | (3d) | (4b) | (5d) | (6c) | (7b), (7g) | — | (7dd) |
| 173 | (1e) | (2c) | (3d) | (4b) | (5d) | (6d) | — | (7r) | (7dd) |

-continued

| Embodiment | R¹ | R² | R³ | R⁵ | R⁶ | R⁴ | R⁴ᵃ | R⁴ᵇ | R⁴ᶜ |
|---|---|---|---|---|---|---|---|---|---|
| 174 | (1e) | (2c) | (3d) | (4b) | (5d) | (6d) | — | (7s), (7w) | (7dd) |
| 175 | (1e) | (2c) | (3d) | (4b) | (5e) | (6a) | (7a) | — | — |
| 176 | (1e) | (2c) | (3d) | (4b) | (5e) | (6a) | (7b), (7g) | — | — |
| 177 | (1e) | (2c) | (3d) | (4b) | (5e) | (6c) | (7a) | — | (7dd) |
| 178 | (1e) | (2c) | (3d) | (4b) | (5e) | (6c) | (7b), (7g) | — | (7dd) |
| 179 | (1e) | (2c) | (3d) | (4b) | (5e) | (6d) | — | (7r) | (7dd) |
| 180 | (1e) | (2c) | (3d) | (4b) | (5e) | (6d) | — | (7s), (7w) | (7dd) |
| 181 | (1e) | (2c) | (3d) | (4c) | (5d) | (6a) | (7a) | — | — |
| 182 | (1e) | (2c) | (3d) | (4c) | (5d) | (6a) | (7b), (7g) | — | — |
| 183 | (1e) | (2c) | (3d) | (4c) | (5d) | (6c) | (7a) | — | (7dd) |
| 184 | (1e) | (2c) | (3d) | (4c) | (5d) | (6c) | (7b), (7g) | — | (7dd) |
| 185 | (1e) | (2c) | (3d) | (4c) | (5d) | (6d) | — | (7r) | (7dd) |
| 186 | (1e) | (2c) | (3d) | (4c) | (5d) | (6d) | — | (7s), (7w) | (7dd) |
| 187 | (1e) | (2c) | (3d) | (4c) | (5e) | (6a) | (7a) | — | — |
| 188 | (1e) | (2c) | (3d) | (4c) | (5e) | (6a) | (7b), (7g) | — | — |
| 189 | (1e) | (2c) | (3d) | (4c) | (5e) | (6c) | (7a) | — | (7dd) |
| 190 | (1e) | (2c) | (3d) | (4c) | (5e) | (6c) | (7b), (7g) | — | (7dd) |
| 191 | (1e) | (2c) | (3d) | (4c) | (5e) | (6d) | — | (7r) | (7dd) |
| 192 | (1e) | (2c) | (3d) | (4c) | (5e) | (6d) | — | (7s), (7w) | (7dd) |
| 193 | (1e) | (2c) | (3g), (3i), (3j), (3k) | (4b) | (5d) | (6a) | (7a) | — | — |
| 194 | (1e) | (2c) | (3g), (3i), (3j), (3k) | (4b) | (5d) | (6a) | (7b), (7g) | — | — |
| 195 | (1e) | (2c) | (3g), (3i), (3j), (3k) | (4b) | (5d) | (6c) | (7a) | — | (7dd) |
| 196 | (1e) | (2c) | (3g), (3i), (3j), (3k) | (4b) | (5d) | (6c) | (7b), (7g) | — | (7dd) |
| 197 | (1e) | (2c) | (3g), (3i), (3j), (3k) | (4b) | (5d) | (6d) | — | (7r) | (7dd) |
| 198 | (1e) | (2c) | (3g), (3i), (3j), (3k) | (4b) | (5d) | (6d) | — | (7s), (7w) | (7dd) |
| 199 | (1e) | (2c) | (3g), (3i), (3j), (3k) | (4b) | (5e) | (6a) | (7a) | — | — |
| 200 | (1e) | (2c) | (3g), (3i), (3j), (3k) | (4b) | (5e) | (6a) | (7b), (7g) | — | — |
| 201 | (1e) | (2c) | (3g), (3i), (3j), (3k) | (4b) | (5e) | (6c) | (7a) | — | (7dd) |
| 202 | (1e) | (2c) | (3g), (3i), (3j), (3k) | (4b) | (5e) | (6c) | (7b), (7g) | — | (7dd) |
| 203 | (1e) | (2c) | (3g), (3i), (3j), (3k) | (4b) | (5e) | (6d) | — | (7r) | (7dd) |
| 204 | (1e) | (2c) | (3g), (3i), (3j), (3k) | (4b) | (5e) | (6d) | — | (7s), (7w) | (7dd) |
| 205 | (1e) | (2c) | (3g), (3i), (3j), (3k) | (4c) | (5d) | (6a) | (7a) | — | — |
| 206 | (1e) | (2c) | (3g), (3i), (3j), (3k) | (4c) | (5d) | (6a) | (7b), (7g) | — | — |
| 207 | (1e) | (2c) | (3g), (3i), (3j), (3k) | (4c) | (5d) | (6c) | (7a) | — | (7dd) |
| 208 | (1e) | (2c) | (3g), (3i), (3j), (3k) | (4c) | (5d) | (6c) | (7b), (7g) | — | (7dd) |
| 209 | (1e) | (2c) | (3g), (3i), (3j), (3k) | (4c) | (5d) | (6d) | — | (7r) | (7dd) |
| 210 | (1e) | (2c) | (3g), (3i), (3j), (3k) | (4c) | (5d) | (6d) | — | (7s), (7w) | (7dd) |
| 211 | (1e) | (2c) | (3g), (3i), (3j), (3k) | (4c) | (5e) | (6a) | (7a) | — | — |
| 212 | (1e) | (2c) | (3g), (3i), (3j), (3k) | (4c) | (5e) | (6a) | (7b), (7g) | — | — |
| 213 | (1e) | (2c) | (3g), (3i), (3j), (3k) | (4c) | (5e) | (6c) | (7a) | — | (7dd) |
| 214 | (1e) | (2c) | (3g), (3i), (3j), (3k) | (4c) | (5e) | (6c) | (7b), (7g) | — | (7dd) |
| 215 | (1e) | (2c) | (3g), (3i), (3j), (3k) | (4c) | (5e) | (6d) | — | (7r) | (7dd) |
| 216 | (1e) | (2c) | (3g), (3i), (3j), (3k) | (4c) | (5e) | (6d) | — | (7s), (7w) | (7dd) |
| 217 | (1e) | (2g) | (3a) | (4b) | (5d) | (6a) | (7a) | — | — |
| 218 | (1e) | (2g) | (3a) | (4b) | (5d) | (6a) | (7b), (7g) | — | — |
| 219 | (1e) | (2g) | (3a) | (4b) | (5d) | (6c) | (7a) | — | (7dd) |
| 220 | (1e) | (2g) | (3a) | (4b) | (5d) | (6c) | (7b), (7g) | — | (7dd) |
| 221 | (1e) | (2g) | (3a) | (4b) | (5d) | (6d) | — | (7r) | (7dd) |
| 222 | (1e) | (2g) | (3a) | (4b) | (5d) | (6d) | — | (7s), (7w) | (7dd) |
| 223 | (1e) | (2g) | (3a) | (4b) | (5e) | (6a) | (7a) | — | — |
| 224 | (1e) | (2g) | (3a) | (4b) | (5e) | (6a) | (7b), (7g) | — | — |
| 225 | (1e) | (2g) | (3a) | (4b) | (5e) | (6c) | (7a) | — | (7dd) |
| 226 | (1e) | (2g) | (3a) | (4b) | (5e) | (6c) | (7b), (7g) | — | (7dd) |

-continued

| Embodiment | R¹ | R² | R³ | R⁵ | R⁶ | R⁴ | R⁴ᵃ | R⁴ᵇ | R⁴ᶜ |
|---|---|---|---|---|---|---|---|---|---|
| 227 | (1e) | (2g) | (3a) | (4b) | (5e) | (6d) | — | (7r) | (7dd) |
| 228 | (1e) | (2g) | (3a) | (4b) | (5e) | (6d) | — | (7s), (7w) | (7dd) |
| 229 | (1e) | (2g) | (3a) | (4c) | (5d) | (6a) | (7a) | — | — |
| 230 | (1e) | (2g) | (3a) | (4c) | (5d) | (6a) | (7b), (7g) | — | — |
| 231 | (1e) | (2g) | (3a) | (4c) | (5d) | (6c) | (7a) | — | (7dd) |
| 232 | (1e) | (2g) | (3a) | (4c) | (5d) | (6c) | (7b), (7g) | — | (7dd) |
| 233 | (1e) | (2g) | (3a) | (4c) | (5d) | (6d) | — | (7r) | (7dd) |
| 234 | (1e) | (2g) | (3a) | (4c) | (5d) | (6d) | — | (7s), (7w) | (7dd) |
| 235 | (1e) | (2g) | (3a) | (4c) | (5e) | (6a) | (7a) | — | — |
| 236 | (1e) | (2g) | (3a) | (4c) | (5e) | (6a) | (7b), (7g) | — | — |
| 237 | (1e) | (2g) | (3a) | (4c) | (5e) | (6c) | (7a) | — | (7dd) |
| 238 | (1e) | (2g) | (3a) | (4c) | (5e) | (6c) | (7b), (7g) | — | (7dd) |
| 239 | (1e) | (2g) | (3a) | (4c) | (5e) | (6d) | — | (7r) | (7dd) |
| 240 | (1e) | (2g) | (3a) | (4c) | (5e) | (6d) | — | (7s), (7w) | (7dd) |
| 241 | (1e) | (2g) | (3d) | (4b) | (5d) | (6a) | (7a) | — | — |
| 242 | (1e) | (2g) | (3d) | (4b) | (5d) | (6a) | (7b), (7g) | — | — |
| 243 | (1e) | (2g) | (3d) | (4b) | (5d) | (6c) | (7a) | — | (7dd) |
| 244 | (1e) | (2g) | (3d) | (4b) | (5d) | (6c) | (7b), (7g) | — | (7dd) |
| 245 | (1e) | (2g) | (3d) | (4b) | (5d) | (6d) | — | (7r) | (7dd) |
| 246 | (1e) | (2g) | (3d) | (4b) | (5d) | (6d) | — | (7s), (7w) | (7dd) |
| 247 | (1e) | (2g) | (3d) | (4b) | (5e) | (6a) | (7a) | — | — |
| 248 | (1e) | (2g) | (3d) | (4b) | (5e) | (6a) | (7b), (7g) | — | — |
| 249 | (1e) | (2g) | (3d) | (4b) | (5e) | (6c) | (7a) | — | (7dd) |
| 250 | (1e) | (2g) | (3d) | (4b) | (5e) | (6c) | (7b), (7g) | — | (7dd) |
| 251 | (1e) | (2g) | (3d) | (4b) | (5e) | (6d) | — | (7r) | (7dd) |
| 252 | (1e) | (2g) | (3d) | (4b) | (5e) | (6d) | — | (7s), (7w) | (7dd) |
| 253 | (1e) | (2g) | (3d) | (4c) | (5d) | (6a) | (7a) | — | — |
| 254 | (1e) | (2g) | (3d) | (4c) | (5d) | (6a) | (7b), (7g) | — | — |
| 255 | (1e) | (2g) | (3d) | (4c) | (5d) | (6c) | (7a) | — | (7dd) |
| 256 | (1e) | (2g) | (3d) | (4c) | (5d) | (6c) | (7b), (7g) | — | (7dd) |
| 257 | (1e) | (2g) | (3d) | (4c) | (5d) | (6d) | — | (7r) | (7dd) |
| 258 | (1e) | (2g) | (3d) | (4c) | (5d) | (6d) | — | (7s), (7w) | (7dd) |
| 259 | (1e) | (2g) | (3d) | (4c) | (5e) | (6a) | (7a) | — | — |
| 260 | (1e) | (2g) | (3d) | (4c) | (5e) | (6a) | (7b), (7g) | — | — |
| 261 | (1e) | (2g) | (3d) | (4c) | (5e) | (6c) | (7a) | — | (7dd) |
| 262 | (1e) | (2g) | (3d) | (4c) | (5e) | (6c) | (7b), (7g) | — | (7dd) |
| 263 | (1e) | (2g) | (3d) | (4c) | (5e) | (6d) | — | (7r) | (7dd) |
| 264 | (1e) | (2g) | (3d) | (4c) | (5e) | (6d) | — | (7s), (7w) | (7dd) |
| 265 | (1e) | (2g) | (3g), (3i), (3j), (3k) | (4b) | (5d) | (6a) | (7a) | — | — |
| 266 | (1e) | (2g) | (3g), (3i), (3j), (3k) | (4b) | (5d) | (6a) | (7b), (7g) | — | — |
| 267 | (1e) | (2g) | (3g), (3i), (3j), (3k) | (4b) | (5d) | (6c) | (7a) | — | (7dd) |
| 268 | (1e) | (2g) | (3g), (3i), (3j), (3k) | (4b) | (5d) | (6c) | (7b), (7g) | — | (7dd) |
| 269 | (1e) | (2g) | (3g), (3i), (3j), (3k) | (4b) | (5d) | (6d) | — | (7r) | (7dd) |
| 270 | (1e) | (2g) | (3g), (3i), (3j), (3k) | (4b) | (5d) | (6d) | — | (7s), (7w) | (7dd) |
| 271 | (1e) | (2g) | (3g), (3i), (3j), (3k) | (4b) | (5e) | (6a) | (7a) | — | — |
| 272 | (1e) | (2g) | (3g), (3i), (3j), (3k) | (4b) | (5e) | (6a) | (7b), (7g) | — | — |
| 273 | (1e) | (2g) | (3g), (3i), (3j), (3k) | (4b) | (5e) | (6c) | (7a) | — | (7dd) |
| 274 | (1e) | (2g) | (3g), (3i), (3j), (3k) | (4b) | (5e) | (6c) | (7b), (7g) | — | (7dd) |
| 275 | (1e) | (2g) | (3g), (3i), (3j), (3k) | (4b) | (5e) | (6d) | — | (7r) | (7dd) |
| 276 | (1e) | (2g) | (3g), (3i), (3j), (3k) | (4b) | (5e) | (6d) | — | (7s), (7w) | (7dd) |
| 277 | (1e) | (2g) | (3g), (3i), (3j), (3k) | (4c) | (5d) | (6a) | (7a) | — | — |
| 278 | (1e) | (2g) | (3g), (3i), (3j), (3k) | (4c) | (5d) | (6a) | (7b), (7g) | — | — |
| 279 | (1e) | (2g) | (3g), (3i), (3j), (3k) | (4c) | (5d) | (6c) | (7a) | — | (7dd) |
| 280 | (1e) | (2g) | (3g), (3i), (3j), (3k) | (4c) | (5d) | (6c) | (7b), (7g) | — | (7dd) |
| 281 | (1e) | (2g) | (3g), (3i), (3j), (3k) | (4c) | (5d) | (6d) | — | (7r) | (7dd) |
| 282 | (1e) | (2g) | (3g), (3i), (3j), (3k) | (4c) | (5d) | (6d) | — | (7s), (7w) | (7dd) |
| 283 | (1e) | (2g) | (3g), (3i), (3j), (3k) | (4c) | (5e) | (6a) | (7a) | — | — |

-continued

| Embodiment | R¹ | R² | R³ | R⁵ | R⁶ | R⁴ | R⁴ᵃ | R⁴ᵇ | R⁴ᶜ |
|---|---|---|---|---|---|---|---|---|---|
| 284 | (1e) | (2g) | (3g), (3i), (3j), (3k) | (4c) | (5e) | (6a) | (7b), (7g) | — | — |
| 285 | (1e) | (2g) | (3g), (3i), (3j), (3k) | (4c) | (5e) | (6c) | (7a) | — | (7dd) |
| 286 | (1e) | (2g) | (3g), (3i), (3j), (3k) | (4c) | (5e) | (6c) | (7b), (7g) | — | (7dd) |
| 287 | (1e) | (2g) | (3g), (3i), (3j), (3k) | (4c) | (5e) | (6d) | — | (7r) | (7dd) |
| 288 | (1e) | (2g) | (3g), (3i), (3j), (3k) | (4c) | (5e) | (6d) | — | (7s), (7w) | (7dd) |
| 289 | (1i) | (2c) | (3a) | (4b) | (5d) | (6a) | (7a) | — | — |
| 290 | (1i) | (2c) | (3a) | (4b) | (5d) | (6a) | (7b), (7g) | — | — |
| 291 | (1i) | (2c) | (3a) | (4b) | (5d) | (6c) | (7a) | — | (7dd) |
| 292 | (1i) | (2c) | (3a) | (4b) | (5d) | (6c) | (7b), (7g) | — | (7dd) |
| 293 | (1i) | (2c) | (3a) | (4b) | (5d) | (6d) | — | (7r) | (7dd) |
| 294 | (1i) | (2c) | (3a) | (4b) | (5d) | (6d) | — | (7s), (7w) | (7dd) |
| 295 | (1i) | (2c) | (3a) | (4b) | (5e) | (6a) | (7a) | — | — |
| 296 | (1i) | (2c) | (3a) | (4b) | (5e) | (6a) | (7b), (7g) | — | — |
| 297 | (1i) | (2c) | (3a) | (4b) | (5e) | (6c) | (7a) | — | (7dd) |
| 298 | (1i) | (2c) | (3a) | (4b) | (5e) | (6c) | (7b), (7g) | — | (7dd) |
| 299 | (1i) | (2c) | (3a) | (4b) | (5e) | (6d) | — | (7r) | (7dd) |
| 300 | (1i) | (2c) | (3a) | (4b) | (5e) | (6d) | — | (7s), (7w) | (7dd) |
| 301 | (1i) | (2c) | (3a) | (4c) | (5d) | (6a) | (7a) | — | — |
| 302 | (1i) | (2c) | (3a) | (4c) | (5d) | (6a) | (7b), (7g) | — | — |
| 303 | (1i) | (2c) | (3a) | (4c) | (5d) | (6c) | (7a) | — | (7dd) |
| 304 | (1i) | (2c) | (3a) | (4c) | (5d) | (6c) | (7b), (7g) | — | (7dd) |
| 305 | (1i) | (2c) | (3a) | (4c) | (5d) | (6d) | — | (7r) | (7dd) |
| 306 | (1i) | (2c) | (3a) | (4c) | (5d) | (6d) | — | (7s), (7w) | (7dd) |
| 307 | (1i) | (2c) | (3a) | (4c) | (5e) | (6a) | (7a) | — | — |
| 308 | (1i) | (2c) | (3a) | (4c) | (5e) | (6a) | (7b), (7g) | — | — |
| 309 | (1i) | (2c) | (3a) | (4c) | (5e) | (6c) | (7a) | — | (7dd) |
| 310 | (1i) | (2c) | (3a) | (4c) | (5e) | (6c) | (7b), (7g) | — | (7dd) |
| 311 | (1i) | (2c) | (3a) | (4c) | (5e) | (6d) | — | (7r) | (7dd) |
| 312 | (1i) | (2c) | (3a) | (4c) | (5e) | (6d) | — | (7s), (7w) | (7dd) |
| 313 | (1i) | (2c) | (3d) | (4b) | (5d) | (6a) | (7a) | — | — |
| 314 | (1i) | (2c) | (3d) | (4b) | (5d) | (6a) | (7b), (7g) | — | — |
| 315 | (1i) | (2c) | (3d) | (4b) | (5d) | (6c) | (7a) | — | (7dd) |
| 316 | (1i) | (2c) | (3d) | (4b) | (5d) | (6c) | (7b), (7g) | — | (7dd) |
| 317 | (1i) | (2c) | (3d) | (4b) | (5d) | (6d) | — | (7r) | (7dd) |
| 318 | (1i) | (2c) | (3d) | (4b) | (5d) | (6d) | — | (7s), (7w) | (7dd) |
| 319 | (1i) | (2c) | (3d) | (4b) | (5e) | (6a) | (7a) | — | — |
| 320 | (1i) | (2c) | (3d) | (4b) | (5e) | (6a) | (7b), (7g) | — | — |
| 321 | (1i) | (2c) | (3d) | (4b) | (5e) | (6c) | (7a) | — | (7dd) |
| 322 | (1i) | (2c) | (3d) | (4b) | (5e) | (6c) | (7b), (7g) | — | (7dd) |
| 323 | (1i) | (2c) | (3d) | (4b) | (5e) | (6d) | — | (7r) | (7dd) |
| 324 | (1i) | (2c) | (3d) | (4b) | (5e) | (6d) | — | (7s), (7w) | (7dd) |
| 325 | (1i) | (2c) | (3d) | (4c) | (5d) | (6a) | (7a) | — | — |
| 326 | (1i) | (2c) | (3d) | (4c) | (5d) | (6a) | (7b), (7g) | — | — |
| 327 | (1i) | (2c) | (3d) | (4c) | (5d) | (6c) | (7a) | — | (7dd) |
| 328 | (1i) | (2c) | (3d) | (4c) | (5d) | (6c) | (7b), (7g) | — | (7dd) |
| 329 | (1i) | (2c) | (3d) | (4c) | (5d) | (6d) | — | (7r) | (7dd) |
| 330 | (1i) | (2c) | (3d) | (4c) | (5d) | (6d) | — | (7s), (7w) | (7dd) |
| 331 | (1i) | (2c) | (3d) | (4c) | (5e) | (6a) | (7a) | — | — |
| 332 | (1i) | (2c) | (3d) | (4c) | (5e) | (6a) | (7b), (7g) | — | — |
| 333 | (1i) | (2c) | (3d) | (4c) | (5e) | (6c) | (7a) | — | (7dd) |
| 334 | (1i) | (2c) | (3d) | (4c) | (5e) | (6c) | (7b), (7g) | — | (7dd) |
| 335 | (1i) | (2c) | (3d) | (4c) | (5e) | (6d) | — | (7r) | (7dd) |
| 336 | (1i) | (2c) | (3d) | (4c) | (5e) | (6d) | — | (7s), (7w) | (7dd) |
| 337 | (1i) | (2c) | (3g), (3i), (3j), (3k) | (4b) | (5d) | (6a) | (7a) | — | — |
| 338 | (1i) | (2c) | (3g), (3i), (3j), (3k) | (4b) | (5d) | (6a) | (7b), (7g) | — | — |
| 339 | (1i) | (2c) | (3g), (3i), (3j), (3k) | (4b) | (5d) | (6c) | (7a) | — | (7dd) |
| 340 | (1i) | (2c) | (3g), (3i), (3j), (3k) | (4b) | (5d) | (6c) | (7b), (7g) | — | (7dd) |
| 341 | (1i) | (2c) | (3g), (3i), (3j), (3k) | (4b) | (5d) | (6d) | — | (7r) | (7dd) |
| 342 | (1i) | (2c) | (3g), (3i), (3j), (3k) | (4b) | (5d) | (6d) | — | (7s), (7w) | (7dd) |
| 343 | (1i) | (2c) | (3g), (3i), (3j), (3k) | (4b) | (5e) | (6a) | (7a) | — | — |
| 344 | (1i) | (2c) | (3g), (3i), (3j), (3k) | (4b) | (5e) | (6a) | (7b), (7g) | — | — |
| 345 | (1i) | (2c) | (3g), (3i), (3j), (3k) | (4b) | (5e) | (6c) | (7a) | — | (7dd) |

-continued

| Embodiment | R$^1$ | R$^2$ | R$^3$ | R$^5$ | R$^6$ | R$^4$ | R$^{4a}$ | R$^{4b}$ | R$^{4c}$ |
|---|---|---|---|---|---|---|---|---|---|
| 346 | (1i) | (2c) | (3g), (3i), (3j), (3k) | (4b) | (5e) | (6c) | (7b), (7g) | — | (7dd) |
| 347 | (1i) | (2c) | (3g), (3i), (3j), (3k) | (4b) | (5e) | (6d) | — | (7r) | (7dd) |
| 348 | (1i) | (2c) | (3g), (3i), (3j), (3k) | (4b) | (5e) | (6d) | — | (7s), (7w) | (7dd) |
| 349 | (1i) | (2c) | (3g), (3i), (3j), (3k) | (4c) | (5d) | (6a) | (7a) | — | — |
| 350 | (1i) | (2c) | (3g), (3i), (3j), (3k) | (4c) | (5d) | (6a) | (7b), (7g) | — | — |
| 351 | (1i) | (2c) | (3g), (3i), (3j), (3k) | (4c) | (5d) | (6c) | (7a) | — | (7dd) |
| 352 | (1i) | (2c) | (3g), (3i), (3j), (3k) | (4c) | (5d) | (6c) | (7b), (7g) | — | (7dd) |
| 353 | (1i) | (2c) | (3g), (3i), (3j), (3k) | (4c) | (5d) | (6d) | — | (7r) | (7dd) |
| 354 | (1i) | (2c) | (3g), (3i), (3j), (3k) | (4c) | (5d) | (6d) | — | (7s), (7w) | (7dd) |
| 355 | (1i) | (2c) | (3g), (3i), (3j), (3k) | (4c) | (5e) | (6a) | (7a) | — | — |
| 356 | (1i) | (2c) | (3g), (3i), (3j), (3k) | (4c) | (5e) | (6a) | (7b), (7g) | — | — |
| 357 | (1i) | (2c) | (3g), (3i), (3j), (3k) | (4c) | (5e) | (6c) | (7a) | — | (7dd) |
| 358 | (1i) | (2c) | (3g), (3i), (3j), (3k) | (4c) | (5e) | (6c) | (7b), (7g) | — | (7dd) |
| 359 | (1i) | (2c) | (3g), (3i), (3j), (3k) | (4c) | (5e) | (6d) | — | (7r) | (7dd) |
| 360 | (1i) | (2c) | (3g), (3i), (3j), (3k) | (4c) | (5e) | (6d) | — | (7s), (7w) | (7dd) |
| 361 | (1i) | (2g) | (3a) | (4b) | (5d) | (6a) | (7a) | — | — |
| 362 | (1i) | (2g) | (3a) | (4b) | (5d) | (6a) | (7b), (7g) | — | — |
| 363 | (1i) | (2g) | (3a) | (4b) | (5d) | (6c) | (7a) | — | (7dd) |
| 364 | (1i) | (2g) | (3a) | (4b) | (5d) | (6c) | (7b), (7g) | — | (7dd) |
| 365 | (1i) | (2g) | (3a) | (4b) | (5d) | (6d) | — | (7r) | (7dd) |
| 366 | (1i) | (2g) | (3a) | (4b) | (5d) | (6d) | — | (7s), (7w) | (7dd) |
| 367 | (1i) | (2g) | (3a) | (4b) | (5e) | (6a) | (7a) | — | — |
| 368 | (1i) | (2g) | (3a) | (4b) | (5e) | (6a) | (7b), (7g) | — | — |
| 369 | (1i) | (2g) | (3a) | (4b) | (5e) | (6c) | (7a) | — | (7dd) |
| 370 | (1i) | (2g) | (3a) | (4b) | (5e) | (6c) | (7b), (7g) | — | (7dd) |
| 371 | (1i) | (2g) | (3a) | (4b) | (5e) | (6d) | — | (7r) | (7dd) |
| 372 | (1i) | (2g) | (3a) | (4b) | (5e) | (6d) | — | (7s), (7w) | (7dd) |
| 373 | (1i) | (2g) | (3a) | (4c) | (5d) | (6a) | (7a) | — | — |
| 374 | (1i) | (2g) | (3a) | (4c) | (5d) | (6a | (7b), (7g) | — | — |
| 375 | (1i) | (2g) | (3a) | (4c) | (5d) | (6c) | (7a) | — | (7dd) |
| 376 | (1i) | (2g) | (3a) | (4c) | (5d) | (6c) | (7b), (7g) | — | (7dd) |
| 377 | (1i) | (2g) | (3a) | (4c) | (5d) | (6d) | — | (7r) | (7dd) |
| 378 | (1i) | (2g) | (3a) | (4c) | (5d) | (6d) | — | (7s), (7w) | (7dd) |
| 379 | (1i) | (2g) | (3a) | (4c) | (5e) | (6a) | (7a) | — | — |
| 380 | (1i) | (2g) | (3a) | (4c) | (5e) | (6a) | (7b), (7g) | — | — |
| 381 | (1i) | (2g) | (3a) | (4c) | (5e) | (6c) | (7a) | — | (7dd) |
| 382 | (1i) | (2g) | (3a) | (4c) | (5e) | (6c) | (7b), (7g) | — | (7dd) |
| 383 | (1i) | (2g) | (3a) | (4c) | (5e) | (6d) | — | (7r) | (7dd) |
| 384 | (1i) | (2g) | (3a) | (4c) | (5e) | (6d) | — | (7s), (7w) | (7dd) |
| 385 | (1i) | (2g) | (3d) | (4b) | (5d) | (6a) | (7a) | — | — |
| 386 | (1i) | (2g) | (3d) | (4b) | (5d) | (6a) | (7b), (7g) | — | — |
| 387 | (1i) | (2g) | (3d) | (4b) | (5d) | (6c) | (7a) | — | (7dd) |
| 388 | (1i) | (2g) | (3d) | (4b) | (5d) | (6c) | (7b), (7g) | — | (7dd) |
| 389 | (1i) | (2g) | (3d) | (4b) | (5d) | (6d) | — | (7r) | (7dd) |
| 390 | (1i) | (2g) | (3d) | (4b) | (5d) | (6d) | — | (7s), (7w) | (7dd) |
| 391 | (1i) | (2g) | (3d) | (4b) | (5e) | (6a) | (7a) | — | — |
| 392 | (1i) | (2g) | (3d) | (4b) | (5e) | (6a) | (7b), (7g) | — | — |
| 393 | (1i) | (2g) | (3d) | (4b) | (5e) | (6c) | (7a) | — | (7dd) |
| 394 | (1i) | (2g) | (3d) | (4b) | (5e) | (6c) | (7b), (7g) | — | (7dd) |
| 395 | (1i) | (2g) | (3d) | (4b) | (5e) | (6d) | — | (7r) | (7dd) |
| 396 | (1i) | (2g) | (3d) | (4b) | (5e) | (6d) | — | (7s), (7w) | (7dd) |
| 397 | (1i) | (2g) | (3d) | (4c) | (5d) | (6a) | (7a) | — | — |
| 398 | (1i) | (2g) | (3d) | (4c) | (5d) | (6a) | (7b), (7g) | — | — |
| 399 | (1i) | (2g) | (3d) | (4c) | (5d) | (6c) | (7a) | — | (7dd) |
| 400 | (1i) | (2g) | (3d) | (4c) | (5d) | (6c) | (7b), (7g) | — | (7dd) |
| 401 | (1i) | (2g) | (3d) | (4c) | (5d) | (6d) | — | (7r) | (7dd) |
| 402 | (1i) | (2g) | (3d) | (4c) | (5d) | (6d) | — | (7s), (7w) | (7dd) |
| 403 | (1i) | (2g) | (3d) | (4c) | (5e) | (6a) | (7a) | — | — |
| 404 | (1i) | (2g) | (3d) | (4c) | (5e) | (6a) | (7b), (7g) | — | — |
| 405 | (1i) | (2g) | (3d) | (4c) | (5e) | (6c) | (7a) | — | (7dd) |
| 406 | (1i) | (2g) | (3d) | (4c) | (5e) | (6c) | (7b), (7g) | — | (7dd) |
| 407 | (1i) | (2g) | (3d) | (4c) | (5e) | (6d) | — | (7r) | (7dd) |

-continued

| Embodiment | R¹ | R² | R³ | R⁵ | R⁶ | R⁴ | R⁴ᵃ | R⁴ᵇ | R⁴ᶜ |
|---|---|---|---|---|---|---|---|---|---|
| 408 | (1i) | (2g) | (3d) | (4c) | (5e) | (6d) | — | (7s), (7w) | (7dd) |
| 409 | (1i) | (2g) | (3g), (3i), (3j), (3k) | (4b) | (5d) | (6a) | (7a) | — | — |
| 410 | (1i) | (2g) | (3g), (3i), (3j), (3k) | (4b) | (5d) | (6a) | (7b), (7g) | — | — |
| 411 | (1i) | (2g) | (3g), (3i), (3j), (3k) | (4b) | (5d) | (6c) | (7a) | — | (7dd) |
| 412 | (1i) | (2g) | (3g), (3i), (3j), (3k) | (4b) | (5d) | (6c) | (7b), (7g) | — | (7dd) |
| 413 | (1i) | (2g) | (3g), (3i), (3j), (3k) | (4b) | (5d) | (6d) | — | (7r) | (7dd) |
| 414 | (1i) | (2g) | (3g), (3i), (3j), (3k) | (4b) | (5d) | (6d) | — | (7s), (7w) | (7dd) |
| 415 | (1i) | (2g) | (3g), (3i), (3j), (3k) | (4b) | (5e) | (6a) | (7a) | — | — |
| 416 | (1i) | (2g) | (3g), (3i), (3j), (3k) | (4b) | (5e) | (6a) | (7b), (7g) | — | — |
| 417 | (1i) | (2g) | (3g), (3i), (3j), (3k) | (4b) | (5e) | (6c) | (7a) | — | (7dd) |
| 418 | (1i) | (2g) | (3g), (3i), (3j), (3k) | (4b) | (5e) | (6c) | (7b), (7g) | — | (7dd) |
| 419 | (1i) | (2g) | (3g), (3i), (3j), (3k) | (4b) | (5e) | (6d) | — | (7r) | (7dd) |
| 420 | (1i) | (2g) | (3g), (3i), (3j), (3k) | (4b) | (5e) | (6d) | — | (7s), (7w) | (7dd) |
| 421 | (1i) | (2g) | (3g), (3i), (3j), (3k) | (4c) | (5d) | (6a) | (7a) | — | — |
| 422 | (1i) | (2g) | (3g), (3i), (3j), (3k) | (4c) | (5d) | (6a) | (7b), (7g) | — | — |
| 423 | (1i) | (2g) | (3g), (3i), (3j), (3k) | (4c) | (5d) | (6c) | (7a) | — | (7dd) |
| 424 | (1i) | (2g) | (3g), (3i), (3j), (3k) | (4c) | (5d) | (6c) | (7b), (7g) | — | (7dd) |
| 425 | (1i) | (2g) | (3g), (3i), (3j), (3k) | (4c) | (5d) | (6d) | — | (7r) | (7dd) |
| 426 | (1i) | (2g) | (3g), (3i), (3j), (3k) | (4c) | (5d) | (6d) | — | (7s), (7w) | (7dd) |
| 427 | (1i) | (2g) | (3g), (3i), (3j), (3k) | (4c) | (5e) | (6a) | (7a) | — | — |
| 428 | (1i) | (2g) | (3g), (3i), (3j), (3k) | (4c) | (5e) | (6a) | (7b), (7g) | — | — |
| 429 | (1i) | (2g) | (3g), (3i), (3j), (3k) | (4c) | (5e) | (6c) | (7a) | — | (7dd) |
| 430 | (1i) | (2g) | (3g), (3i), (3j), (3k) | (4c) | (5e) | (6c) | (7b), (7g) | — | (7dd) |
| 431 | (1i) | (2g) | (3g), (3i), (3j), (3k) | (4c) | (5e) | (6d) | — | (7r) | (7dd) |
| 432 | (1i) | (2g) | (3g), (3i), (3j), (3k) | (4c) | (5e) | (6d) | — | (7s), (7w) | (7dd) |

| Embodiment | Structural Formula | R⁴ | R⁴ᵃ | R⁴ᵇ | R⁴ᶜ |
|---|---|---|---|---|---|
| 433 | (1b) | (6a) | (7a) | — | — |
| 434 | (1b) | (6a) | (7b), (7g) | — | — |
| 435 | (1b) | (6c) | (7a) | — | (7dd) |
| 436 | (1b) | (6c) | (7b), (7g) | — | (7dd) |
| 437 | (1b) | (6d) | — | (7r) | (7dd) |
| 438 | (1b) | (6d) | — | (7s), (7w) | (7dd) |
| 439 | (1c) | (6a) | (7a) | — | — |
| 440 | (1c) | (6a) | (7b), (7g) | — | — |
| 441 | (1c) | (6c) | (7a) | — | (7dd) |
| 442 | (1c) | (6c) | (7b), (7g) | — | (7dd) |
| 443 | (1c) | (6d) | — | (7r) | (7dd) |
| 444 | (1c) | (6d) | — | (7s), (7w) | (7dd) |
| 445 | (1d) | (6a) | (7a) | — | — |
| 446 | (1d) | (6a) | (7b), (7g) | — | — |
| 447 | (1d) | (6c) | (7a) | — | (7dd) |
| 448 | (1d) | (6c) | (7b), (7g) | — | (7dd) |
| 449 | (1d) | (6d) | — | (7r) | (7dd) |
| 450 | (1d) | (6d) | — | (7s), (7w) | (7dd) |
| 451 | (1e) | (6a) | (7a) | — | — |
| 452 | (1e) | (6a) | (7b), (7g) | — | — |
| 453 | (1e) | (6c) | (7a) | — | (7dd) |
| 454 | (1e) | (6c) | (7b), (7g) | — | (7dd) |
| 455 | (1e) | (6d) | — | (7r) | (7dd) |
| 456 | (1e) | (6d) | — | (7s), (7w) | (7dd) |

| Embodiment | Structural Formula | R⁴ | R⁴ᵃ | R⁴ᶜ |
|---|---|---|---|---|
| 457 | (1c) | (6a) | (7b) | — |
| 458 | (1c) | (6a) | (7g) | — |
| 459 | (1c) | (6a) | (7n) | — |
| 460 | (1c) | (6a) | (7p) | — |
| 461 | (1c) | (6a) | (7q) | — |
| 462 | (1c) | (6a) | (7gg) | — |
| 463 | (1c) | (6c) | (7g) | (7dd) |
| 464 | (1d) | (6a) | (7b) | — |
| 465 | (1d) | (6a) | (7g) | — |
| 466 | (1d) | (6a) | (7n) | — |
| 467 | (1d) | (6a) | (7p) | — |
| 468 | (1d) | (6a) | (7q) | — |
| 469 | (1d) | (6a) | (7gg) | — |
| 470 | (1d) | (6c) | (7g) | (7dd) |
| 471 | (1e) | (6a) | (7b) | — |
| 472 | (1e) | (6a) | (7n) | — |

-continued

| 473 | (Ie) | (6a) | (7g)  | —     |
| 474 | (Ie) | (6a) | (7p)  | —     |
| 475 | (Ie) | (6a) | (7q)  | —     |
| 476 | (Ie) | (6a) | (7gg) | —     |
| 477 | (Ie) | (6c) | (7g)  | (7dd) |

In certain additional embodiments, including any of the embodiments described with reference to formulae (I), (Ia)-(Ie) and embodiments 1-477 above, each optionally substituted alkyl, alkenyl, and alkynyl recited in any one of preceding embodiments is unsubstituted. In alternative additional embodiments, including any of the embodiments described with reference to formulae (I), (Ia)-(Ie) and embodiments 1-477 above, each optionally substituted alkyl, alkenyl, and alkynyl recited in any one of preceding embodiments is independently substituted or unsubstituted. In further alternative additional embodiments, including any of the embodiments described with reference to formulae (I), (Ia)-(Ie) and embodiments 1-477 above, each optionally substituted alkyl, alkenyl, and alkynyl recited in any one of preceding embodiments is substituted.

In certain additional embodiments, including any of the embodiments described with reference to formulae (I), (Ia)-(Ie) and embodiments 1-477 above and the embodiment described in the paragraph immediately above, each cycloalkyl recited in any one of the preceding embodiments is a 3-7 membered monocyclic cycloalkyl. For example, in certain particular embodiments, including any of the embodiments described with reference to formulae (I), (Ia)-(Ie) and embodiments 1-477 above and the embodiment described in the paragraph immediately above, each cycloalkyl recited in any one of the preceding embodiments is a cyclopropyl, a cyclobutyl, a cyclopentyl, a cyclopentenyl, a cyclohexyl or a cyclohexenyl.

In certain additional embodiments, including any of the embodiments described with reference to formulae (I), (Ia)-(Ie) and embodiments 1-477 above and any embodiment described in the two paragraphs immediately above, each heterocycloalkyl recited in any one of the preceding embodiments is a 4-7 membered monocyclic heterocycloalkyl having 1-2 heteroatoms selected from O, S and N. For example, in certain particular embodiments, including any of the embodiments described with reference to formulae (I), (Ia)-(Ie) and embodiments 1-477 above and any embodiment described in the two paragraphs immediately above, each heterocycloalkyl recited in any one of the preceding embodiments is a pyrrolidinyl, a tetrahydrofuranyl, a tetrahydrothienyl, a piperidinyl, a piperazinyl, a morpholinyl, a thiomorpholinyl, a tetrahydro-2H-pyranyl, or a tetrahydro-2H-thiopyranyl. In certain particular embodiments, including any of the embodiments described with reference to formulae (I), (Ia)-(Ie) and embodiments 1-477 above and any embodiment described in the two paragraphs immediately above, each heterocycloalkyl recited in any one of the preceding embodiments is a pyrrolidine, a piperidine, a piperazine, a tetrahydrofuran, a (1H)dihydropyran, or a morpholine (e.g., each unsubstituted).

In certain additional embodiments, including any of the embodiments described with reference to formulae (I), (Ia)-(Ie) and embodiments 1-477 above and any embodiment described in the three paragraphs immediately above, each aryl is phenyl.

In certain additional embodiments, including any of the embodiments described with reference to formulae (I), (Ia)-(Ie) and embodiments 1-477 above and any embodiment described in the four paragraphs immediately above, each heteroaryl is a 5-6 membered monocyclic heteroaryl having 1-3 heteroatoms selected from O, S and N. For example, in certain particular embodiments, including any of the embodiments described with reference to formulae (I), (Ia)-(Ie) and embodiments 1-477 above and any embodiment described in the four paragraphs immediately above, each heteroaryl is a monocyclic heteroaryl is substituted with 0-3 $R^8$, e.g., is unsubstituted, substituted with one $R^8$ or substituted with two $R^8$. In certain particular embodiments, including any of the embodiments described with reference to formulae (I), (Ia)-(Ie) and embodiments 1-477 above and any embodiment described in the four paragraphs immediately above, each heteroaryl is a furanyl, a thienyl, a pyrrolyl, a pyrazolyl, an imidazolyl, an oxazolyl or a thiazolyl.

In certain additional embodiments, including any of the embodiments described with reference to formulae (I), (Ia)-(Ie) and embodiments 1-477 above and any embodiment described in the paragraphs immediately above, each $R^7$ is independently oxo, $C_1$-$C_4$ alkyl, $C_1$, F, Br, —CN, —SF$_5$, —N$_3$, nitro, —SR$^A$, —S(O)$_{1-2}$R$^A$, —OR$^A$, —NR$^B$R$^A$, —C(O)R$^A$, —C(O)NR$^B$R$^A$, —NR$^B$C(O)R$^A$, —C(S)NR$^B$R$^A$, —NR$^B$C(S)R$^A$, —CO$_2$R$^A$, —OC(O)R$^A$, C(O)SR A, —SC(O)R$^A$, —C(S)OR$^A$, —OC(S)R$^A$, —C(S)SR$^A$, SC(S)R$^A$, S(O)$_{1-2O}$R$^A$ OS(O)$_{1-2}$R$^A$ S(O)$_{1-2}$NR$^B$R$^A$, or —NR$^B$S(O)$_{1-2}$R$^A$. For example, in certain additional embodiments, including any of the embodiments described with reference to formulae (I), (Ia)-(Ie) and embodiments 1-477 above and any embodiment described in the paragraphs immediately above, each $R^7$ is independently oxo, $C_1$-$C_4$ alkyl, $C_1$, F, Br, —CN, —SF$_5$, —N$_3$, nitro, —SR$^A$, —S(O)$_{1-2}$R$^A$, —OR$^A$, —NR$^B$R$^A$, or —C(O)R$^A$.

In certain additional embodiments, including any of the embodiments described with reference to formulae (I), (Ia)-(Ie) and embodiments 1-477 above and any embodiment described in the paragraphs immediately above, each $R^8$ is independently $C_1$-$C_4$ alkyl, $C_1$, F, Br, —CN, —SF$_5$, —N$_3$, nitro, —SR$^A$, S(O)$_{1-2}$R$^A$, —OR$^A$, —NR$^B$R$^A$, —C(O)R$^A$, —C(O)NR$^B$R$^A$, —NR$^B$C(O)R$^A$, —C(S)NR$^B$R$^A$, —NR$^B$C(S)R$^A$, —CO$_2$R$^A$, —OC(O)R$^A$, —C(O)SR$^A$, SC(O)R$^A$, C(S)OR A, —OC(S)R$^A$, —C(S)SR$^A$, SC(S)R$^A$, S(O)$_{1-2}$OR$^A$, —OS(O)$_{1-2}$R$^A$ S( )$_{1-2}$NR$^B$R$^A$, or —NR$^B$S(O)$_{1-2}$R$^A$. In certain additional embodiments, including any of the embodiments described with reference to formulae (I), (Ia)-(Ie) and embodiments 1-477 above and any embodiment described in the paragraphs immediately above, each $R^8$ is independently $C_1$-$C_4$ alkyl, $C_1$, F, Br, —CN, SF$_5$, —N$_3$, nitro, —SR$^A$, —S(O)$_{1-2}$R$^A$, —OR$^A$, —NR$^B$R$^A$, or —C(O)R$^A$.

In some embodiments, the present disclosure relates in particular to a compound selected from:
3-(3,7-dimethylocta-2,6-dien-1-yl)-2,4-dihydroxy-6-pentylbenzenesulfonic acid;
sodium 3-(3,7-dimethylocta-2,6-dien-1-yl)-2,4-dihydroxy-6-pentylbenzenesulfonate;
2-(3,7-dimethylocta-2,6-dien-1-yl)-4-(methylsulfonyl)-5-pentylbenzene-1,3-diol;
4-(cyclopropylsulfonyl)-2-(3,7-dimethylocta-2,6-dien-1-yl)-5-pentylbenzene-1,3-diol;
4-(tert-butylsulfonyl)-2-(3,7-dimethylocta-2,6-dien-1-yl)-5-pentylbenzene-1,3-diol;
4-(benzylsulfonyl)-2-(3,7-dimethylocta-2,6-dien-1-yl)-5-pentylbenzene-1,3-diol;
2-(3,7-dimethylocta-2,6-dien-1-yl)-5-pentyl-4-(phenylsulfonyl)benzene-1,3-diol;
2-(3,7-dimethylocta-2,6-dien-1-yl)-4-((4-nitrophenyl)sulfonyl)-5-pentylbenzene-1,3-diol;

2-(3,7-dimethylocta-2,6-dien-1-yl)-5-pentyl-4-(pyridin-3-ylsulfonyl)benzene-1,3-diol;
2-(3,7-dimethylocta-2,6-dien-1-yl)-4-(furan-3-ylsulfonyl)-5-pentylbenzene-1,3-diol;
4-((1 H-imidazol-4-yl)sulfonyl)-2-(3,7-dimethylocta-2,6-dien-1-yl)-5-pentylbenzene-1,3-diol;
2-(3,7-dimethylocta-2,6-dien-1-yl)-4-(oxetan-3-ylsulfonyl)-5-pentylbenzene-1,3-diol;
2-(3,7-dimethylocta-2,6-dien-1-yl)-5-pentyl-4-((perfluorophenyl)sulfonyl)benzene-1,3-diol;
4-((3-(3,7-dimethylocta-2,6-dien-1-yl)-2,4-dihydroxy-6-pentylphenyl)sulfonyl)cyclohexan-1-one;
1-(2-((3-(3,7-dimethylocta-2,6-dien-1-yl)-2,4-dihydroxy-6-pentylphenyl)sulfonyl)ethyl)pyrrolidine-2,5-dione;
4-((2-(dimethylamino)ethyl)sulfonyl)-2-(3,7-dimethylocta-2,6-dien-1-yl)-5-pentylbenzene-1,3-diol;
1-(3-((3-(3,7-dimethylocta-2,6-dien-1-yl)-2,4-dihydroxy-6-pentylphenyl)sulfonyl)piperidin-1-yl)ethan-1-one;
4-((2-chloropyrimidin-5-yl)sulfonyl)-2-(3,7-dimethylocta-2,6-dien-1-yl)-5-pentylbenzene-1, 3-diol;
3-(3,7-dimethylocta-2,6-dien-1-yl)-2,4-dihydroxy-6-pentylbenzenesulfonamide;
3-(3,7-dimethylocta-2,6-dien-1-yl)-2,4-dihydroxy-N-methyl-6-pentylbenzenesulfonamide;
3-(3,7-dimethylocta-2,6-dien-1-yl)-2,4-dihydroxy-N, N-dimethyl-6-pentylbenzenesulfonamide;
N-cyclopropyl-3-(3,7-dimethylocta-2,6-dien-1-yl)-2,4-dihydroxy-6-pentylbenzenesulfonamide;
3-(3,7-dimethylocta-2,6-dien-1-yl)-2,4-dihydroxy-N-isopropyl-6-pentylbenzenesulfonamide;
3-(3,7-dimethylocta-2,6-dien-1-yl)-2,4-dihydroxy-6-pentyl-N-phenylbenzenesulfonamide;
N-benzyl-3-(3,7-dimethylocta-2,6-dien-1-yl)-2,4-dihydroxy-6-pentylbenzenesulfonamide;
2-(3,7-dimethylocta-2,6-dien-1-yl)-4-((4-methylpiperazin-1-yl)sulfonyl)-5-pentylbenzene-1,3-diol;
3-(3,7-dimethylocta-2,6-dien-1-yl)-2,4-dihydroxy-6-pentyl-N-(pyrimidin-2-yl)benzenesulfonamide;
2-(3,7-dimethylocta-2,6-dien-1-yl)-5-pentyl-4-(piperidin-1-ylsulfonyl)benzene-1,3-diol;
2-(3,7-dimethylocta-2,6-dien-1-yl)-4-(morpholinosulfonyl)-5-pentylbenzene-1,3-diol;
3-(3,7-dimethylocta-2,6-dien-1-yl)-2,4-dihydroxy-6-pentyl-N-(pyridin-3-yl)benzenesulfonamide;
3-(3,7-dimethylocta-2,6-dien-1-yl)-2,4-dihydroxy-N-(2-oxopropyl)-6-pentylbenzenesulfonamide;
1-((3-(3,7-dimethylocta-2,6-dien-1-yl)-2,4-dihydroxy-6-pentylphenyl)sulfonyl)azetidin-3-one;
3-(3,7-dimethylocta-2,6-dien-1-yl)-2,4-dihydroxy-N-(oxetan-2-ylmethyl)-6-pentylbenzene sulfonamide;
4-((2-azaspiro[3.3]heptan-2-yl)sulfonyl)-2-(3,7-dimethylocta-2,6-dien-1-yl)-5-pentylbenzene-1,3-diol;
4-((2,6-diazaspiro[3.3]heptan-2-yl)sulfonyl)-2-(3,7-dimethylocta-2,6-dien-1-yl)-5-pentylbenzene-1,3-diol;
((3-(3,7-dimethylocta-2,6-dien-1-yl)-2,4-dihydroxy-6-pentylphenyl)sulfonyl)alanine;
methyl ((3-(3,7-dimethylocta-2,6-dien-1-yl)-2,4-dihydroxy-6-pentylphenyl)sulfonyl)alaninate;
N-((3-(3,7-dimethylocta-2,6-dien-1-yl)-2,4-dihydroxy-6-pentylphenyl)sulfonyl)-3-morpholinopropanamide;
4-((3-(3,7-dimethylocta-2,6-dien-1-yl)-2,4-dihydroxy-6-pentylphenyl)sulfonamido)-4-oxobutanoic acid;
N-((3-(3,7-dimethylocta-2,6-dien-1-yl)-2,4-dihydroxy-6-pentylphenyl)sulfonyl)-3-(4-methylpiperazin-1-yl)propanamide;
2-amino-N-((3-(3,7-dimethylocta-2,6-dien-1-yl)-2,4-dihydroxy-6-pentylphenyl)sulfonyl)acetamide;
N-((3-(3,7-dimethylocta-2,6-dien-1-yl)-2,4-dihydroxy-6-pentylphenyl)sulfonyl)-2-(2-methoxyethoxy)acetamide;
2-amino-N-((3-(3,7-dimethylocta-2,6-dien-1-yl)-2,4-dihydroxy-6-pentylphenyl)sulfonyl)-3-hydroxypropanamide;
2-amino-N-((3-(3,7-dimethylocta-2,6-dien-1-yl)-2,4-dihydroxy-6-pentylphenyl)sulfonyl)propanamide;
3-amino-N-((3-(3,7-dimethylocta-2,6-dien-1-yl)-2,4-dihydroxy-6-pentylphenyl)sulfonyl)-2-methylpropanamide;
N-((3-(3,7-dimethylocta-2,6-dien-1-yl)-2,4-dihydroxy-6-pentylphenyl)sulfonyl)acetamide;
N-((3-(3,7-dimethylocta-2,6-dien-1-yl)-2,4-dihydroxy-6-pentylphenyl)sulfonyl)-3-oxobutanamide;
N-((3-(3,7-dimethylocta-2,6-dien-1-yl)-2,4-dihydroxy-6-pentylphenyl)sulfonyl)-2-(3-methyl-1 H-1,2,4-triazol-5-yl)acetamide;
N-((3-(3,7-dimethylocta-2,6-dien-1-yl)-2,4-dihydroxy-6-pentylphenyl)sulfonyl)-1H-1,2,4-triazole-5-carboxamide;
N-((3-(3,7-dimethylocta-2,6-dien-1-yl)-2,4-dihydroxy-6-pentylphenyl)sulfonyl)oxetane-2-carboxamide;
N-((3-(3,7-dimethylocta-2,6-dien-1-yl)-2,4-dihydroxy-6-pentylphenyl)sulfonyl)benzamide;
N-((3-(3,7-dimethylocta-2,6-dien-1-yl)-2,4-dihydroxy-6-pentylphenyl)sulfonyl)nicotinamide;
N-((3-(3,7-dimethylocta-2,6-dien-1-yl)-2,4-dihydroxy-6-pentylphenyl)sulfonyl)-2-phenylacetamide;
N-((3-(3,7-dimethylocta-2,6-dien-1-yl)-2,4-dihydroxy-6-pentylphenyl)sulfonyl)-2-(furan-2-yl)acetamide;
N-((3-(3,7-dimethylocta-2,6-dien-1-yl)-2,4-dihydroxy-6-pentylphenyl)sulfonyl)-2-(oxazol-2-yl)acetamide;
N-((3-(3,7-dimethylocta-2,6-dien-1-yl)-2,4-dihydroxy-6-pentylphenyl)sulfonyl)-2-(thiazol-2-yl)acetamide;
2-(1H-benzo[d]imidazol-2-yl)-N-((3-(3,7-dimethylocta-2,6-dien-1-yl)-2,4-dihydroxy-6-pentylphenyl)sulfonyl)acetamide;
3-(3,7-dimethylocta-2,6-dien-1-yl)-2,4-dihydroxy-6-pentyl-N-(phenylsulfonyl)benzamide;
N-(cyclohexylsulfonyl)-3-(3,7-dimethylocta-2,6-dien-1-yl)-2,4-dihydroxy-6-pentylbenzamide;
3-(3,7-dimethylocta-2,6-dien-1-yl)-2,4-dihydroxy-6-pentyl-N-((prop-1-en-1-yl)sulfonyl)benzamide;
N-((1H-benzo[d]imidazol-2-yl)sulfonyl)-3-(3,7-dimethylocta-2,6-dien-1-yl)-2,4-dihydroxy-6-pentylbenzamide;
N-cyclohexyl-3-(3,7-dimethylocta-2,6-dien-1-yl)-2,4-dihydroxy-6-pentylbenzenesulfonamide;
N-cyclobutyl-3-(3,7-dimethylocta-2,6-dien-1-yl)-2,4-dihydroxy-6-pentylbenzenesulfonamide;
3-(3,7-dimethylocta-2,6-dien-1-yl)-N-hexyl-2,4-dihydroxy-6-pentylbenzenesulfonamide;
N-allyl-3-(3,7-dimethylocta-2,6-dien-1-yl)-2,4-dihydroxy-6-pentylbenzenesulfonamide;
3-(3,7-dimethylocta-2,6-dien-1-yl)-2,4-dihydroxy-6-pentyl-N-(pyridin-3-ylsulfonyl)benzamide; and
phenyl-3-(3,7-dimethylocta-2,6-dien-1-yl)-2,4-dihydroxy-6-pentylbenzenesulfonate.

In some embodiments, the present disclosure further relates in particular to a compound selected from:
2-(3,7-dimethylocta-2,6-dien-1-yl)-4-(methylsulfonyl)-5-pentylbenzene-1,3-diol;
3-(3,7-dimethylocta-2,6-dien-1-yl)-2,4-dihydroxy-N-methyl-6-pentylbenzenesulfonamide;
3-(3,7-dimethylocta-2,6-dien-1-yl)-2,4-dihydroxy-N-isopropyl-6-pentylbenzenesulfonamide;
3-(3,7-dimethylocta-2,6-dien-1-yl)-2,4-dihydroxy-6-pentyl-N-phenylbenzenesulfonamide;
2-(3,7-dimethylocta-2,6-dien-1-yl)-4-(morpholinosulfonyl)-5-pentylbenzene-1,3-diol;

3-(3,7-dimethylocta-2,6-dien-1-yl)-2,4-dihydroxy-6-pentyl-N-(phenylsulfonyl)benzamide;

N-cyclohexyl-3-(3,7-dimethylocta-2,6-dien-1-yl)-2,4-dihydroxy-6-pentylbenzenesulfonamide;

N-cyclobutyl-3-(3,7-dimethylocta-2,6-dien-1-yl)-2,4-dihydroxy-6-pentylbenzenesulfonamide;

3-(3,7-dimethylocta-2,6-dien-1-yl)-N-hexyl-2,4-dihydroxy-6-pentylbenzenesulfonamide;

N-allyl-3-(3,7-dimethylocta-2,6-dien-1-yl)-2,4-dihydroxy-6-pentylbenzenesulfonamide;

3-(3,7-dimethylocta-2,6-dien-1-yl)-2,4-dihydroxy-6-pentyl-N-(pyridin-3-ylsulfonyl)benzamide; and phenyl-3-(3,7-dimethylocta-2,6-dien-1-yl)-2,4-dihydroxy-6-pentylbenzenesulfonate.

In certain embodiments of the compounds as otherwise described herein, the compound is in the form of a pharmaceutically acceptable salt of the compound as described herein or an enantiomer, diastereomer, racemate, tautomer, or metabolite thereof. The person of ordinary skill in the art will appreciate that a variety of pharmaceutically-acceptable salts may be provided, such as for example described in additional detail below.

In certain embodiments of the compounds as otherwise described herein, a compound is in the form of a solvate (e.g., a hydrate) of a compound as described herein, or an enantiomer, diastereomer, racemate, tautomer, or metabolite thereof. The person of ordinary skill in the art will appreciate that a variety of solvates and/or hydrates may be formed.

The person of ordinary skill in the art will appreciate that the phrase "or an enantiomer, diastereomer, racemate, tautomer, or metabolite thereof, or a pharmaceutically acceptable salt, solvate or hydrate of the compound, enantiomer, diastereomer, racemate, tautomer, or metabolite" includes compounds in the form of salts, solvates, hydrates of the base compounds (including its enantiomers, diastereomers, racemates, or tautomers) or a metabolite of the base compound. But in certain embodiments as described above, the compound is not in the form of a salt, solvate or hydrate.

Therapeutics Applications

In some embodiments, compounds of the present disclosure have an affinity for at least one cannabinoid receptor (e.g. CB1, CB2, 5HT1A, 5HT2A, GPR18, GPR55, GPR119, TRPV1, TPRV2, PPARs (such as PPARγ), or a μ-opioid receptor). Thus, in another aspect, the present disclosure relates to the use of at least one of the compounds of the present disclosure to bind and/or interact with a cannabinoid receptor.

In some embodiments, compounds of the present disclosure may have an affinity for one or both of the CB1 receptor and CB2 receptor. In a particular embodiment, compounds of the present disclosure may have an affinity for the CB1 receptor, but not the CB2 receptor. In a particular embodiment, compounds of the present disclosure may have an affinity for the CB2 receptor, but not the CB1 receptor.

In some embodiments, compounds of the present disclosure may exhibit a selectivity for one receptor over another. As used herein, by "selectivity" it is meant that a compound binds, interacts with, or modulates preferentially one receptor over another. In an embodiment, a compound is selective for one receptor over another if its affinity for one receptor is at least 1.25-fold, at least 1.5-fold, at least 2-fold, at least 5-fold, at least 10-fold, at least 25-fold, at least 50-fold, or at least 100-fold greater for the one receptor than another receptor. In an embodiment, the affinity of a compound as disclosed herein for a receptor may be determined by a radioligand competitive binding assay, such as for example described in the examples herein.

In some embodiments, compounds of the present disclosure may have an affinity for the CB1 receptor, with selectivity for the CB1 receptor over the CB2 receptor.

In some embodiments, compounds of the present disclosure may have an affinity for the CB2 receptor, with selectivity for the CB2 receptor over the CB1 receptor.

In some embodiments, compounds of the present disclosure may function as an agonist, a partial agonist, an indirect agonist, an antagonist, an inverse agonist, a neutral agonist, or an allosteric modulator to at least one cannabinoid receptor (e.g. CB1, CB2, 5HT1A, 5HT2A, GPR18, GPR55, GPR119, TRPV1, TPRV2, PPARs (such as PPARγ), or a μ-opioid receptor). In some embodiments, compounds of the present disclosure may function as an agonist, a partial agonist, an indirect agonist, antagonist, inverse agonist, neutral agonist, or allosteric modulator to the CB1 and/or CB2 receptor. In some embodiments, compounds of the present disclosure may function as an agonist to the CB1 and/or CB2 receptor. In some embodiments, compounds of the present disclosure may function as an antagonist to the CB1 and/or CB2 receptor. In some embodiments, compounds of the present disclosure may function as an indirect agonist to the 5HT1A receptor.

In some embodiments, compounds of the present disclosure may act as a prodrug to a compound (e.g. a metabolite) that functions as an agonist, a partial agonist, an indirect agonist, an antagonist, an inverse agonist, or a neutral agonist to at least one of the cannabinoid receptors (e.g. CB1, CB2, 5HT1A, 5HT2A, GPR18, GPR55, GPR119, TRPV1, TPRV2, PPARs (e.g. PPARγ), or a μ-opioid receptor).

The present disclosure further relates to use of a compound as disclosed herein as a therapeutically active substance or as a prodrug to a therapeutically active substance.

In an embodiment, the present disclosure relates to the use of a compound as disclosed herein for the treatment or prevention of a disease associated with a cannabinoid receptor (e.g. CB1, CB2, 5HT1A, 5HT2A, GPR18, GPR55, GPR119, TRPV1, TPRV2, PPARs (e.g. PPARγ), or a μ-opioid receptor). In an embodiment, by "disease associated with a cannabinoid" it is meant to refer to a disease, disorder or condition that is treatable or preventable by acting on a cannabinoid receptor (e.g. CB1, CB2, 5HT1A, 5HT2A, GPR18, GPR55, GPR119, TRPV1, TPRV2, PPARs (e.g. PPARγ), or a μ-opioid receptor). In an embodiment, compounds of the present disclosure may treat or prevent the condition by acting as an agonist, partial agonist, antagonist, inverse agonist, neutral agonist, or an allosteric modulator to the cannabinoid receptor or as a prodrug of a compound (e.g. metabolite) that acts as an agonist, partial agonist, antagonist, inverse agonist, neutral agonist, or allosteric modulator to the cannabinoid receptor. In select embodiments, the cannabinoid receptor is CB1 or CB2.

In an embodiment, the present disclosure relates to the use of a compound as disclosed herein for selectively modulating the activity of one receptor over another receptor.

In an embodiment, at least one of the receptors is a cannabinoid receptor. In an embodiment, both receptors are a cannabinoid receptor. In an embodiment, the receptors are CB1 and CB2. In select embodiments, the present disclosure relates to the use of a compound as disclosed herein for selectively modulating the activity of a CB1 or CB2 receptor.

As used herein, by "selectively modulating" it is intended to refer to the ability of the compounds of the present disclosure to cause any change in activity of the receptor. In an embodiment, "selectively modulating" means to stimulate or inhibit the activity of the receptor, either directly or indirectly.

The disclosure also relates to methods of treating or preventing a disease, such as a disease associated with a cannabinoid receptor (e.g. CB1 and/or CB2). These methods include administering to a subject in need of such treatment or prevention a therapeutically effective amount of one or more compounds of the disclosure as described herein (e.g., compounds of formula (I)) or a pharmaceutical composition of the disclosure as described herein.

In certain embodiments, the diseases of the disclosure include, but are not limited to ADHD/ADD, alcohol use disorder, allergic asthma, ALS, Alzheimer's, anorexia (e.g. HIV-related cachexia), anxiety disorders (e.g., social anxiety disorder, specific phobia, test anxiety, generalized anxiety disorder), arthritis, atherosclerosis, autism, bipolar disorder, burns, cancer, cancer pain, Charcot-Marie-Tooth disease, chronic inflammatory demyelinating polyneuropathies, chronic allograft nephropathy, cocaine use disorder, complex regional pain syndrome, congestive heart failure, depression, fibromyalgia, fragile X syndrome/FXTAS, frontotemporal dementias (behavioural variant), gingivitis pyrexia, glaucoma, glioblastoma, glomerulonephropathy, Huntington's disease, hypertrophic scars, IBD/IBS, inflammation, Inflammatory myopathies, ischemia, kidney fibrosis, keloids, leukodystrophies, liver fibrosis, liver cirrhosis, lung fibrosis, migraine, multiple sclerosis, myocardial infarction, nausea (e.g. CINV, motion sickness), neuropathic pain (e.g., postherpetic neuralgia, painful diabetic neuropathy), nightmare disorder, non-alcoholic fatty liver disease, obesity, obsessive-compulsive disorder, opioid sparing, opioid use disorder, osteoarthritis, osteoporosis, pain (e.g. acute or chronic pain), Parkinson's, post-concussion syndrome/traumatic brain injury, psychosis/schizophrenia, PTSD, regulation of bone mass, REM sleep behaviour disorder, reperfusion injury, Rett syndrome, rheumatoid arthritis, skin conditions (e.g. acne, psoriatic arthritis), sleep disorders (e.g., insomnia, RLS), spinocerebellar ataxias, systemic fibrosis, systemic sclerosis, thermal injury, tobacco use disorder/nicotine dependence, Tourette's, tumors, and trigeminal neuralgia.

The compounds and compositions of the disclosure as described herein may also be administered in combination with one or more secondary therapeutic agents. Thus, in certain embodiment, the method also includes administering to a subject in need of such treatment or prevention a therapeutically effective amount of one or more compounds of the disclosure as described herein or a pharmaceutical composition of the disclosure as described herein and one or more secondary therapeutic agents. Examples of suitable secondary therapeutic agents include, but are not limited to, temozolomide, camptothecin, doxorubicin, daunorubicin, vincristine, paclitaxel, neocarzinostatin, calicheamicin, cisplatin, carboplatin, oxaliplatin, satraplatin, picoplatin, lurtotecan, annamycin, docetaxel, tamoxifen, epirubicin, methotrexate, vinblastin, vincristin, topotecan, prednisone, prednisolone, chloroquine, hydroxychloroquine, autophagy inhibitors, abt-737, leucovorin, psilocybin, psilocin, psiloacetin, netupitant, palonosetron, aprepitant, 3,4-methylenedioxymethamphetamine, nicotine, ketamine, lithium salts (e.g., lithium citrate), valproic acid, bevacizumab, bortezomib, fluorouracil, gemcitabine, irinotecan, oxaliplatin, adalimumab, azathioprine, infliximab, citalopram, mirtazapine, sertraline, esketamine, fluoxetine, paroxetine, venlafaxine, fenfluramine, vigabatrin, bupropion, atomoxetine, memantine, clobazam, stiripentol, cyclosporine, tacrolimus, methylprednisolone, megestrol acetate, biguanides (e.g., metformin), sulphonyl ureas (e.g., glipizide, tolbutamide), gabapentin, baclofen, clonazepam, dantrolene, diazepam, tizanidine, buprenorphine, naltrexone, opioids (e.g., codeine, oxycodone, morphine), amisulpride, aripiprazole, olanzapine, quetiapine, risperidone, clonidine, lomazenil, benzodiazepine, benzamide, dexamethasone, gemcitabine, and palmitoylethanolamide. When administered as a combination, the compounds and compositions of the disclosure as described herein and the secondary therapeutic agents can be formulated as separate compositions that are given simultaneously or sequentially, or the therapeutic agents can be given as a single composition. In certain embodiments, the secondary therapeutic agent may be administered in an amount below its established half maximal inhibitory concentration ($IC_{50}$). For example, the secondary therapeutic agent may be administered in an amount less than 1% of, e.g., less than 10%, or less than 25%, or less than 50%, or less than 75%, or even less than 90% of the inhibitory concentration ($IC_{50}$).

Prodrugs

In some embodiments, a compound as described herein may itself be a prodrug or may be further modified to provide a prodrug.

Prodrugs in accordance with the present disclosure may, for example, be produced by replacing appropriate functionalities present in the compounds disclosed herein, such as for example any of the embodiments described with reference to formulae (I), (Ia)-(Ie) and embodiments 1-477 above, with certain moieties known to those skilled in the art as "promoieties" as described, for example, in Design of Prodrugs by H. Bundgaard (Elsevier, 1985) and Y. M. Choi-Sledeski and C. G. Wermuth, Designing Prodrugs and Bioprecursors in Practice of Medicinal Chemistry, (Fourth Edition), Chapter 28, 657-696 (Elsevier, 2015).

In exemplary embodiments, a prodrug in accordance with the present disclosure is (a) an ester or amide derivative of a carboxylic acid in a compound disclosed herein; (b) an ester, carbonate, carbamate, acetal, aminal, phosphate, or ether derivative of a hydroxyl group in a compound disclosed herein; (c) an amide, imine, carbamate or amine derivative of an amino group in a compound disclosed herein; (d) an oxime or imine derivative of a carbonyl group in a compound disclosed herein; or (e) a methyl, primary alcohol or aldehyde group that can be metabolically oxidized to a carboxylic acid in a compound disclosed herein.

Certain compounds of the present disclosure, such as for example any of the embodiments described with reference to formulae (I), (Ia)-(Ie) and embodiments 1-477 above, may themselves act as prodrugs. In an embodiment, a compound of the present disclosure, such as for example any of the embodiments described with reference to formulae (I), (Ia)-(Ie) and embodiments 1-477 above, may act as a prodrug of a cannabinoid, such as for example a natural cannabinoid (e.g. CBD or CBDA).

References to compounds disclosed herein are taken to include the compounds themselves and prodrugs thereof. The present disclosure includes such prodrug compounds as well as any pharmaceutically acceptable salts of such prodrug compounds, and/or any solvates, hydrates, enantiomers, diastereomers, racemates, tautomers, or metabolites of such prodrug compounds and their salts.

In some embodiments, a prodrug compound of the present disclosure may exhibit improved pharmacokinetics (PK), improved biodistribution, and/or improved formulation capabilities (e.g. stability in formulation). For example, in an embodiment, these characteristics may be improved over natural cannabinoids (e.g. CBD or CBDA).

In some embodiments, a prodrug compound of the present disclosure may exhibit unique or improved biological activity. For example, in an embodiment, these characteristics may be unique or improved over natural cannabinoids (e.g. CBD or CBDA).

Pharmaceutical Compositions and Dosage Forms

A compound as described herein can usefully be provided in the form of a pharmaceutical composition. Such compositions include the compound according to any one of the preceding aspects or embodiments described herein, together with a pharmaceutically acceptable excipient, diluent, or carrier.

The compounds may be formulated in the pharmaceutical composition per se, or in the form of a hydrate, solvate, or pharmaceutically acceptable salt, as previously described. Typically, such salts are more soluble in aqueous solutions than the corresponding free acids and bases, but salts having lower solubility than the corresponding free acids and bases may also be formed.

The pharmaceutical composition can be, for example, in the form of a tablet, a capsule, or a parenteral formulation, but the person of ordinary skill in the art will appreciate that the compound can be provided in a wide variety of pharmaceutical compositions.

The compounds of the disclosure can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like. A medicament including a compound of the disclosure can be provided, for example, in any of the formulations and dosage forms as described herein.

Pharmaceutical compositions can be made using the presently disclosed compounds. For example, in one embodiment, a pharmaceutical composition includes a pharmaceutically acceptable carrier, diluent or excipient, and compound as described above with reference to any one of structural formulae.

In the pharmaceutical compositions disclosed herein, one or more compounds of the disclosure may be present in association with one or more pharmaceutically acceptable carriers, diluents or excipients, and, if desired, other active ingredients. The pharmaceutical compositions containing compounds of the disclosure may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques.

In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Formulations for oral use can also be presented as beverages or edibles. For example, in an embodiment, the compounds of the present disclosure may be presented in water-soluble formulations such as disclosed in PCT/CA2019/051698, comprising an emulsifier and a glycerin-based carrier surfactant. In other embodiments, the compounds of the present disclosure may be presented in compositions such as disclosed in PCT/CA2019/051704, comprising inulin and pectin.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

In some embodiments, the pharmaceutically acceptable carrier, diluent, or excipient is not water. In other embodiments, the water comprises less than 50% of the composition. In some embodiments, compositions comprising less than 50% water have at least 1%, 2%, 3%, 4% or 5% water. In other embodiments, the water content is present in the composition in a trace amount.

In some embodiments, the pharmaceutically acceptable carrier, diluent, or excipient is not alcohol. In other embodiments, the alcohol comprises less than 50% of the composition. In some embodiments, compositions comprising less than 50% alcohol have at least 1%, 2%, 3%, 4% or 5% alcohol. In other embodiments, the alcohol content is present in the composition in a trace amount.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of the disclosure can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of the disclosure can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compositions can be formulated in a unit dosage form of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The compound can be effective over a wide dosage range and is generally administered in a therapeutically effective amount. It will be understood, however, that the amount of the compound actually administered will usually be determined by a physician, according to the relevant circumstances, including the condition to be treated or prevented, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated or prevented as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

The person of ordinary skill in the art will formulate a compound as described into pharmaceutical formulations herein. For example, based on the physicochemical properties of the compound, the amount of the compound needed for a therapeutically effective amount, and the desired route of administration.

Definitions

Terms used herein may be preceded and/or followed by a single dash, "—", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" with reference to the chemical structure referred to unless a dash indicates otherwise. For example, arylalkyl, arylalkyl-, and -alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. CH$_3$—CH$_2$—), in some circumstances a bivalent linking moiety can be "alkyl," in which case those skilled in the art will understand the alkyl to be a divalent radical (e.g., —CH$_2$—CH$_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for 0, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as —B-(A)$_a$, wherein a is 0 or 1. In such instances, when a is 0 the moiety is —B and when a is 1 the moiety is —B-A.

As used herein, the term "alkyl" includes a saturated hydrocarbon having a designated number of carbon atoms, such as 1 to 10 carbons (i.e., inclusive of 1 and 10), 1 to 8 carbons, 1 to 6 carbons, 1 to 3 carbons, or 1, 2, 3, 4, 5 or 6. Alkyl group may be straight or branched and depending on context, may be a monovalent radical or a divalent radical (i.e., an alkylene group). For example, the moiety "—(C$_1$-C$_6$alkyl)-O—" signifies connection of an oxygen through an alkylene bridge having from 1 to 6 carbons and C$_1$-C$_3$ alkyl represents methyl, ethyl, and propyl moieties. Examples of "alkyl" include, for example, methyl, ethyl, propyl, isopropyl, butyl, iso-, sec- and tert-butyl, pentyl, and hexyl.

The term "alkoxy" represents an alkyl group of indicated number of carbon atoms attached to the parent molecular moiety through an oxygen bridge, such as alkyl-O— in which the term "alkyl" has the previously given definition. Examples of "alkoxy" include, for example, methoxy, ethoxy, propoxy, and isopropoxy.

The term "alkenyl", as used herein, represents an unsaturated hydrocarbon having a designated number of carbon atoms, such as 2 to 10 carbons (i.e., inclusive of 2 and 10), 2 to 8 carbons, 2 to 6 carbons, or 2, 3, 4, 5 or 6, unless otherwise specified, and containing at least one carbon-carbon double bond. Alkenyl group may be straight or branched and depending on context, may be a monovalent radical or a divalent radical (i.e., an alkenylene group). For example, the moiety "—(C$_2$-C$_6$alkenyl)-O—" signifies connection of an oxygen through an alkenylene bridge having from 2 to 6 carbons. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkynyl", as used herein, represents an unsaturated hydrocarbon having a designated number of carbon atoms, such as 2 to 10 carbons (i.e., inclusive of 2 and 10), 2 to 8 carbons, 2 to 6 carbons, or 2, 3, 4, 5 or 6 unless otherwise specified, and containing at least one carbon-carbon triple bond. Alkynyl group may be straight or branched and depending on context, may be a monovalent radical or a divalent radical (i.e., an alkynylene group). For example, the moiety "—(C$_2$-C$_6$alkynyl)-O—" signifies connection of an oxygen through an alkynylene bridge having from 2 to 6 carbons. Representative examples of alkynyl include, but are not limited to, acetylenyl, 1-propynyl, 2-propynyl, 3-butynyl, 2-pentynyl, and 1-butynyl.

The term "aryl" represents an aromatic ring system having a single ring (e.g., phenyl) which is optionally fused to other aromatic hydrocarbon rings or non-aromatic hydrocarbon or heterocycle rings. "Aryl" includes ring systems having multiple condensed rings and in which at least one is carbocyclic and aromatic, (e.g., 1,2,3,4-tetrahydronaphthyl, naphthyl).

Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. "Aryl" also includes ring systems having a first carbocyclic, aromatic ring fused to a nonaromatic heterocycle, for example, 1H-2,3-dihydrobenzofuranyl and tetrahydroisoquinolinyl. The aryl groups herein are unsubstituted or, when specified as "optionally substituted", can unless stated otherwise be substituted in one or more substitutable positions with various groups as indicated.

The terms "halogen" or "halo" indicate fluorine, chlorine, bromine, and iodine. In certain embodiments of each and every embodiment as otherwise described herein, the term "halogen" or "halo" refers to fluorine or chlorine. In certain embodiments of each and every embodiment described herein, the term "halogen" or "halo" refers to fluorine. The term "fluoroalkyl" indicates an alkyl group (i.e., as otherwise described herein) that is substituted with at least one fluorine. "Fluoroalkyl" includes alkyl groups substituted with multiple fluorines, such as perfluoroalkyl groups. Examples of fluoroalkyl groups include fluoromethyl, difluoromethyl, trifluoromethyl, pentafluoroethyl, 2,2,2-trifluoroethyl, 1,1,1,3,3,3-hexafluoroprop-2-yl and 2,2,3,3,3-pentafluoroprop-1-yl.

The term "heteroaryl" refers to an aromatic ring system containing at least one aromatic heteroatom selected from nitrogen, oxygen and sulfur in an aromatic ring. Most commonly, the heteroaryl groups will have 1, 2, 3, or 4 heteroatoms. The heteroaryl may be fused to one or more non-aromatic rings, for example, cycloalkyl or heterocycloalkyl rings, wherein the cycloalkyl and heterocycloalkyl rings are described herein. In one embodiment of the present compounds the heteroaryl group is bonded to the remainder of the structure through an atom in a heteroaryl group aromatic ring. In another embodiment, the heteroaryl group is bonded to the remainder of the structure through a non-aromatic ring atom. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, isoindolinyl, isobenzothienyl, benzoxazolyl, pyridopyridinyl, purinyl, benzodioxolyl, triazinyl, pteridinyl, benzothiazolyl, imidazopyridinyl, imidazothiazolyl, benzisoxazinyl, benzoxazinyl, benzopyranyl, benzothiopyranyl, chromonyl, chromanonyl, pyridinyl-N-oxide, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as indicated.

The term "heterocycloalkyl" refers to a non-aromatic ring or ring system containing at least one heteroatom that is preferably selected from nitrogen, oxygen and sulfur, wherein said heteroatom is in a non-aromatic ring. The heterocycloalkyl may have 1, 2, 3 or 4 heteroatoms. The heterocycloalkyl may be saturated (i.e., a heterocycloalkyl) or partially unsaturated (i.e., a heterocycloalkenyl). Heterocycloalkyl includes monocyclic groups of three to eight annular atoms as well as bicyclic and polycyclic ring systems, including bridged and fused systems, wherein each ring includes three to eight annular atoms. The heterocycloalkyl ring is optionally fused to other heterocycloalkyl rings and/or non-aromatic hydrocarbon rings. In certain embodiments, the heterocycloalkyl groups have from 3 to 7 members in a single ring. In other embodiments, heterocycloalkyl groups have 5 or 6 members in a single ring. In some embodiments, the heterocycloalkyl groups have 3, 4, 5, 6 or 7 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butyrolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as indicated.

The term "cycloalkyl" refers to a non-aromatic carbocyclic ring or ring system, which may be saturated (i.e., a cycloalkyl) or partially unsaturated (i.e., a cycloalkenyl). The cycloalkyl ring may be optionally fused to or otherwise attached (e.g., bridged systems) to other cycloalkyl rings. Certain examples of cycloalkyl groups of the present disclosure have from 3 to 7 members in a single ring, such as having 5 or 6 members in a single ring. In some embodiments, the cycloalkyl groups have 3, 4, 5, 6 or 7 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups, as indicated.

The term "ring system" encompasses monocycles, as well as fused and/or bridged polycycles.

The term "amino" signifies the primary amino group, the secondary amino group, or the tertiary amino group, as context dictates.

The term "carbonyl" signifies the —C(O)— group.

The terms "hydroxy" and "hydroxyl" signify the —OH group.

The term "oxo" means a doubly bonded oxygen, sometimes designated as =O or for example in describing a carbonyl "C(O)" may be used to show an oxo substituted carbon.

The term "oxy" signifies the —O— group.

The term "sulfonyl" signifies the —SO$_2$— group.

The term "substituted," when used to modify a specified group or radical, means that one or more hydrogen atoms of the specified group or radical are each, independently of one another, replaced with the same or different substituent groups as defined below, unless specified otherwise.

As used herein, the term "metabolite" means a compound that results from the metabolism of a compound of the present disclosure, including from any of the embodiments described with reference to formulae (I), (Ia)-(Ie) and embodiments 1-477 above. In an embodiment, the metabolite is an active metabolite meaning that it is a physiologically active compound. In an embodiment, the metabolite is an active compound obtained from metabolism of a prodrug as described herein.

The term "pharmaceutically acceptable" is meant as reference to a compound, substance or composition that is generally safe, non-toxic and biologically acceptable.

As used herein, the phrase "pharmaceutically acceptable salt" refers to both pharmaceutically acceptable acid and base addition salts. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

One of ordinary skill in the art of medicinal chemistry also will appreciate that the disclosed structures are intended to include isotopically enriched forms of the present compounds. As used herein "isotopes" includes those atoms having the same atomic number but different mass numbers. As is known to those of skill in the art, certain atoms, such as hydrogen occur in different isotopic forms. For example, hydrogen includes three isotopic forms, protium, deuterium and tritium. As will be apparent to those of skill in the art upon consideration of the present compounds, certain compounds can be enriched at a given position with a particular isotope of the atom at that position. For example, compounds having a fluorine atom, may be synthesized in a form enriched in the radioactive fluorine isotope $^{18}F$. Similarly, compounds may be enriched in the heavy isotopes of hydrogen: deuterium and tritium; and similarly can be enriched in a radioactive isotope of carbon, such as $^{13}C$. Such isotopic variant compounds undergo different metabolic pathways and can be useful, for example, in studying the ubiquitination pathway and its role in disease. Of course, in certain embodiments, the compound has substantially the same isotopic character as naturally-occurring materials.

The compounds of the present disclosure may contain chiral centers, which may be either of the (R) or (S) configuration, or may comprise a mixture thereof. Accordingly, the present invention also includes stereoisomers of the compounds described herein, where applicable, either individually or admixed in any proportions. Stereoisomers may include, but are not limited to, enantiomers, diastereomers, racemic mixtures (racemates), and combinations thereof. Such stereoisomers can be prepared and separated using conventional techniques, either by reacting enantiomeric starting materials, or by separating isomers of compounds of the present invention.

Isomers may further include tautomers and geometric isomers. Examples of geometric isomers include, but are not limited to, cis isomers or trans isomers across a double bond. Other isomers are contemplated among the compounds of the present disclosure. The isomers may be used either in pure form or in admixture with other isomers of the compounds disclosed herein. In some embodiments, compounds of the present disclosure may have a natural CBG-type configuration as indicated below:

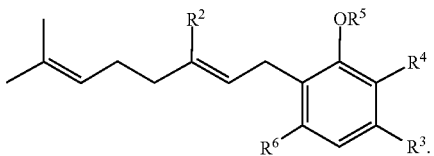

One of ordinary skill in the art of chemistry will also appreciate that the disclosed structures, unless otherwise indicated are intended to include all possible stereoisomers of the claimed molecule, including mixtures of certain or all stereoisomers. However, compounds drawn with certain stereochemistry at one or more stereocenters are indicative of the compounds in that particular embodiment having the indicated stereochemistry. Compounds and stereocenters drawn with ambiguous stereochemistry are meant to convey any stereoisomer or mixture thereof, e.g., a racemic mixture of compounds or a purified subset of stereoisomers.

As used herein, the terms "individual," "patient," or "subject", used interchangeably, refer to any animal, including mammals, and preferably humans.

As used herein, the phrase "therapeutically effective amount" or "effective amount" refers to the amount of active compound or pharmaceutical agent that elicits the biological or medicinal response that is being sought in a cell, tissue, system, animal, individual or human by a researcher, veterinarian, medical doctor or other clinician.

In certain embodiments, an effective amount can be an amount suitable for
 (i) inhibiting the progression the disease;
 (ii) prophylactic use for example, preventing or limiting development of a disease, condition or disorder in an individual who may be predisposed or otherwise at risk to the disease, condition or disorder but does not yet experience or display the pathology or symptomatology of the disease;
 (iii) inhibiting the disease; for example, inhibiting a disease, condition or disorder in an individual who is experiencing or displaying the pathology or symptomatology of the disease, condition or disorder;
 (iv) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or
 (v) eliciting the referenced biological effect.

As used herein, the terms "treatment" and "treating" means (i) ameliorating the referenced disease state, condition, or disorder (or a symptom thereof), such as, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease or symptom thereof, or inhibiting the progression of disease; or (ii) eliciting the referenced biological effect (e.g., inducing apoptosis, or inhibiting glutathione synthesis).

As used herein, the terms "preventing" or "prevent" means completely or partially preclude or delay the onset in a subject of a referenced disease state, condition, or disorder (or a symptom thereof).

Methods of Preparation

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969. In further embodiments, compounds may be purified by preparative HPLC.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/I, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

A "leaving group" as used herein (e.g. suitable as LG) refers to a moiety of a reactant (e.g., the alkylhalogenide of the disclosure) that is displaced from the first reactant in the chemical reaction. A comprehensive and non-limiting list of suitable leaving groups can be found in J. March, Advanced Organic Chemistry, John Wiley and Sons, N.Y. (2013). Examples of suitable leaving groups include, but are not limited to, halogen (such as $C_1$ or Br), acetoxy, and sulfonyloxy groups (such as methyl sulfonyloxy, trifluoromethylsulfonyloxy ("triflate"), p-toluenesulfonyloxy ("tosylate")).

The compounds disclosed herein can be made using procedures familiar to the person of ordinary skill in the art and as described herein, for example in Schemes 1-3. One of skill in the art can adapt the reaction sequences of schemes and examples as provided herein to fit the desired target molecule. Of course, in certain situations one of skill in the art will use different reagents to affect one or more of the individual steps or to use protected versions of certain of the substituents. Additionally, one skilled in the art would recognize that compounds of the disclosure can be synthesized using different routes altogether. For example, the person of ordinary skill in the art may adapt the procedures described herein and/or other procedures familiar to the person of ordinary skill in the art to make the compounds described herein.

Scheme 1

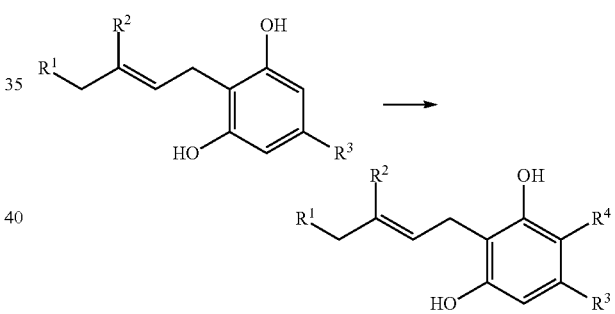

wherein $R^1$, $R^2$, $R^3$, and $R^4$ are as defined in formula(I).

Scheme 2

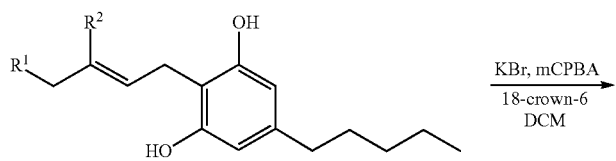

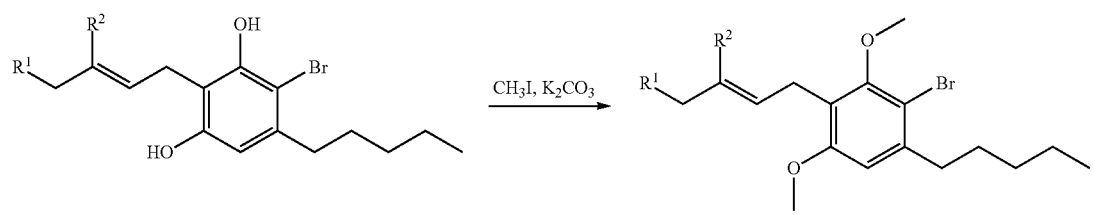

-continued
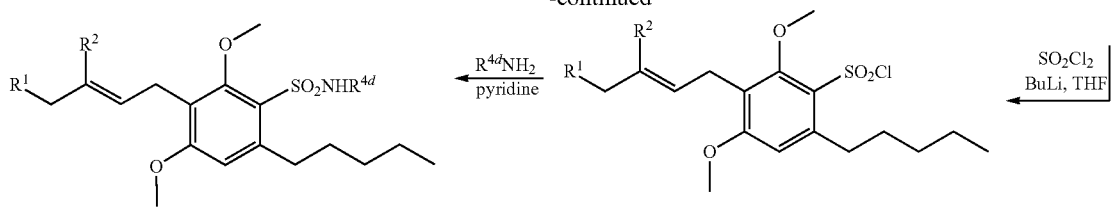
wherein $R^1$, $R^2$, and $R^{4d}$ are as defined in formula (I).
Scheme 3
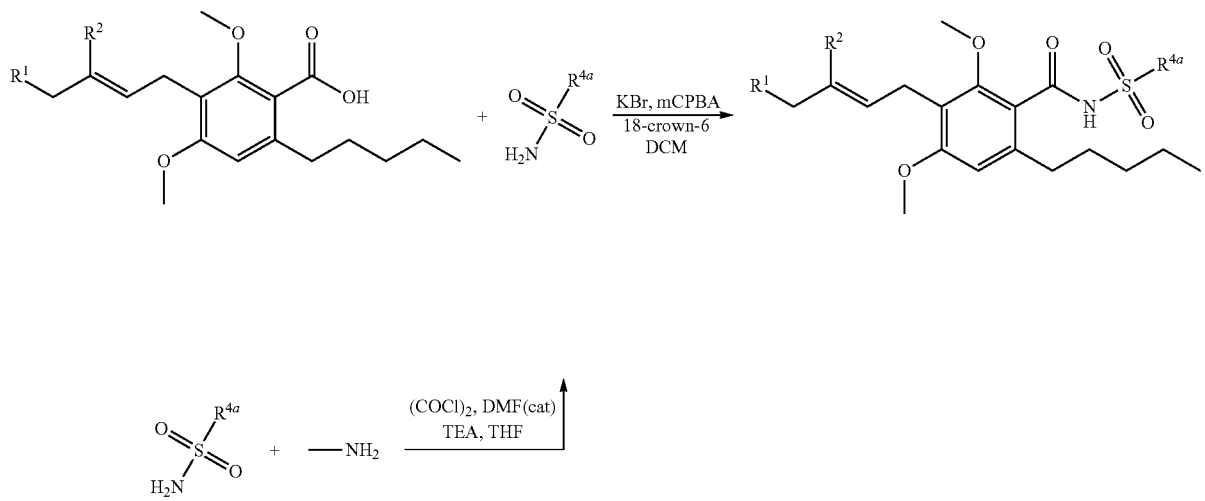
wherein $R^1$, $R^2$, and $R^{4a}$ are as defined in formula (I).
Scheme 4
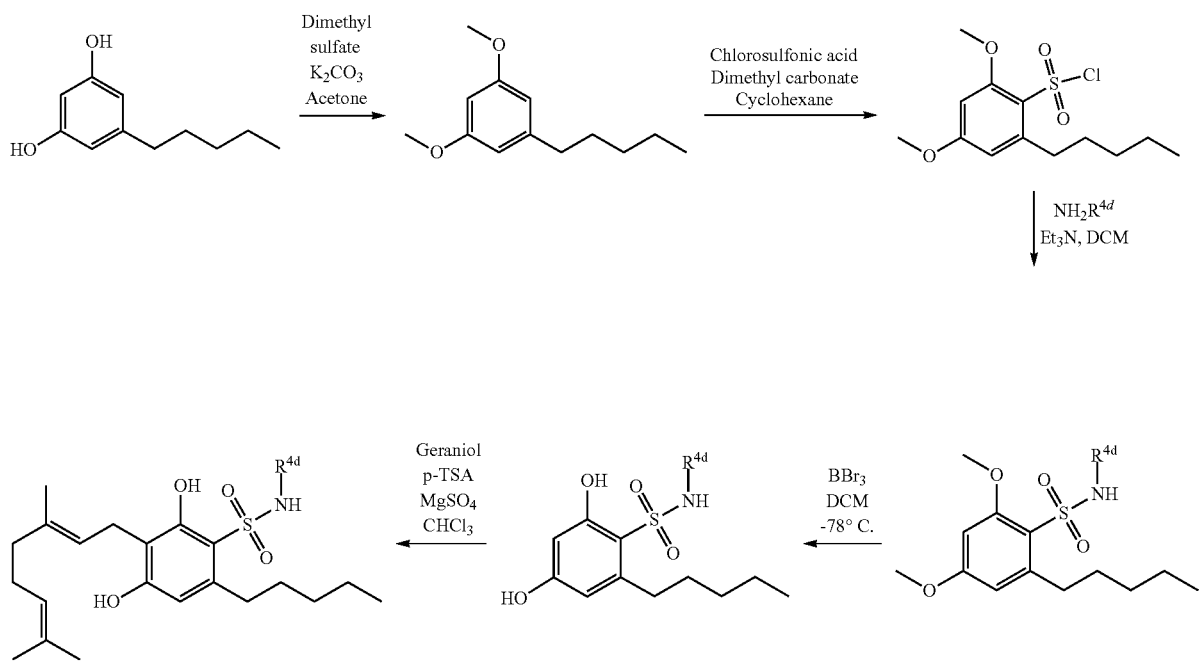

wherein $R^{4d}$ is as defined in formula (I).
Scheme 5
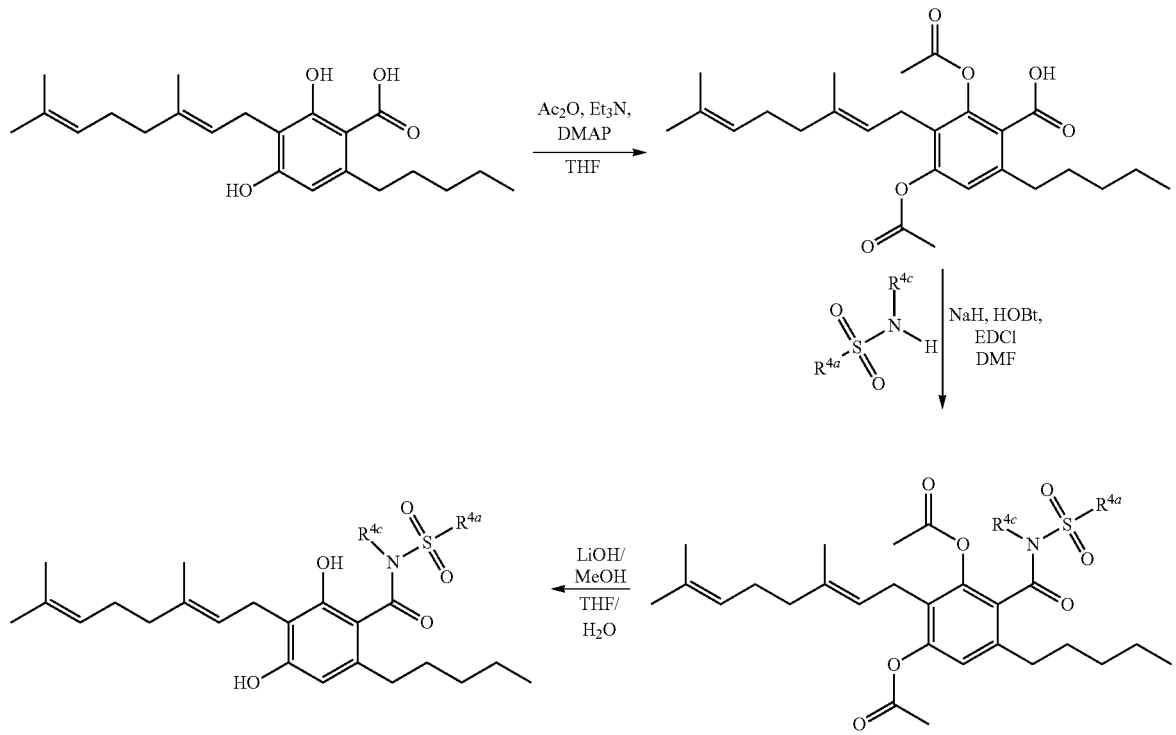
wherein $R^{4a}$ and $R^{4c}$ are as defined in formula (I).
Scheme 6
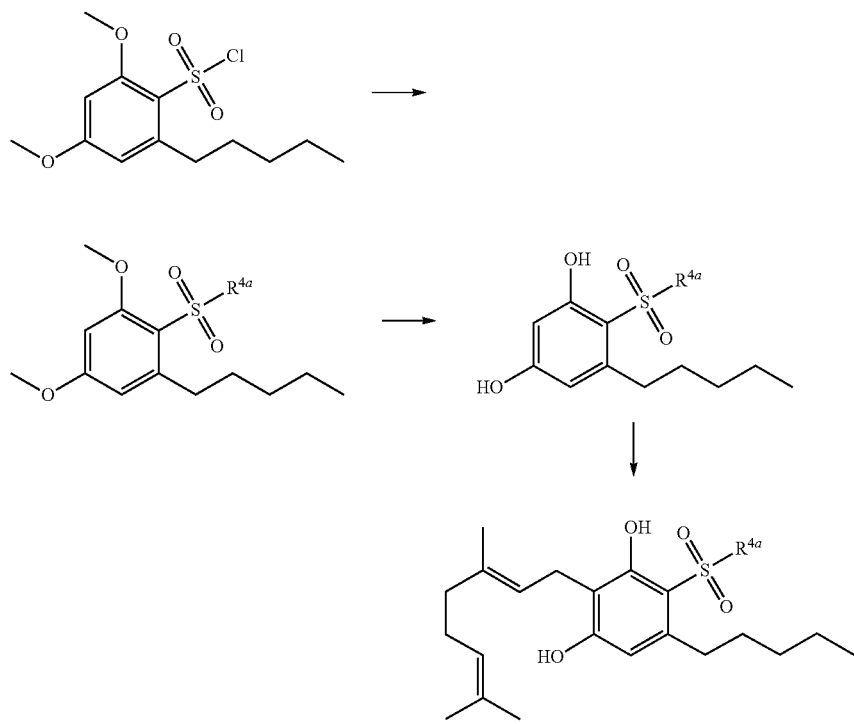

EXAMPLES

The preparation of the compounds of the disclosure is illustrated further by the following examples, which are not to be construed in any way as limiting the disclosure in scope or spirit to the specific procedures and compounds described in them. These examples are offered to illustrate the invention.

Compound Synthesis and Formulation

Example 1: 3-(3,7-dimethylocta-2,6-dien-1-yl)-2,4-dihydroxy-N-methyl-6-pentylbenzenesulfonamide (20)

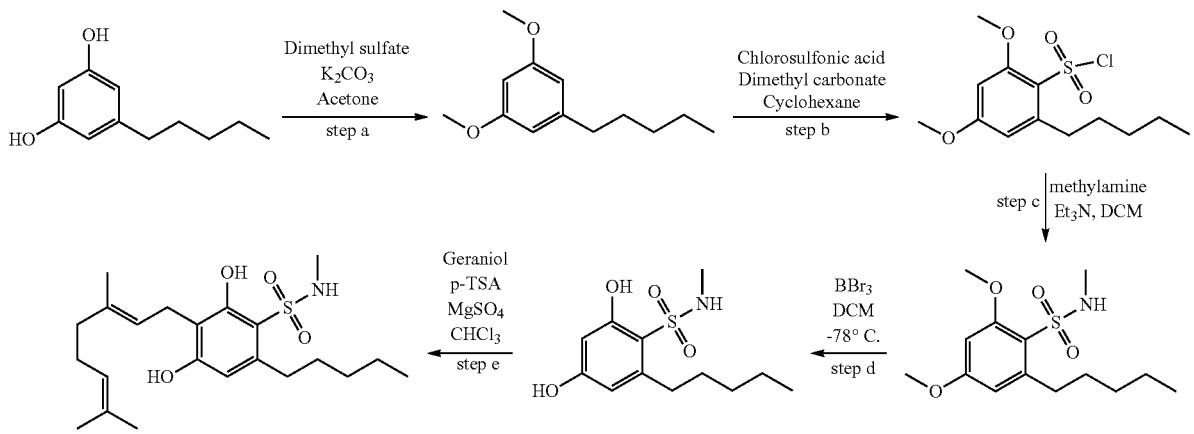

Step a. To a solution of olivetol (10 g, 55.48 mmol) in dry acetone at room temperature was added K$_2$CO$_3$ (23.00 g, 166.44 mmol) and dimethyl sulfate (27.99 g, 221.92 mmol). The reaction mixture was stirred at room temperature for 15 min and refluxed for 14 h. The reaction mixture was cooled to room temperature, filtered, and the filtrate was concentrated. The crude mixture was diluted in diethyl ether and the organic layer was stirred with 10% NaOH for 1 h at room temperature. The organic layer was then washed with 1M HCl and water, dried over Na$_2$SO$_4$ and concentrated to give 1,3-dimethoxy-5-pentyl-benzene, which was used for next steps without further purification.

Step b. To a solution of 1,3-dimethoxy-5-pentyl-benzene (4.0 g, 19.20 mmol) and chlorosulfonic acid (11.19 g, 96.02 mmol, 6.39 mL) in cyclohexane (12 mL) at 60° C. was added dimethyl carbonate (9.00 g, 99.86 mmol, 8.41 mL) dropwise and the temperature was increased to 70° C. The reaction mixture was stirred for 2 h at this temperature and then cooled to room temperature. The mixture was poured into cold water and extracted with diethyl ether. Combined organic layers were dried over Na$_2$SO$_4$ and concentrated. The crude mixture was purified by flash column chromatography using ethyl acetate-hexane to afford 2,4-dimethoxy-6-pentyl-benzenesulfonyl chloride as light-yellow oil (49% yield). $^1$H NMR (400 MHz, CD$_3$CN) δ 6.62 (d, J=2.5 Hz, 1H), 6.55 (d, J=2.5 Hz, 1H), 4.01 (s, 3H), 3.91 (s, 3H), 3.07-2.98 (m, 2H), 1.68-1.60 (m, 2H), 1.41-1.35 (m, 4H), 0.94-0.89 (m, 3H).

Step c. To a 10 mL microwave vial was added 2,4-dimethoxy-6-pentyl-benzenesulfonyl chloride (325 mg, 1.06 mmol) and dichloromethane (DCM; 3 mL). The solution was stirred at room temperature and Et$_3$N (221 μL, 1.59 mmol) was added dropwise. The mixture was stirred for 10 min after which methylamine (2M in methanol 1.06 mL) was added dropwise. The mixture was stirred for another 4 h at room temperature. Water was added and the mixture was extracted with DCM. The combined organic layers were filtered, concentrated and purified by flash column chromatography using ethyl acetate-hexane to give 2,4-dimethoxy-N-methyl-6-pentyl-benzenesulfonamide (62% yield). $^1$H NMR (400 MHz, CDCl$_3$) δ 6.44 (s, 2H), 5.15 (s, 1H), 3.96 (s, 3H), 3.88 (s, 3H), 3.11-3.03 (m, 2H), 2.62 (s, 3H), 1.66 (m, 2H), 1.49-1.33 (m, 4H), 0.98-0.89 (m, 3H).

Step d. To a solution of 2,4-dimethoxy-N-methyl-6-pentyl-benzenesulfonamide (150 mg, 0.50 mmol) in DCM (3 mL) at −78° C. was added with boron tribromide (1 M, 2.49 mL) dropwise. The mixture was stirred at room temperature for 12 h, quenched with 1M HCl and extracted with DCM. The organic layer was washed with brine, dried over Na$_2$SO$_4$, concentrated and purified by flash column chromatography using ethyl acetate-hexane to give 2,4-dihydroxy-N-methyl-6-pentyl-benzenesulfonamide (70% yield) as a white solid. $^1$H NMR (400 MHz, CDCl$_3$) δ 10.03 (s, 1H), 6.38 (d, J=2.7 Hz, 1H), 6.32 (d, J=2.6 Hz, 1H), 5.31 (s, 1H), 4.42 (d, J=5.9 Hz, 1H), 2.89-2.81 (m, 2H), 2.67 (d, J=5.4 Hz, 3H), 1.60 (m, 2H), 1.40 (dq, J=10.9, 3.3 Hz, 4H), 0.96-0.91 (m, 3H).

Step e. In a dry and argon-purged round-bottom flask sealed with a rubber cork and fitted with a stir bar, 2,4-dihydroxy-N-methyl-6-pentyl-benzenesulfonamide (95 mg, 0.35 mmol) was charged followed by the addition of chloroform (3 mL) and anhydrous MgSO$_4$ (63 mg, 0.52 mmol). The flask was placed in an ice bath and cooled for 10 min. p-Toluenesulfonic acid monohydrate (6.6 mg, 0.035 mmol) was added and the reaction mixture was stirred for 10 min. Geraniol (107 mg, 0.70 mmol) was added and the reaction was stirred in an ice bath for additional 30 min. The reaction was removed from the ice bath and the stirred for 18 h at room temperature. The reaction mixture was quenched with sat. NaHCO$_3$ and the organic layer was washed with saturated NaHCO$_3$ and brine. The organic extract was dried over Na$_2$SO$_4$, concentrated and purified by flash column chromatography using ethyl acetate-hexane to give (E)-3-(3,7-dimethylocta-2,6-dien-1-yl)-2,4-dihydroxy-N-methyl-6-pentylbenzenesulfonamide (9% yield) as a white solid. $^1$H NMR (400 MHz, CDCl$_3$) δ 10.30 (s, 1H), 6.39 (s, 1H), 5.91 (s, 1H), 5.29 (t, J=6.9 Hz, 1H), 5.07 (d, J=7.5 Hz, 1H), 4.40 (d, J=5.7 Hz, 1H), 3.45 (d, J=7.1 Hz, 2H), 2.87-2.79 (m, 2H), 2.66 (d, J=5.4 Hz, 3H), 2.15-2.07 (m, 4H), 1.83 (s, 3H), 1.74-1.62 (m, 8H), 1.40-1.38 (m, 4H), 0.97-0.89 (m, 3H). ESI-MS [M+H]+: 410.3.

Example 2: 3-(3,7-dimethylocta-2,6-dien-1-yl)-2,4-dihydroxy-N-isopropyl-6-pentylbenzenesulfonamide (23)

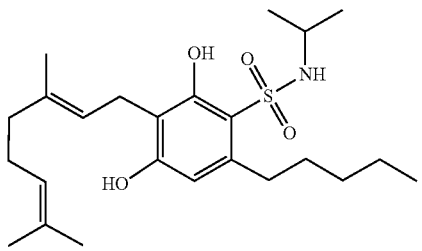 [SMILES: CCCCCc1cc(O)c(C/C=C(\C)CCC=C(C)C)c(O)c1S(=O)(=O)NC(C)C]

The procedures of Example 1 steps a and b were followed to provide 2,4-dimethoxy-6-pentylbenzenesulfonyl chloride.

N-isopropyl-2,4-dimethoxy-6-pentyl-benzenesulfonamide was prepared from 2,4-dimethoxy-6-pentyl-benzenesulfonyl chloride using the procedures described in Example 1, step c, and using isopropyalmine in place of methylamine. ¹H NMR (400 MHz, CDCl₃) δ 6.46-6.39 (m, 2H), 5.09 (s, 1H), 3.96 (s, 3H), 3.87 (s, 3H), 3.43 (s, 1H), 3.12-3.03 (m, 2H), 1.75-1.61 (m, 2H), 1.39 (m, 4H), 1.09 (d, J=6.5 Hz, 6H), 0.97-0.84 (m, 3H).

2,4-dihydroxy-N-isopropyl-6-pentyl-benzenesulfonamide was prepared from N-isopropyl-2,4-dimethoxy-6-pentyl-benzenesulfonamide using the procedures described in Example 1, step d, and was isolated as a yellow oil (60% yield). ¹H NMR (400 MHz, CDCl₃) δ 10.12 (s, 1H), 6.45-6.35 (m, 1H), 6.31 (d, J=2.6 Hz, 1H), 5.56 (s, 1H), 4.36 (d, J=7.8 Hz, 1H), 3.45 (m, 1H), 2.89-2.81 (m, 2H), 1.68 (m, 2H), 1.39 (m, 4H), 1.13 (d, J=6.5 Hz, 6H), 0.98-0.87 (m, 3H).

(E)-3-(3,7-dimethylocta-2,6-dien-1-yl)-2,4-dihydroxy-N-isopropyl-6-pentylbenzenesulfonamide was prepared from 2,4-dihydroxy-N-isopropyl-6-pentyl-benzenesulfonamide using the procedures described in Example 1, step e, and was isolated as a white solid (3% yield). ¹H NMR (400 MHz, CD₃CN) δ 6.25 (s, 1H), 5.04-5.01 (m, 1H), 5.95-4.92 (m, 1H), 3.27-3.21 (3H, m), 2.79-2.74 (m, 2H), 2.05-1.99 (4H, m), 1.71 (s, 3H), 1.67-1.47 (m, 8H), 1.40-1.29 (m, 4H), 1.03 (d, J=6.4 Hz, 6H), 0.94 (t, J=7.0 Hz, 3H).

ESI-MS [M+H]+: 438.3.

Example 3: N-cyclohexyl-3-(3,7-dimethylocta-2,6-dien-1-yl)-2,4-dihydroxy-6-pentylbenzenesulfonamide (62)

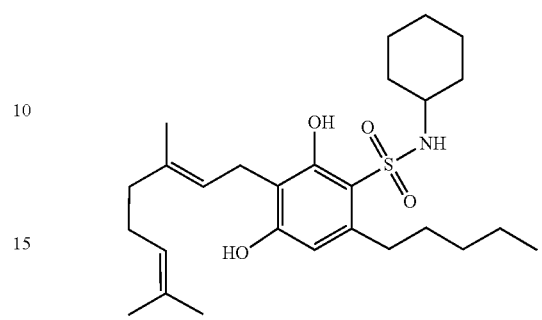

The procedures of Example 1 steps a and b were followed to provide 2,4-dimethoxy-6-pentylbenzenesulfonyl chloride.

N-cyclohexyl-2,4-dimethoxy-6-pentyl-benzenesulfonamide was prepared from 2,4-dimethoxy-6-pentyl-benzenesulfonyl chloride using the procedures described in Example 1, step c, and using cyclohexylamine in place of methylamine (white solid, 62% yield). ¹H NMR (400 MHz, CDCl₃) δ 6.46-6.37 (m, 2H), 5.20 (d, J=7.2 Hz, 1H), 3.95 (s, 3H), 3.87 (s, 3H), 3.16 (m, 1H), 3.11-3.04 (m, 2H), 1.76-1.14 (m, 16), 0.93 (m, 3H).

N-cyclohexyl-2,4-dihydroxy-6-pentyl-benzenesulfonamide was prepared from N-cyclohexyl-2,4-dimethoxy-6-pentyl-benzenesulfonamide using the procedures described in Example 1, step d, and was isolated as a yellow oil (61% yield). ¹H NMR (400 MHz, CDCl₃) δ 10.13 (s, 1H), 6.38 (d, J=2.6 Hz, 1H), 6.31 (d, J=2.6 Hz, 1H), 5.44 (s, 1H), 4.44 (d, J=7.9 Hz, 1H), 3.16-3.10 (1H, m), 2.90-2.82 (m, 2H), 1.80-1.14 (m, 16H), 0.98-0.91 (m, 3H).

(E)-N-cyclohexyl-3-(3,7-dimethylocta-2,6-dien-1-yl)-2,4-dihydroxy-6-pentylbenzenesulfonamide was prepared from N-cyclohexyl-2,4-dihydroxy-6-pentyl-benzenesulfonamide using the procedures described in Example 1, step e, and was isolated as a yellowish liquid (8% yield). ¹H NMR (400 MHz, CDCl₃) δ 10.37 (s, 1H), 6.35 (s, 1H), 5.84 (s, 1H), 5.27-5.24 (m, 1H), 5.07-5.04 (m, 1H), 4.40 (d, J=7.9 Hz, 1H), 3.43 (d, J=7.1 Hz, 2H), 3.14-3.05 (m, 1H), 2.83-2.79 (m, 2H), 2.11-2.04 (m, 4H), 1.80 (s, 3H), 1.78-1.11 (m, 22H), 0.92-0.89 (m, 3H). ESI-MS [M+H]+: 478.3.

Example 4: 3-(3,7-dimethylocta-2,6-dien-1-yl)-2,4-dihydroxy-6-pentyl-N-phenylbenzenesulfonamide (24)

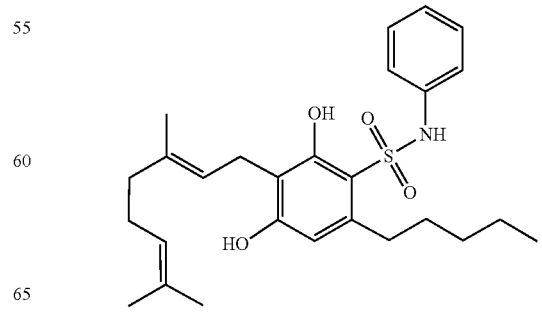

The procedures of Example 1 steps a and b were followed to provide 2,4-dimethoxy-6-pentylbenzenesulfonyl chloride.

2,4-dimethoxy-6-pentyl-N-phenyl-benzenesulfonamide was prepared from 2,4-dimethoxy-6-pentyl-benzenesulfonyl chloride using the procedures describe in Example 1, step c, and using aniline in place of methylamine (white solid, 52% yield). $^1$H NMR (400 MHz, CDCl$_3$) δ 7.26-7.15 (m, 3H), 7.13-7.07 (m, 2H), 6.42 (d, J=2.4 Hz, 1H), 6.31 (d, J=2.5 Hz, 1H), 4.05 (s, 3H), 3.82 (s, 3H), 2.99-2.86 (m, 2H), 1.39 (s, 2H), 1.31-1.27 (m, 4H), 0.91-0.84 (m, 3H).

2,4-dihydroxy-6-pentyl-N-phenyl-benzenesulfonamide was prepared from 2,4-dimethoxy-6-pentyl-N-phenyl-benzenesulfonamide using the procedures described in Example 1, step d, and was isolated as a yellow oil (60% yield). $^1$H NMR (400 MHz, CDCl$_3$) δ 9.79 (s, 1H), 7.32-7.26 (m, 2H), 7.18 (t, J=7.4 Hz, 1H), 6.99 (dd, J=7.4, 1.6 Hz, 2H), 6.57 (s, 1H), 6.34 (d, J=2.6 Hz, 1H), 6.26 (d, J=2.6 Hz, 1H), 5.34 (s, 1H), 2.88-2.82 (m, 2H), 1.68-1.62 (m, 2H), 1.39 (dq, J=6.7, 3.3 Hz, 4H), 0.93 (t, J=7.0 Hz, 3H).

(E)-3-(3,7-dimethylocta-2,6-dien-1-yl)-2,4-dihydroxy-6-pentyl-N-phenylbenzenesulfonamide was prepared from 2,4-dihydroxy-6-pentyl-N-phenyl-benzenesulfonamide using the procedures described in Example 1, step e, and was isolated as a yellowish liquid (14% yield). $^1$H NMR (400 MHz, CDCl$_3$) δ 10.05 (s, 1H), 7.29-7.25 (m, 2H), 7.19-7.13 (m, 1H), 7.00-6.95 (m, 2H), 6.63 (s, 1H), 6.34 (s, 1H), 5.88 (s, 1H), 5.23-5.18 (m, 1H), 5.09-5.06 (m, 1H), 3.39 (d, J=7.1 Hz, 2H), 2.85-2.81 (m, 2H), 2.15-2.05 (m, 4H), 1.79 (s, 3H), 1.70 (s, 3H), 1.62-1.58 (m, 5H), 1.41-1.32 (m, 4H), 0.94-0.90 (m, 3H). ESI-MS [M+H]$^+$: 472.3.

Example 5: N-cyclobutyl-3-(3,7-dimethylocta-2,6-dien-1-yl)-2,4-dihydroxy-6-pentylbenzenesulfonamide (63)

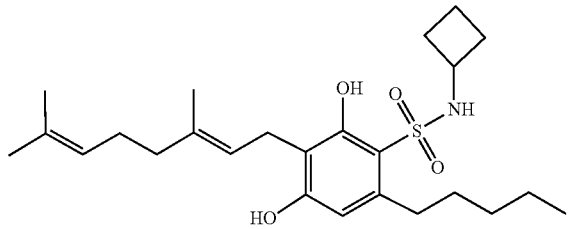 [SMILES: CCCCCc1cc(O)c(C/C=C(\C)CCC=C(C)C)c(O)c1S(=O)(=O)NC1CCC1]

The procedures of Example 1 steps a and b were followed to provide 2,4-dimethoxy-6-pentylbenzenesulfonyl chloride.

N-cyclobutyl-2,4-dimethoxy-6-pentyl-benzenesulfonamide was prepared from 2,4-dimethoxy-6-pentylbenzenesulfonyl chloride using the procedures described in Example 1, step c, and using cyclobytylamine in place of methylamine (white solid, 90% yield). $^1$H NMR (400 MHz, CDCl$_3$) δ 6.42 (d, J=2.5 Hz, 1H), 6.39 (d, J=2.5 Hz, 1H), 5.45 (d, J=9.2 Hz, 1H), 3.97 (s, 3H), 3.85 (s, 3H), 3.81-3.76 (m, 1H), 3.10-3.02 (m, 2H), 2.05-2.03 (m, 2H), 1.79-1.52 (m, 6H), 1.40-1.37 (m, 4H), 0.92 (t, J=6.9 Hz, 3H). ESI-MS [M–H]$^-$: 340.20.

N-cyclobutyl-2,4-dihydroxy-6-pentyl-benzenesulfonamide was prepared from N-cyclobutyl-2,4-dimethoxy-6-pentyl-benzenesulfonamide using the procedures described in Example 1, step d, and was isolated as a transparent oil (63% yield). $^1$H NMR (400 MHz, CDCl$_3$) δ 10.01 (s, 1H), 7.56 (s, 1H), 6.37 (d, J=2.5 Hz, 1H), 6.31 (d, J=2.5 Hz, 1H), 5.15 (d, J=8.7 Hz, 1H), 3.71-3.65 (m, 1H), 2.85-2.76 (m, 2H), 2.16-2.09 (m, 2H), 1.93-1.78 (m, 2H), 1.72-1.51 (m, 4H), 1.36-1.34 (m, 4H), 0.89 (t, J=7.0 Hz, 3H). ESI-MS [M+H]$^+$: 314.20.

(E)-N-cyclobutyl-3-(3,7-dimethylocta-2,6-dien-1-yl)-2,4-dihydroxy-6-pentylbenzenesulfonamide was prepared from N-cyclobutyl-2,4-dihydroxy-6-pentyl-benzenesulfonamide using the procedures described in Example 1, step e, and was isolated as a white solid (3% yield). $^1$H NMR (400 MHz, CDCl$_3$) δ 10.29 (s, 1H), 6.36 (s, 1H), 5.88 (s, 1H), 5.27 (t, J=7.1 Hz, 1H), 5.08 (t, J=7.4 Hz, 1H), 4.67 (d, J=6.2 Hz, 1H), 3.79-3.66 (m, 1H), 3.45 (d, J=7.1 Hz, 2H), 2.85-2.77 (m, 2H), 2.21-2.06 (m, 4H), 1.80-1.66 (m, 15H), 1.40-1.39 (m, 6H), 0.93 (t, J=7.0 Hz, 3H). ESI-MS [M–H]$^-$: 448.30.

Example 6: 3-(3,7-dimethylocta-2,6-dien-1-yl)-N-hexyl-2,4-dihydroxy-6-pentylbenzenesulfonamide (64)

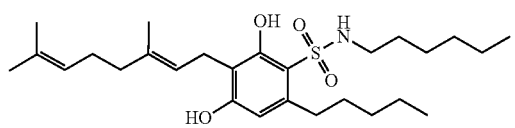 [SMILES: CCCCCCNS(=O)(=O)c1c(CCCCC)cc(O)c(C/C=C(\C)CCC=C(C)C)c1O]

The procedures of Example 1 steps a and b were followed to provide 2,4-dimethoxy-6-pentylbenzenesulfonyl chloride.

N-hexyl-2,4-dimethoxy-6-pentyl-benzenesulfonamide was prepared from 2,4-dimethoxy-6-pentylbenzenesulfonyl chloride using the procedures described in Example 1, step c, and using hexylamine in place of methylamine (transparent oil, 93% yield). $^1$H NMR (400 MHz, CDCl$_3$) δ 6.43-6.41 (m, 2H), 5.19 (t, J=6.2 Hz, 1H), 3.95 (s, 3H), 3.86 (s, 3H), 3.11-3.02 (m, 2H), 2.88 (q, J=6.8 Hz, 2H), 1.72-1.58 (m, 2H), 1.57-1.42 (m, 2H), 1.42-1.18 (m, 10H), 0.93-0.85 (m, 6H). ESI-MS [M+H]$^+$: 372.28.

N-hexyl-2,4-dihydroxy-6-pentyl-benzenesulfonamide was prepared from N-hexyl-2,4-dimethoxy-6-pentyl-benzenesulfonamide using the procedures described in Example 1, step d, and was isolated as a yellow oil (76% yield). $^1$H NMR (400 MHz, CDCl$_3$) δ 10.06 (s, 1H), 6.38 (d, J=2.6 Hz, 1H), 6.31 (d, J=2.6 Hz, 1H), 5.48 (s, 1H), 4.43 (s, 1H), 2.94 (q, J=6.8 Hz, 2H), 2.88-2.83 (m, 2H), 1.72-1.60 (m, 4H), 1.53-1.24 (m, 1OH), 0.95-0.86 (m, 6H).

ESI-MS [M–H]$^-$: 342.20.

(E)-3-(3,7-dimethylocta-2,6-dien-1-yl)-N-hexyl-2,4-dihydroxy-6-pentylbenzenesulfonamide was prepared from N-hexyl-2,4-dihydroxy-6-pentyl-benzenesulfonamide using the procedures described in Example 1, step e, and was isolated as a white solid (5.5% yield). $^1$H NMR (400 MHz, CDCl$_3$) δ 10.33 (s, 1H), 6.37 (s, 1H), 5.94 (s, 1H), 5.27 (t, J=6.6 Hz, 1H), 5.10-5.06 (m, 1H), 4.46-4.42 (m, 1H), 3.44 (d, J=7.1 Hz, 2H), 2.97-2.81 (m, 4H), 2.14-2.07 (m, 4H), 1.82 (s, 3H), 1.70 (s, 3H), 1.61 (s, 3H), 1.72-1.63 (2H, m), 1.49-1.23 (m, 12H), 0.95-0.86 (m, 6H). ESI-MS [M+H]$^+$: 480.40.

Example 7: N-allyl-3-(3,7-dimethylocta-2,6-dien-1-yl)-2,4-dihydroxy-6-pentylbenzenesulfonamide (65)

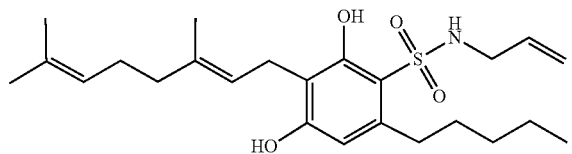 [SMILES: C=CCNS(=O)(=O)c1c(CCCCC)cc(O)c(C/C=C(\C)CCC=C(C)C)c1O]

The procedures of Example 1 steps a and b were followed to provide 2,4-dimethoxy-6-pentylbenzenesulfonyl chloride.

N-allyl-2,4-dimethoxy-6-pentyl-benzenesulfonamide was prepared from 2,4-dimethoxy-6-pentylbenzenesulfonyl chloride using the procedures described in Example 1, step c, and using allylamine in place of methylamine (white solid, 93% yield). $^1$H NMR (400 MHz, CDCl$_3$) δ 6.41 (d, J=2.4 Hz, 1H), 6.39 (d, J=2.4 Hz, 1H), 5.77-5.67 (m, 1H), 5.33-5.26 (m, 1H), 5.18-5.13 (m, 1H), 5.08-5.04 (m, 1H), 3.92 (s, 3H), 3.84 (s, 3H), 3.52 (t, J=6.1 Hz, 2H), 3.07-2.98 (m, 2H), 1.67-1.59 (m, 2H), 1.35-1.34 (m, 4H), 0.88 (t, J=7.0 Hz, 3H). ESI-MS [M−H]$^-$: 326.20.

N-allyl-2,4-dihydroxy-6-pentyl-benzenesulfonamide was prepared from N-allyl-2,4-dimethoxy-6-pentyl-benzenesulfonamide using the procedures described in Example 1, step d, and was isolated as a yellow oil (92% yield). $^1$H NMR (400 MHz, CDCl$_3$) δ 9.98 (s, 1H), 7.15 (s, 1H), 6.39 (d, J=2.6 Hz, 1H), 6.32 (d, J=2.6 Hz, 1H), 5.79-5.71 (m, 1H), 5.21 (d, J=18.1 Hz, 1H), 5.14 (d, J=12.4 Hz, 1H), 4.75 (s, 1H), 3.57 (t, J=5.8 Hz, 2H), 2.90-2.79 (m, 2H), 1.71-1.59 (m, 2H), 1.38 (m, 4H), 0.91 (t, J=5.9 Hz, 3H). ESI-MS [M+H]$^+$: 300.20.

(E)-N-allyl-3-(3,7-dimethylocta-2,6-dien-1-yl)-2,4-dihydroxy-6-pentylbenzenesulfonamide was prepared from N-allyl-2,4-dihydroxy-6-pentyl-benzenesulfonamide using the procedures described in Example 1, step e, and was isolated as a white solid (6.1% yield). $^1$H NMR (400 MHz, CDCl$_3$) δ 10.28 (s, 1H), 6.37 (s, 1H), 5.91 (s, 1H), 5.80-5.70 (m, 1H), 5.29-5.06 (m, 4H), 4.52 (t, J=5.7 Hz, 1H), 3.61-3.56 (m, 2H), 3.44 (d, J=7.1 Hz, 2H), 2.92-2.82 (m, 2H), 2.14-2.07 (m, 4H), 1.83 (s, 3H), 1.72-1.52 (m, 8H), 1.45-1.37 (m, 4H), 0.96-0.90 (m, 3H). ESI-MS [M+H]$^+$: 436.30.

Example 8: 2-(3,7-dimethylocta-2,6-dien-1-yl)-4-(morpholinosulfonyl)-5-pentylbenzene-1,3-diol (28)

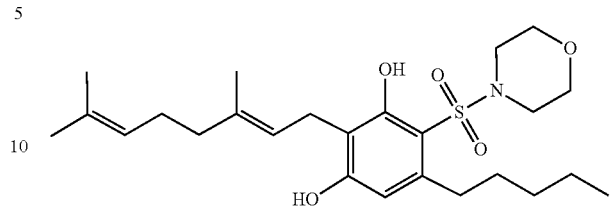

The procedures of Example 1 steps a and b were followed to provide 2,4-dimethoxy-6-pentylbenzenesulfonyl chloride.

4-(2,4-dimethoxy-6-pentyl-phenyl)sulfonylmorpholine was prepared from 2,4-dimethoxy-6-pentylbenzenesulfonyl chloride using the procedures described in Example 1, step c, and using morpholine in place of methylamine (white solid, 90% yield). $^1$H NMR (400 MHz, CDCl$_3$) δ 6.41 (d, J=2.5 Hz, 1H), 6.39 (d, J=2.5 Hz, 1H), 3.90 (s, 3H), 3.87 (s, 3H), 3.79-3.70 (m, 4H), 3.34-3.24 (m, 4H), 3.07-2.98 (m, 2H), 1.72-1.61 (m, 2H), 1.47-1.32 (m, 4H), 0.92 (t, J=6.9 Hz, 3H). ESI-MS [M+H]$^+$: 358.20.

4-morpholinosulfonyl-5-pentyl-benzene-1,3-diol was prepared from 4-(2,4-dimethoxy-6-pentyl-phenyl)sulfonylmorpholine using the procedures described in Example 1, step d, and was isolated as a yellow oil (13% yield). $^1$H NMR (400 MHz, CDCl$_3$) δ 9.99 (s, 1H), 6.39 (d, J=2.6 Hz, 1H), 6.31 (d, J=2.6 Hz, 1H), 6.18 (s, 1H), 3.80-3.71 (m, 4H), 3.22-3.16 (m, 4H), 2.88-2.81 (m, 2H), 1.69-1.59 (m, 2H), 1.39-1.37 (m, 4H), 0.93 (t, J=7.0 Hz, 3H).
ESI-MS [M+H]$^+$: 330.197.

(E)-2-(3,7-dimethylocta-2,6-dien-1-yl)-4-(morpholinosulfonyl)-5-pentylbenzene-1,3-diol was prepared from 4-morpholinosulfonyl-5-pentyl-benzene-1,3-diol using the procedures described in Example 1, step e, and was isolated as a white solid (9% yield). $^1$H NMR (400 MHz, CDCl$_3$) δ 10.29 (s, 1H), 6.39 (s, 1H), 5.94 (s, 1H), 5.28 (t, J=6.8 Hz, 1H), 5.08 (t, J=7.1 Hz, 1H), 3.77-3.72 (m, 4H), 3.44 (d, J=7.2 Hz, 2H), 3.21-3.14 (m, 4H), 2.86-2.79 (m, 2H), 2.20-2.05 (m, 4H), 1.83 (s, 3H), 179-1.61 (m, 8H), 1.42-1.34 (m, 4H), 0.94 (t, J=6.9 Hz, 3H). ESI-MS [M+H]$^+$: 466.30.

Example 9: 3-(3,7-dimethylocta-2,6-dien-1-yl)-2,4-dihydroxy-6-pentyl-N-(phenylsulfonyl)benzamide (58)

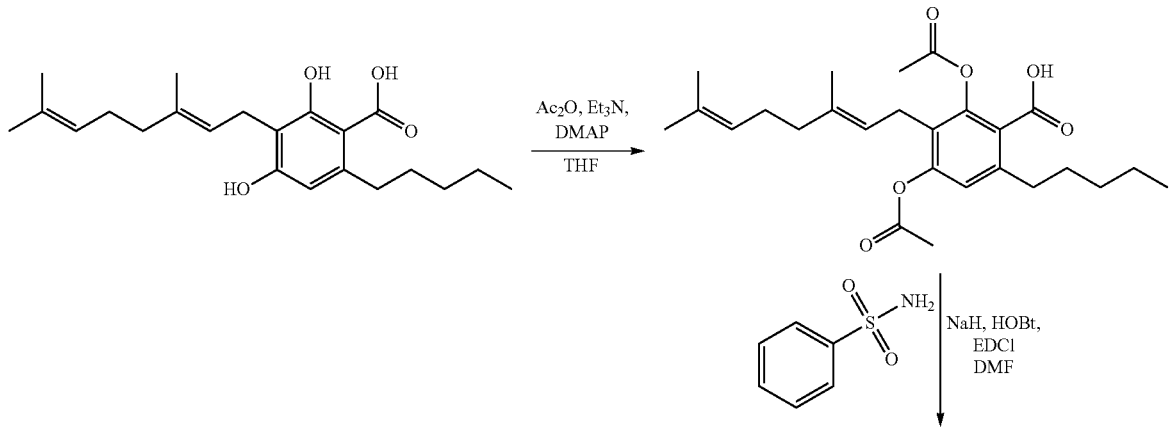

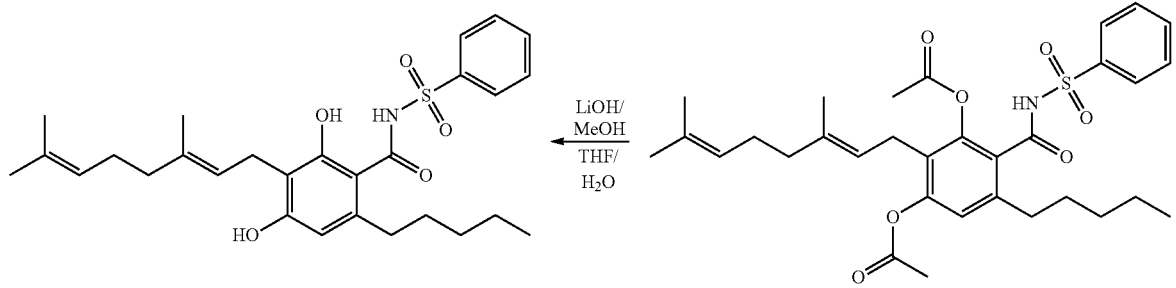

To a stirred solution of (E)-3-(3,7-dimethylocta-2,6-dien-1-yl)-2,4-dihydroxy-6-pentylbenzoic acid (cannabigerolic acid; 400 mg, 1.11 mmol) and 4-Dimethylaminopyridine (DMAP; 6.8 mg, 0.055 mmol) in tetrahydrofuran (THF; 5 mL) under $N_2$ was added triethylamine (773 µL, 5.55 mmol), followed by acetic anhydride (230 µL, 2.44 mmol) dropwise. After stirring at room temperature for 1 h, the mixture was quenched with water and extracted with ethyl acetate. The organic extract was washed with brine, followed by water and 1N HCl. The organic phase was dried over $Na_2SO_4$, filtered and concentrated. The crude mixture was purified by flash column chromatography on silica gel (ethyl acetate –hexane) to give (E)-2,4-diacetoxy-3-(3,7-dimethyl-octa-2,6-dien-1-yl)-6-pentylbenzoic acid (63% yield). $^1$H NMR (400 MHz, $CD_3CN$) δ 6.97 (s, 1H), 5.11-5.07 (m, 1H), 5.01-4.98 (m, 1H), 3.16 (d, J=7.7 Hz, 2H), 2.73-2.65 (m, 2H), 2.28 (s, 3H), 2.24 (s, 3H), 2.09-2.02 (m, 2H), 2.00-1.95 (m, 2H), 1.73 (s, 3H), 1.66 (s, 3H), 1.60 (m, 5H), 1.41-1.27 (m, 4H), 0.96-0.87 (m, 3H). ESI-MS [M–H]$^-$443.3.

To a stirred solution of benzenesulfonamide (177 mg, 1.12 mmol) in dimethylformamide (DMF; 5 mL) under $N_2$ was added sodium hydride (27 mg, 1.12 mmol) portionwise. Meanwhile a solution of (E)-2,4-diacetoxy-3-(3,7-dimethylocta-2,6-dien-1-yl)-6-pentylbenzoic acid (100 mg, 0.225 mmol) and 1-hydroxybenzotriazole hydrate (52 mg, 0.34 mmol) in DMF (2 mL) under $N_2$ was treated with 1-ethyl-3-(3-dimethylaminopropyl)carbodiimide (EDCl; 65 mg, 0.34 mmol) and the mixture was stirred at room temperature for 2 h. The solution of the activated acid was added to the suspension of the sulfonamide anion slowly and the mixture was stirred for 1 h. The mixture was quenched with water and extracted with ethyl acetate. The organic extract was washed with brine, followed by water and 1N HCl. The organic phase was dried, filtered and concentrated. The crude mixture was purified by flash column chromatography on silica gel (ethyl acetate –hexane) to give (E)-2-(3,7-dimethylocta-2,6-dien-1-yl)-5-pentyl-4-((phenylsulfonyl)carbamoyl)-1,3-phenylene diacetate (9.1% yield). ESI-MS [M–H]$^-$582.3.

To a stirred solution of (E)-2-(3,7-dimethylocta-2,6-dien-1-yl)-5-pentyl-4-((phenylsulfonyl)carbamoyl)-1,3-phenylene diacetate (12 mg, 0.021 mmol) in methanol (0.5 mL) was added a solution of lithium hydroxide monohydrate (4.3 mg, 0.10 mmol) in $H_2O$ (0.1 mL). THF (0.5 mL) was added to aid solubility. The resulting mixture was stirred at room temperature overnight. The mixture was diluted with water, neutralized with 1N HCl and extracted with DCM. The organic phase was dried over $Na_2SO_4$, filtered and concentrated. The crude mixture was purified by flash column chromatography on silica gel (ethyl acetate –hexane) to give (E)-3-(3,7-dimethylocta-2,6-dien-1-yl)-2,4-dihydroxy-6-pentyl-N-(phenylsulfonyl)benzamide (4% yield).

Example 10: 3-(3,7-dimethylocta-2,6-dien-1-yl)-2,4-dihydroxy-6-pentyl-N-(pyridin-3-ylsulfonyl)benzamide (66)

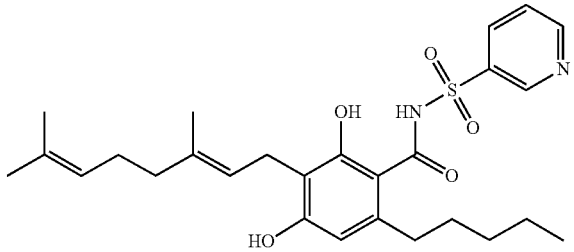 [SMILES: CCCCCc1cc(O)c(C/C=C(\C)CCC=C(C)C)c(O)c1C(=O)NS(=O)(=O)c1cccnc1]

(E)-3-(3,7-dimethylocta-2,6-dien-1-yl)-2,4-dihydroxy-6-pentyl-N-(pyridin-3-ylsulfonyl)benzamide was prepared as described in Example 9, using pyridine-3-sulfonamide in place of benzenesulfonamide (12% yield). $^1$H NMR (400 MHz, $CD_3CN$) δ 9.19 (s, 1H), 8.87 (d, J=4.9 Hz, 1H), 8.40-8.37 (m, 1H), 7.61 (dd, J=8.1, 4.8 Hz, 1H), 7.24 (s, 1H), 6.28 (s, 1H), 5.14-5.07 (m, 2H), 3.26 (d, J=7.0 Hz, 2H), 2.52-2.48 (m, 2H), 2.13-2.00 (m, 4H), 1.76 (s, 3H), 1.64 (s, 3H), 1.593 (s, 3H), 1.39-1.15 (m, 6H), 0.88 (t, J=7.2 Hz, 3H). ESI-MS [M–H]$^-$=499.3.

Example 11: 2-(3,7-dimethylocta-2,6-dien-1-yl)-4-(methylsulfonyl)-5-pentylbenzene-1,3-diol

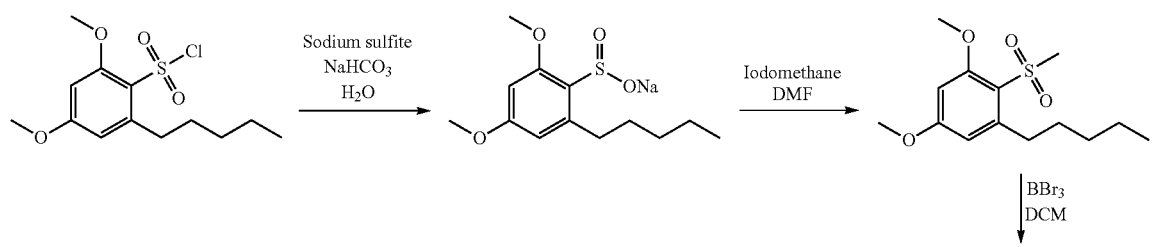

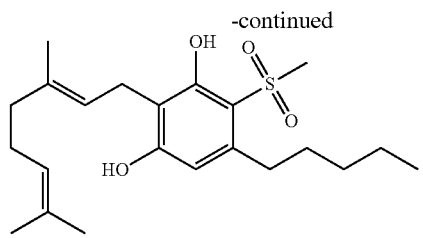
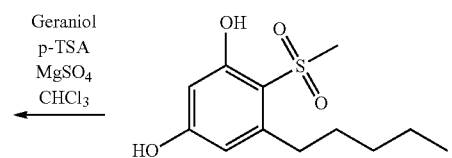

2,4-dimethoxy-6-pentyl-benzenesulfonyl chloride (1.00 g, 3.26 mmol) was added to a solution of sodium sulfite (1.63 g, 12.93 mmol) and sodium bicarbonate (1.09 g, 12.98 mmol) in H$_2$O (16 mL) at room temperature. The reaction mixture was stirred at 70° C. for 12 h and solvent was evaporated under reduced pressure. The resulting solid was suspended in ethanol (10 mL) and stirred for 20 min at room temperature. The mixture was filtered and the filtrate was concentrated to give sodium 2,4-dimethoxy-6-pentylbenzenesulfinate (892 mg, 3.03 mmol, 93% yield) as a white solid: $^1$H NMR (400 MHz, CDCl$_3$) δ 6.17 (d, J=2.3 Hz, 1H), 6.11 (d, J=2.3 Hz, 1H), 3.75 (s, 3H), 3.54 (s, 3H), 2.78 (t, J=7.9 Hz, 2H), 1.59 (m, 2H), 1.33-1.22 (m, 4H), 0.97-0.82 (m, 3H).

In a 10 mL microwave vial was added sodium 2,4-dimethoxy-6-pentylbenzenesulfinate (200 mg, 0.68 mmol) and dry DMF (3 mL) under argon atmosphere. The solution was stirred at room temperature and iodomethane (85 µL, 1.36 mmol) was added dropwise. The mixture was stirred at 80° C. for 12 h. Water was added, and the mixture was extracted with ethyl acetate. The combined organic layers were washed with brine, dried over Na$_2$SO$_4$, concentrated and purified by flash column chromatography using ethyl acetate—hexane to give 1,5-dimethoxy-2-methylsulfonyl-3-pentyl-benzene (187 mg, 0.65 mmol, 96% yield) as a yellow oil: $^1$H NMR (400 MHz, CDCl$_3$) δ 6.44 (s, 1H), 6.39 (s, 1H), 3.96 (s, 3H), 3.86 (s, 3H), 3.23 (s, 3H), 3.11-3.06 (m, 2H), 1.66-1.62 (m, 2H), 1.39-1.32 (m, 4H), 0.92-0.89 (m, 3H). ESI-MS [M+H]$^+$: 287.1.

To a solution of 1,5-dimethoxy-2-methylsulfonyl-3-pentyl-benzene (187 mg, 0.62 mmol) in DCM (3 mL) at −78° C. was added boron tribromide (1 M, 3.08 mL) dropwise. The mixture was stirred at room temperature for 12 h, quenched with 1M HCl and extracted with DCM. The organic layer was washed with brine, dried over Na$_2$SO$_4$, concentrated and purified by flash column chromatography using ethyl acetate—hexane to give 4-methylsulfonyl-5-pentyl-benzene-1,3-diol (101 mg, 0.39 mmol, 63% yield) as a brown oil: $^1$H NMR (400 MHz, CDCl$_3$) δ 10.01 (s, 1H), 7.06 (s, 1H), 6.36 (d, J=2.7 Hz, 1H), 6.30 (d, J=2.6 Hz, 1H), 3.14 (s, 3H), 2.84-2.80 (m, 2H), 1.65-1.61 (m, 2H), 1.38-1.32 (m, 4H), 0.90-0.85 (m, 3H). ESI-MS [M−H]$^-$: 257.1.

In a dry and argon-purged round-bottom flask sealed with a rubber cork and fitted with a stir bar, 4-methylsulfonyl-5-pentyl-benzene-1,3-diol (100 mg, 0.39 mmol) was charged followed by the addition of chloroform (3 mL) and anhydrous MgSO$_4$ (140 mg, 1.16 mmol). The flask was placed in an ice bath and cooled for 10 min. p-Toluenesulfonic acid monohydrate (7.4 mg, 0.039 mmol) was added and the reaction mixture was stirred for 10 min. Geraniol (119 mg, 0.77 mmol) was added and the reaction was stirred in an ice bath for additional 30 min. After stirring at room temperature for 18 h, the reaction mixture was quenched with sat. NaHCO$_3$ and the organic layer was washed with sat. NaHCO$_3$ and brine. The organic extract was dried over Na$_2$SO$_4$, concentrated and purified by C$_{18}$ reverse phase chromatography (CH$_3$CN—H$_2$O) to give (E)-2-(3,7-dimethylocta-2,6-dien-1-yl)-4-(methylsulfonyl)-5-pentylbenzene-1,3-diol (2% yield) as an oil. $^1$H NMR (400 MHz, CDCl$_3$) δ 10.31 (s, 1H), 6.35 (s, 1H), 5.90 (s, 1H), 5.27 (t, J=6.7 Hz, 1H), 5.06-5.03 (m, 1H), 3.41 (d, J=7.1 Hz, 2H), 3.14 (s, 3H), 2.84-2.80 (m, 2H), 2.12-2.05 (m, 4H), 1.80 (s, 3H), 1.76-1.59 (m, 8H), 1.40-1.34 (m, 4H), 0.90 (t, J=7.0 Hz, 3H). ESI-MS [M−H]$^-$: 393.2.

Example 12: phenyl-3-(3,7-dimethylocta-2,6-dien-1-yl)-2,4-dihydroxy-6-pentylbenzenesulfonate (67)

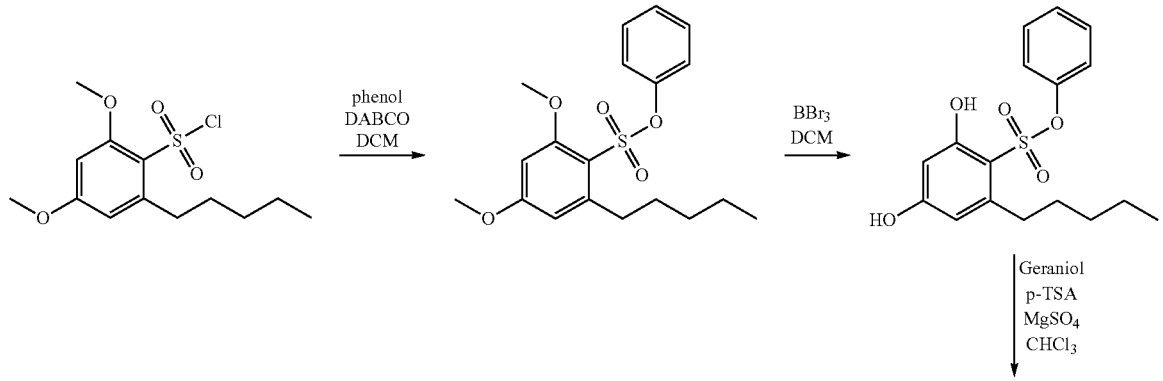

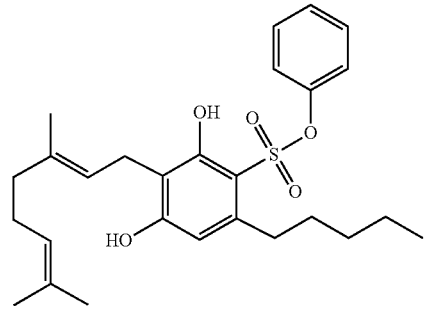

To a dried 25 mL round-bottom flask, charged with 2,4-dimethoxy-6-pentyl-benzenesulfonyl chloride (350 mg, 1.14 mmol) in DCM (6 mL) was added phenol (128.83 mg, 1.37 mmol). To the resulting solution was added dropwise a solution of 1,4-diazabicyclo[2.2.2]octane (DABCO; 128 mg, 1.14 mmol) in DCM (3 mL). The reaction was stirred at room temperature for 2 h and monitored by TLC. The reaction mixture was then quenched with 0.1 N HCl and extracted with DCM. The organic layers were combined, dried over $Na_2SO_4$, filtered and concentrated. The crude was purified by flash column chromatography on silica gel (ethyl acetate—hexane) to yield phenyl 2,4-dimethoxy-6-pentyl-benzenesulfonate as a clear oil (304 mg, 73% yield).

To a microwave vial charged with phenyl 2,4-dimethoxy-6-pentylbenzenesulfonate (301 mg, 0.825 mmol) in DCM (1.5 mL) was added boron tribromide (1M, 2.06 mL) dropwise. The resulting mixture was stirred at room temperature for 12 h and quenched with aq. $NaHCO_3$. The mixture was diluted with NaOH 1N and extracted with both DCM and ethyl acetate. The aqueous phase was then acidified using 1M HCl and extracted with DCM and ethyl acetate. The combined organic layers were washed with brine, dried over $Na_2SO_4$, filtered and concentrated. The obtained crude was purified via flash column chromatography on silica gel (ethyl acetate—hexane) to yield phenyl 2,4-dihydroxy-6-pentylbenzenesulfonate (201 mg, 72% yield). $^1$H NMR (400 MHz, $CDCl_3$) δ 7.31-7.26 (m, 3H), 7.01-6.99 (m, 2H), 6.43-6.42 (m, 1H), 6.21-6.20 (m, 1H), 2.98-2.94 (m, 2H), 1.72-1.64 (m, 2H), 1.45-1.33 (m, 4H), 0.91 (t, J=7.0 Hz, 3H).

To a dried microwave vial purged with argon and charged with phenyl 2,4-dihydroxy-6-pentyl-benzenesulfonate (200 mg, 0.59 mmol) in anhydrous chloroform (2.5 mL) was added magnesium sulfate (286 mg, 2.38 mmol), followed by p-toluenesulfonic acid monohydrate (11 mg, 0.059 mmol). The reaction mixture was cooled to 0C and stirred for 10 min Geraniol (183 mg, 1.19 mmol) was added dropwise and the resulting mixture was stirred at room temperature overnight. The reaction mixture was quenched with aq. $NaHCO_3$ and extracted with DCM. The organic extract was dried over $Na_2SO_4$, filtered and concentrated. The crude mixture was purified by flash column chromatography on silica gel (ethyl acetate—hexane), followed by 018 reverse phase chromatography ($CH_3CN$—$H_2O$) to yield phenyl-(E)-3-(3,7-dimethylocta-2,6-dien-1-yl)-2,4-dihydroxy-6-pentylbenzenesulfonate as a clear oil (6.5% yield). $^1$H NMR (400 MHz, $0001_3$) b 9.46 (s, 1H), 7.36-7.29 (m, 3H), 7.05-7.01 (m, 2H), 6.44 (s, 1H), 5.99 (s, 1H), 5.21-5.12 (m, 1H), 5.12-5.04 (m, 1H), 3.35 (d, J=7.1 Hz, 2H), 2.99-2.92 (m, 2H), 2.09 (m, 4H), 1.78 (s, 3H), 1.74-1.62 (m, 8H), 1.47-1.33 (m, 4H), 0.93 (t, J=7.0 Hz, 3H). ESI-MS [M–H]$^-$: 471.24.

Example 13

The following compounds may be prepared according to the procedures known to those of skill in the art in view of Schemes 1-6 and Examples 1-12:

| Comp. No. | Name | Structure |
|---|---|---|
| 1 | 3-(3,7-dimethylocta-2,6-dien-1-yl)-2,4-dihydroxy-6-pentylbenzenesulfonic acid | 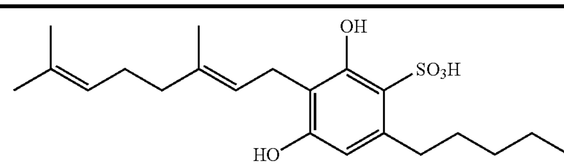 |
| 2 | sodium 3-(3,7-dimethylocta-2,6-dien-1-yl)-2,4-dihydroxy-6-pentylbenzenesulfonate | 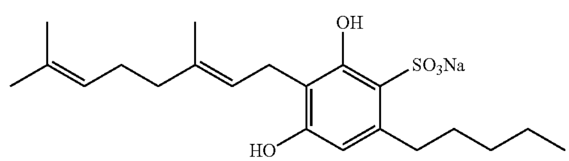 [SMILES: CCCCCc1cc(O)c(C/C=C(\C)CCC=C(C)C)c(O)c1S(=O)(=O)O] |
| 4 | 4-(cyclopropylsulfonyl)-2-(3,7-dimethylocta-2,6-dien-1-yl)-5-pentylbenzene-1,3-diol | 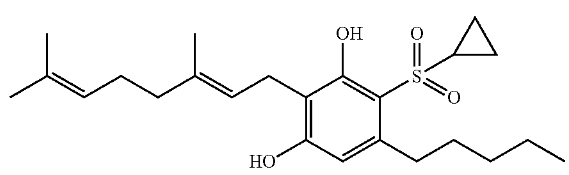 [SMILES: CCCCCc1cc(O)c(C/C=C(\C)CCC=C(C)C)c(O)c1S(=O)(=O)C1CC1] |

-continued

| Comp. No. | Name | Structure |
|---|---|---|
| 5 | 4-(tert-butylsulfonyl)-2-(3,7-dimethylocta-2,6-dien-1-yl)-5-pentylbenzene-1,3-diol | 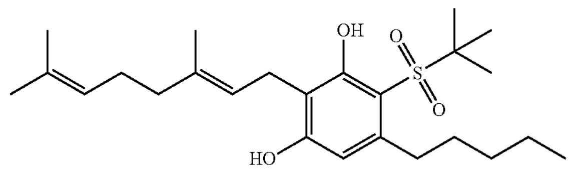 [SMILES: CCCCCc1cc(O)c(C/C=C(\C)CCC=C(C)C)c(O)c1S(=O)(=O)C(C)(C)C] |
| 6 | 4-(benzylsulfonyl)-2-(3,7-dimethylocta-2,6-dien-1-yl)-5-pentylbenzene-1,3-diol | 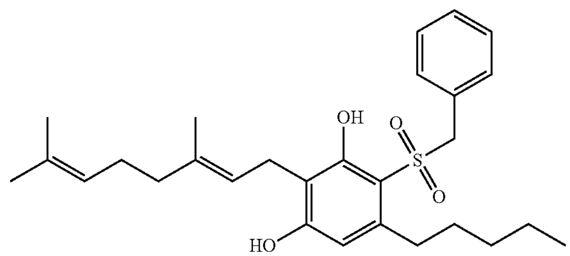 [SMILES: CCCCCc1cc(O)c(C/C=C(\C)CCC=C(C)C)c(O)c1S(=O)(=O)Cc1ccccc1] |
| 7 | 2-(3,7-dimethylocta-2,6-dien-1-yl)-5-pentyl-4-(phenylsulfonyl)benzene-1,3-diol | 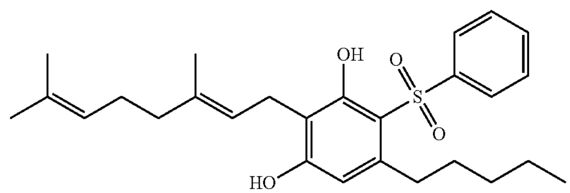 [SMILES: CCCCCc1cc(O)c(C/C=C(\C)CCC=C(C)C)c(O)c1S(=O)(=O)c1ccccc1] |
| 8 | 2-(3,7-dimethylocta-2,6-dien-1-yl)-4-((4-nitrophenyl)sulfonyl)-5-pentylbenzene-1,3-diol | 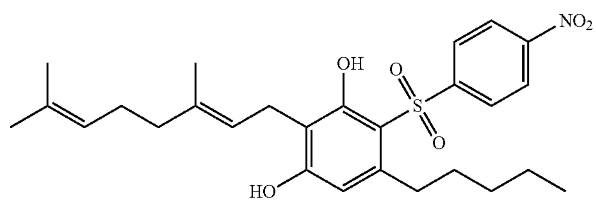 [SMILES: CCCCCc1cc(O)c(C/C=C(\C)CCC=C(C)C)c(O)c1S(=O)(=O)c1ccc([N+](=O)[O-])cc1] |
| 9 | 2-(3,7-dimethylocta-2,6-dien-1-yl)-5-pentyl-4-(pyridin-3-ylsulfonyl)benzene-1,3-diol | 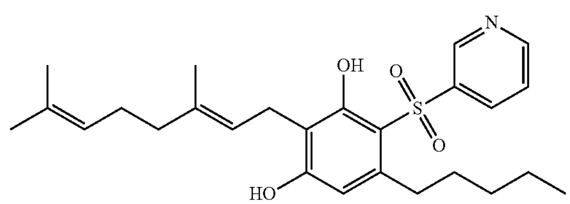 [SMILES: CCCCCc1cc(O)c(C/C=C(\C)CCC=C(C)C)c(O)c1S(=O)(=O)c1cccnc1] |
| 10 | 2-(3,7-dimethylocta-2,6-dien-1-yl)-4-(furan-3-ylsulfonyl)-5-pentylbenzene-1,3-diol | 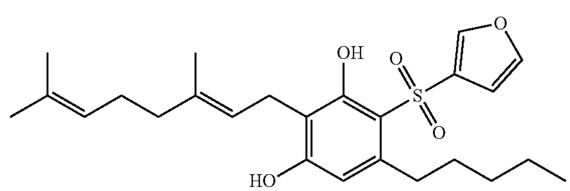 [SMILES: CCCCCc1cc(O)c(C/C=C(\C)CCC=C(C)C)c(O)c1S(=O)(=O)c1ccoc1] |
| 11 | 4-((1H-imidazol-4-yl)sulfonyl)-2-(3,7-dimethylocta-2,6-dien-1-yl)-5-pentylbenzene-1,3-diol | 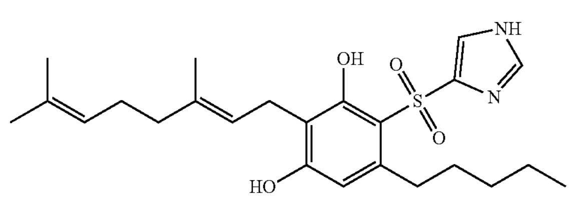 [SMILES: CCCCCc1cc(O)c(C/C=C(\C)CCC=C(C)C)c(O)c1S(=O)(=O)c1c[nH]cn1] |

-continued

| Comp. No. | Name | Structure |
|---|---|---|
| 12 | 2-(3,7-dimethylocta-2,6-dien-1-yl)-4-(oxetan-3-ylsulfonyl)-5-pentylbenzene-1,3-diol | 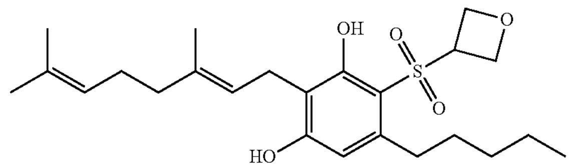 [SMILES: CCCCCc1cc(O)c(C/C=C(\C)CCC=C(C)C)c(O)c1S(=O)(=O)C1COC1] |
| 13 | 2-(3,7-dimethylocta-2,6-dien-1-yl)-5-pentyl-4-((perfluorophenyl)sulfonyl)benzene-1,3-diol | 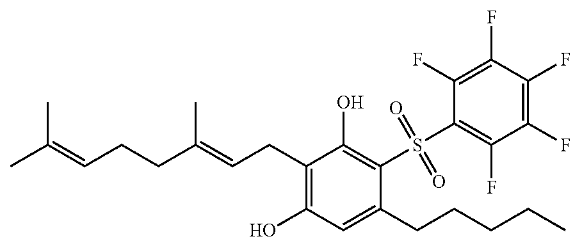 [SMILES: CCCCCc1cc(O)c(C/C=C(\C)CCC=C(C)C)c(O)c1S(=O)(=O)c1c(F)c(F)c(F)c(F)c1F] |
| 14 | 4-((3-(3,7-dimethylocta-2,6-dien-1-yl)-2,4-dihydroxy-6-pentylphenyl)sulfonyl)cyclohexan-1-one | 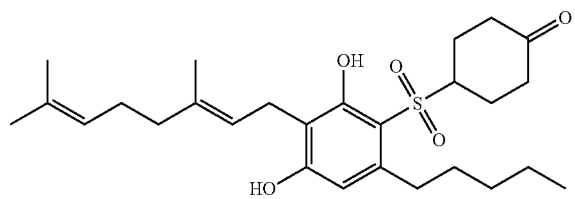 [SMILES: CCCCCc1cc(O)c(C/C=C(\C)CCC=C(C)C)c(O)c1S(=O)(=O)C1CCC(=O)CC1] |
| 15 | 1-(2-((3-(3,7-dimethylocta-2,6-dien-1-yl)-2,4-dihydroxy-6-pentylphenyl)sulfonyl)ethyl)pyrrolidine-2,5-dione | 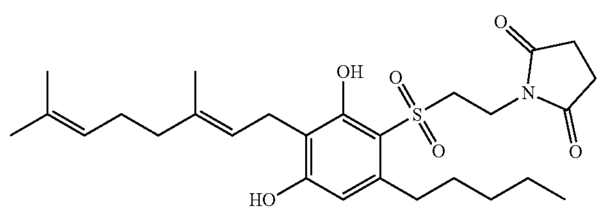 [SMILES: CCCCCc1cc(O)c(C/C=C(\C)CCC=C(C)C)c(O)c1S(=O)(=O)CCN1C(=O)CCC1=O] |
| 16 | 4-((2-(dimethylamino)ethyl)sulfonyl)-2-(3,7-dimethylocta-2,6-dien-1-yl)-5-pentylbenzene-1,3-diol | 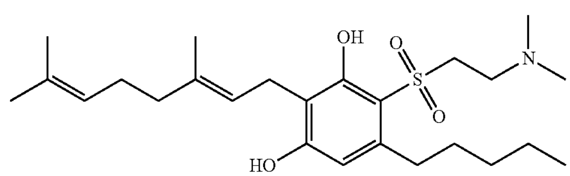 [SMILES: CCCCCc1cc(O)c(C/C=C(\C)CCC=C(C)C)c(O)c1S(=O)(=O)CCN(C)C] |
| 17 | 1-(3-((3-(3,7-dimethylocta-2,6-dien-1-yl)-2,4-dihydroxy-6-pentylphenyl)sulfonyl)piperidin-1-yl)ethan-1-one | 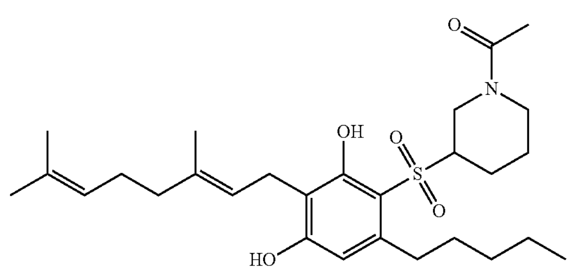 [SMILES: CCCCCc1cc(O)c(C/C=C(\C)CCC=C(C)C)c(O)c1S(=O)(=O)C1CCCN(C(C)=O)C1] |
| 18 | 4-((2-chloropyrimidin-5-yl)sulfonyl)-2-(3,7-dimethylocta-2,6-dien-1-yl)-5-pentylbenzene-1,3-diol | 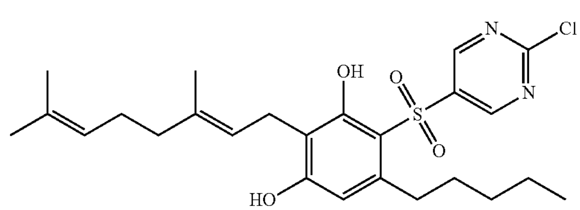 [SMILES: CCCCCc1cc(O)c(C/C=C(\C)CCC=C(C)C)c(O)c1S(=O)(=O)c1cnc(Cl)nc1] |

-continued

| Comp. No. | Name | Structure |
|---|---|---|
| 19 | 3-(3,7-dimethylocta-2,6-dien-1-yl)-2,4-dihydroxy-6-pentylbenzenesulfonamide | 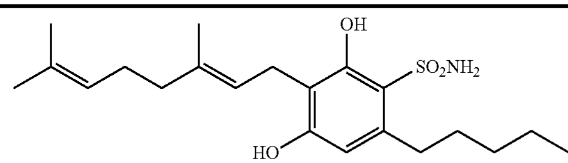 |
| 21 | 3-(3,7-dimethylocta-2,6-dien-1-yl)-2,4-dihydroxy-N,N-dimethyl-6-pentylbenzenesulfonamide | 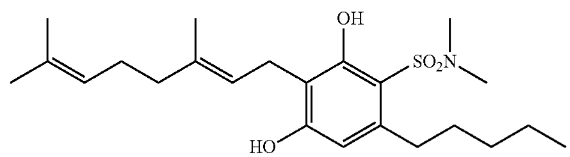 |
| 22 | N-cyclopropyl-3-(3,7-dimethylocta-2,6-dien-1-yl)-2,4-dihydroxy-6-pentylbenzenesulfonamide | 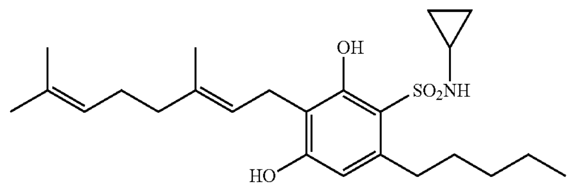 |
| 25 | N-benzyl-3-(3,7-dimethylocta-2,6-dien-1-yl)-2,4-dihydroxy-6-pentylbenzenesulfonamide | 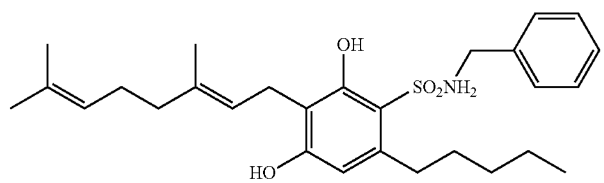 |
| 26 | 2-(3,7-dimethylocta-2,6-dien-1-yl)-4-((4-methylpiperazin-1-yl)sulfonyl)-5-pentylbenzene-1,3-diol | 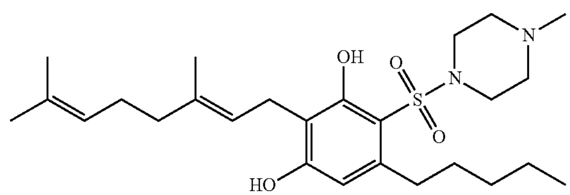 [SMILES: CCCCCc1cc(O)c(C/C=C(\C)CCC=C(C)C)c(O)c1S(=O)(=O)N1CCN(C)CC1] |
| 27 | 2-(3,7-dimethylocta-2,6-dien-1-yl)-5-pentyl-4-(piperidin-1-ylsulfonyl)benzene-1,3-diol | 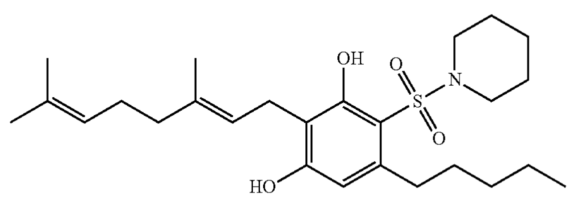 [SMILES: CCCCCc1cc(O)c(C/C=C(\C)CCC=C(C)C)c(O)c1S(=O)(=O)N1CCCCC1] |
| 29 | 3-(3,7-dimethylocta-2,6-dien-1-yl)-2,4-dihydroxy-6-pentyl-N-(pyridin-3-yl)benzenesulfonamide | 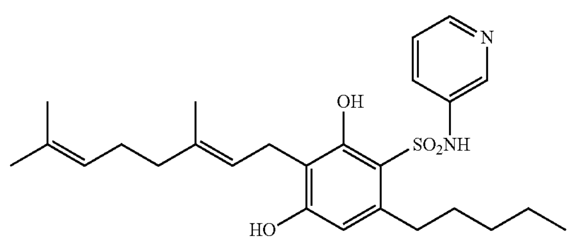 |
| 30 | 3-(3,7-dimethylocta-2,6-dien-1-yl)-2,4-dihydroxy-6-pentyl-N-(pyrimidin-2-yl)benzenesulfonamide | 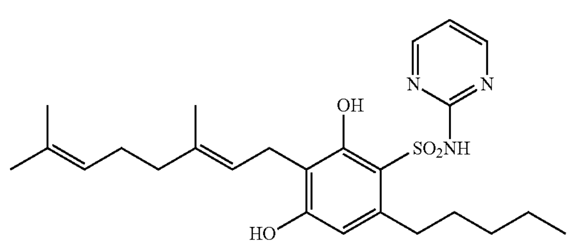 |

-continued

| Comp. No. | Name | Structure |
|---|---|---|
| 31 | 3-(3,7-dimethylocta-2,6-dien-1-yl)-2,4-dihydroxy-N-(2-oxopropyl)-6-pentylbenzenesulfonamide | 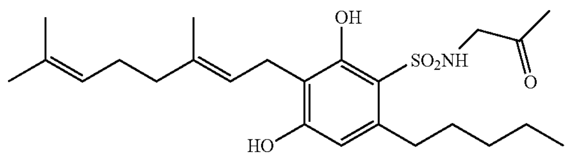 |
| 32 | 1-((3-(3,7-dimethylocta-2,6-dien-1-yl)-2,4-dihydroxy-6-pentylphenyl)sulfonyl)azetidin-3-one | 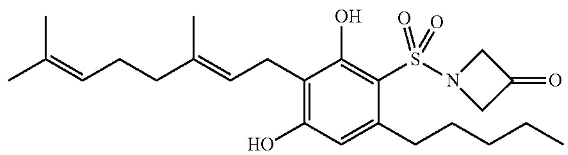 [SMILES: CCCCCc1cc(O)c(C/C=C(\C)CCC=C(C)C)c(O)c1S(=O)(=O)N1CC(=O)C1] |
| 33 | 3-(3,7-dimethylocta-2,6-dien-1-yl)-2,4-dihydroxy-N-(oxetan-2-ylmethyl)-6-pentylbenzenesulfonamide | 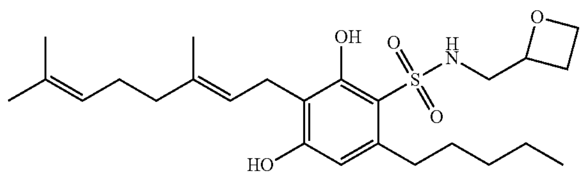 [SMILES: CCCCCc1cc(O)c(C/C=C(\C)CCC=C(C)C)c(O)c1S(=O)(=O)NCC1CCO1] |
| 34 | 4-((2-azaspiro[3.3]heptan-2-yl)sulfonyl)-2-(3,7-dimethylocta-2,6-dien-1-yl)-5-pentylbenzene-1,3-diol | 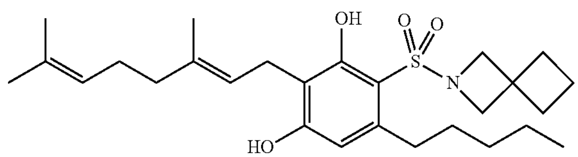 [SMILES: CCCCCc1cc(O)c(C/C=C(\C)CCC=C(C)C)c(O)c1S(=O)(=O)N1CC2(CCC2)C1] |
| 35 | 4-((2,6-diazaspiro[3.3]heptan-2-yl)sulfonyl)-2-(3,7-dimethylocta-2,6-dien-1-yl)-5-pentylbenzene-1,3-diol | 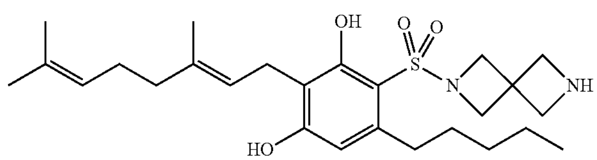 [SMILES: CCCCCc1cc(O)c(C/C=C(\C)CCC=C(C)C)c(O)c1S(=O)(=O)N1CC2(CNC2)C1] |
| 36 | ((3-(3,7-dimethylocta-2,6-dien-1-yl)-2,4-dihydroxy-6-pentylphenyl)sulfonyl)alanine | 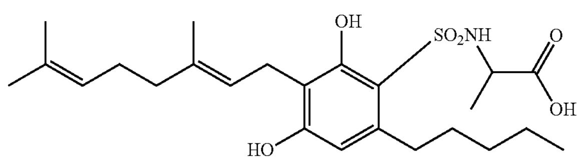 |
| 37 | methyl ((3-(3,7-dimethylocta-2,6-dien-1-yl)-2,4-dihydroxy-6-pentylphenyl)sulfonyl)alaninate | 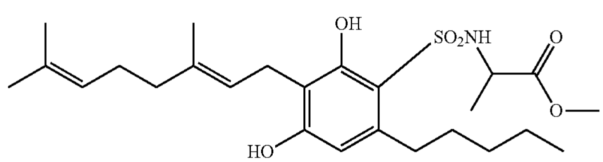 |
| 38 | N-((3-(3,7-dimethylocta-2,6-dien-1-yl)-2,4-dihydroxy-6-pentylphenyl)sulfonyl)-3-morpholinopropanamide | 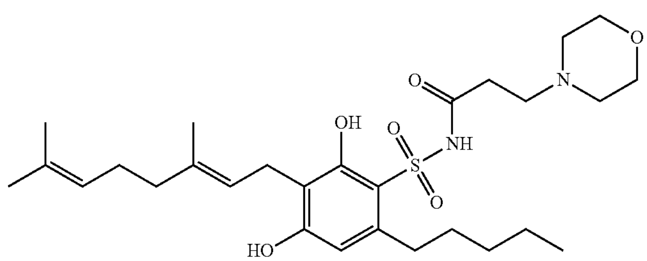 [SMILES: CCCCCc1cc(O)c(C/C=C(\C)CCC=C(C)C)c(O)c1S(=O)(=O)NC(=O)CCN1CCOCC1] |

| Comp. No. | Name | Structure |
|---|---|---|
| 39 | 4-((3-(3,7-dimethylocta-2,6-dien-1-yl)-2,4-dihydroxy-6-pentylphenyl)sulfonamido)-4-oxobutanoic acid | 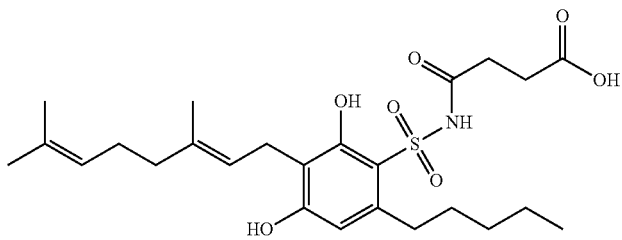 [SMILES: CCCCCc1cc(O)c(C/C=C(\C)CCC=C(C)C)c(O)c1S(=O)(=O)NC(=O)CCC(=O)O] |
| 40 | N-((3-(3,7-dimethylocta-2,6-dien-1-yl)-2,4-dihydroxy-6-pentylphenyl)sulfonyl)-3-(4-methylpiperazin-1-yl)propanamide | 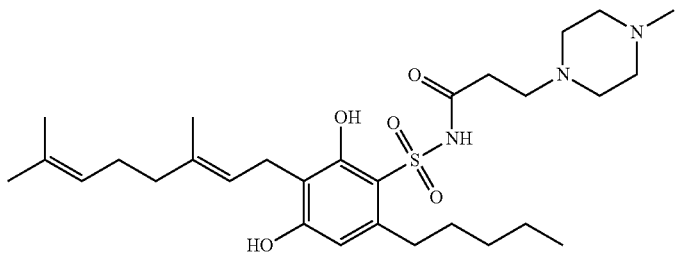 [SMILES: CCCCCc1cc(O)c(C/C=C(\C)CCC=C(C)C)c(O)c1S(=O)(=O)NC(=O)CCN1CCN(C)CC1] |
| 41 | 2-amino-N-((3-(3,7-dimethylocta-2,6-dien-1-yl)-2,4-dihydroxy-6-pentylphenyl)sulfonyl)acetamide | 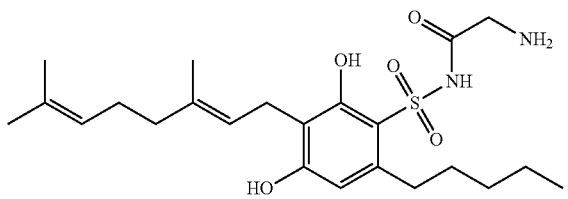 [SMILES: CCCCCc1cc(O)c(C/C=C(\C)CCC=C(C)C)c(O)c1S(=O)(=O)NC(=O)CN] |
| 42 | N-((3-(3,7-dimethylocta-2,6-dien-1-yl)-2,4-dihydroxy-6-pentylphenyl)sulfonyl)-2-(2-methoxyethoxy)acetamide | 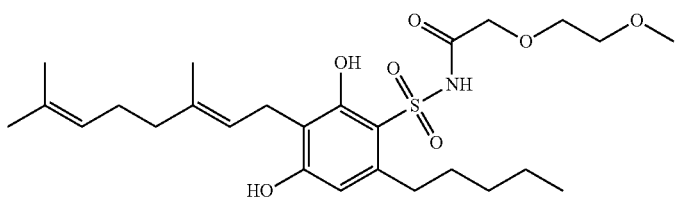 [SMILES: CCCCCc1cc(O)c(C/C=C(\C)CCC=C(C)C)c(O)c1S(=O)(=O)NC(=O)COCCOC] |
| 43 | 2-amino-N-((3-(3,7-dimethylocta-2,6-dien-1-yl)-2,4-dihydroxy-6-pentylphenyl)sulfonyl)-3-hydroxypropanamide | 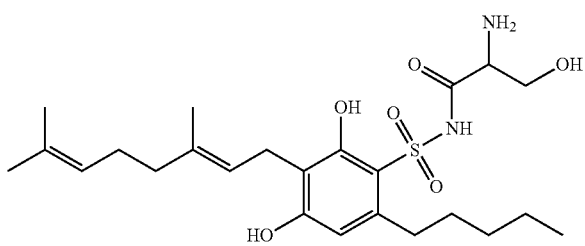 [SMILES: CCCCCc1cc(O)c(C/C=C(\C)CCC=C(C)C)c(O)c1S(=O)(=O)NC(=O)C(N)CO] |
| 44 | 2-amino-N-((3-(3,7-dimethylocta-2,6-dien-1-yl)-2,4-dihydroxy-6-pentylphenyl)sulfonyl)propanamide | 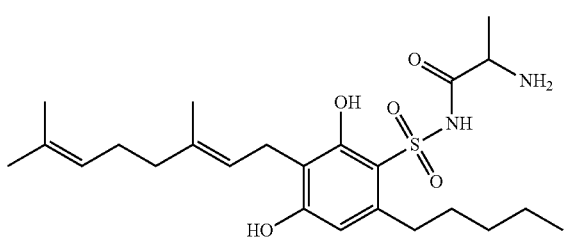 [SMILES: CCCCCc1cc(O)c(C/C=C(\C)CCC=C(C)C)c(O)c1S(=O)(=O)NC(=O)C(C)N] |

| Comp. No. | Name | Structure |
|---|---|---|
| 45 | 3-amino-N-((3-(3,7-dimethylocta-2,6-dien-1-yl)-2,4-dihydroxy-6-pentylphenyl)sulfonyl)-2-methylpropanamide | 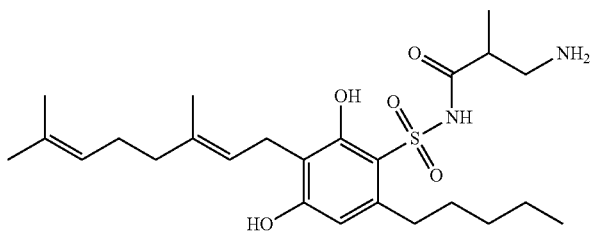 [SMILES: CCCCCc1cc(O)c(C/C=C(\C)CCC=C(C)C)c(O)c1S(=O)(=O)NC(=O)C(C)CN] |
| 46 | N-((3-(3,7-dimethylocta-2,6-dien-1-yl)-2,4-dihydroxy-6-pentylphenyl)sulfonyl)acetamide | 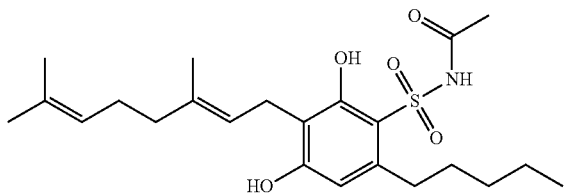 [SMILES: CCCCCc1cc(O)c(C/C=C(\C)CCC=C(C)C)c(O)c1S(=O)(=O)NC(C)=O] |
| 47 | N-((3-(3,7-dimethylocta-2,6-dien-1-yl)-2,4-dihydroxy-6-pentylphenyl)sulfonyl)-3-oxobutanamide | 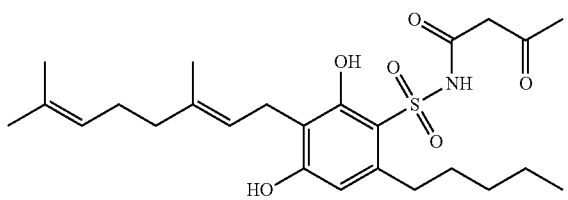 [SMILES: CCCCCc1cc(O)c(C/C=C(\C)CCC=C(C)C)c(O)c1S(=O)(=O)NC(=O)CC(C)=O] |
| 48 | N-((3-(3,7-dimethylocta-2,6-dien-1-yl)-2,4-dihydroxy-6-pentylphenyl)sulfonyl)-2-(3-methyl-1H-1,2,4-triazol-5-yl)acetamide | 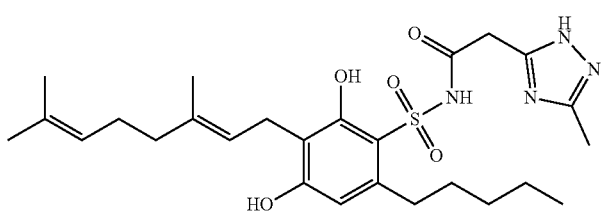 [SMILES: CCCCCc1cc(O)c(C/C=C(\C)CCC=C(C)C)c(O)c1S(=O)(=O)NC(=O)Cc1nc(C)n[nH]1] |
| 49 | N-((3-(3,7-dimethylocta-2,6-dien-1-yl)-2,4-dihydroxy-6-pentylphenyl)sulfonyl)-1H-1,2,4-triazole-5-carboxamide | 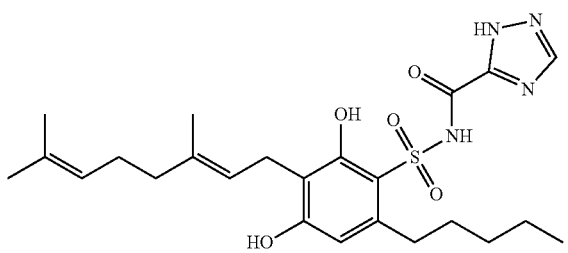 [SMILES: CCCCCc1cc(O)c(C/C=C(\C)CCC=C(C)C)c(O)c1S(=O)(=O)NC(=O)c1ncn[nH]1] |
| 50 | N-((3-(3,7-dimethylocta-2,6-dien-1-yl)-2,4-dihydroxy-6-pentylphenyl)sulfonyl)oxetane-2-carboxamide | 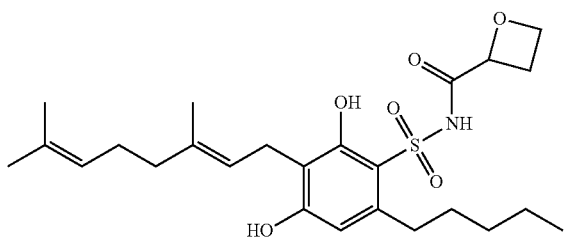 [SMILES: CCCCCc1cc(O)c(C/C=C(\C)CCC=C(C)C)c(O)c1S(=O)(=O)NC(=O)C1CCO1] |

-continued

| Comp. No. | Name |
|---|---|
| 51 | N-((3-(3,7-dimethylocta-2,6-dien-1-yl)-2,4-dihydroxy-6-pentylphenyl)sulfonyl)benzamide |
| 52 | N-((3-(3,7-dimethylocta-2,6-dien-1-yl)-2,4-dihydroxy-6-pentylphenyl)sulfonyl)nicotinamide |
| 53 | N-((3-(3,7-dimethylocta-2,6-dien-1-yl)-2,4-dihydroxy-6-pentylphenyl)sulfonyl)-2-phenylacetamide |
| 54 | N-((3-(3,7-dimethylocta-2,6-dien-1-yl)-2,4-dihydroxy-6-pentylphenyl)sulfonyl)-2-(furan-2-yl)acetamide |
| 55 | N-((3-(3,7-dimethylocta-2,6-dien-1-yl)-2,4-dihydroxy-6-pentylphenyl)sulfonyl)-2-(oxazol-2-yl)acetamide |
| 56 | N-((3-(3,7-dimethylocta-2,6-dien-1-yl)-2,4-dihydroxy-6-pentylphenyl)sulfonyl)-2-(thiazol-2-yl)acetamide |
| 57 | 2-(1H-benzo[d]imidazol-2-yl)-N-((3-(3,7-dimethylocta-2,6-dien-1-yl)-2,4-dihydroxy-6-pentylphenyl)sulfonyl)acetamide |

| Comp. No. | Name | Structure |
|---|---|---|
| 59 | N-(cyclohexylsulfonyl)-3-(3,7-dimethylocta-2,6-dien-1-yl)-2,4-dihydroxy-6-pentylbenzamide | 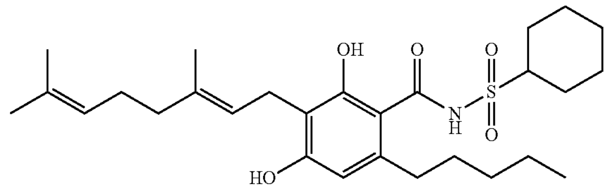 [SMILES: CCCCCc1cc(O)c(C/C=C(\C)CCC=C(C)C)c(O)c1C(=O)NS(=O)(=O)C1CCCCC1] |
| 60 | 3-(3,7-dimethylocta-2,6-dien-1-yl)-2,4-dihydroxy-6-pentyl-N-((prop-1-en-1-yl)sulfonyl)benzamide | 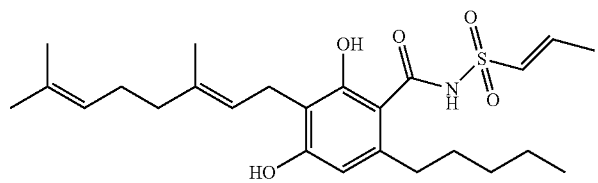 [SMILES: C/C=C/S(=O)(=O)NC(=O)c1c(CCCCC)cc(O)c(C/C=C(\C)CCC=C(C)C)c1O] |
| 61 | N-((1H-benzo[d]imidazol-2-yl)sulfonyl)-3-(3,7-dimethylocta-2,6-dien-1-yl)-2,4-dihydroxy-6-pentylbenzamide | 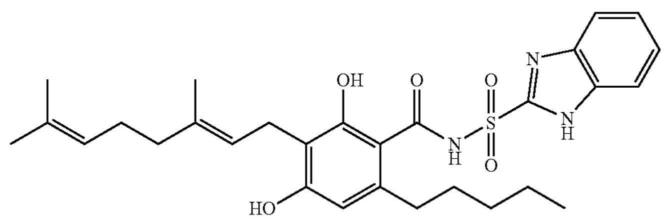 [SMILES: CCCCCc1cc(O)c(C/C=C(\C)CCC=C(C)C)c(O)c1C(=O)NS(=O)(=O)c1nc2ccccc2[nH]1] |

The disclosure also provides analogs of compounds disclosed herein, including for example analogs of compounds 19, 20, 22-25, 29-31, 33, and 36-66 in which the amino moiety in sulfonamide is methylated. For example, such an analog of compound 61 is N-((1 H-benzo[d]imidazol-2-yl)sulfonyl)-3-(3,7-dimethylocta-2,6-dien-1-yl)-2,4-dihydroxy-N-methyl-6-pentylbenzamide; such analogs of all other compounds of the Table are specifically contemplated where chemically reasonable.

Radioligand Competitive Binding Assays—CB1 and CB2

Example 14

Compounds of the present disclosure were tested for CB1 receptor binding affinity and for CB2 receptor binding affinity. As used herein, "binding affinity" is represented by the $IC_{50}$ value, which was experimentally determined as described herein. The lower the $IC_{50}$ value the higher the binding affinity. A compound of the present disclosure may be said to have "binding selectivity" if it has a higher binding affinity for one receptor compared to the other. For example, a compound that has an $IC_{50}$ of 1 µM for CB1 and 0.1 µM for CB2 is 10 times more selective for the CB2 receptor.

CB1 Membrane Preparation

The membranes were prepared from CHO-K1 (Chinese hamster ovary) cells stably transfected with the human CB1 receptor (Cat. #ES-110-C; Perkin Elmer, Boston, MA). The cells were grown adherently and maintained in Ham's F12 medium containing 10% fetal bovine serum (FBS), penicillin, streptomycin and geneticin (G418) at 37° C. in a humid atmosphere of 5% $CO_2$ following the manufacturer's instructions.

For membrane preparation the cells were washed with PBS and scraped off the plates in cold homogenization buffer (25 mM HEPES (pH 7.4), 2 mM EDTA) containing protease inhibitor cocktail (Sigma Cat. #P8340). The cell suspension was homogenized with a Pro-PK-01200D Polytron Homogenizer (Pro Scientific) and then centrifuged for 30 min at 120,000×g. The supernatant was discarded and the pellet was re-suspended in the homogenization buffer and stored at −80° C. until the time of use.

CB1 Radioligand Binding Assay

CP 55,940 is a synthetic cannabinoid that mimics the effects of naturally occurring THC. It acts as a full agonist at both cannabinoid CB1 and CB2 receptors. Radiolabeled ligands represent one of the most sensitive methods for probing receptor binding biology. In this experiment, 3H radiolabeled CP 55,940, i.e. [3H]CP 55,940 (Perkin Elmer, Boston, MA), was used as a radioligand for the CB1 receptor.

[3H]CP 55,940 displacement assays were used for the determination of the binding affinity of compounds for the CB1 receptor (Scheme 7; below).

Scheme 7: Schematic representation of the radioligand binding assay for CB1 and CB2

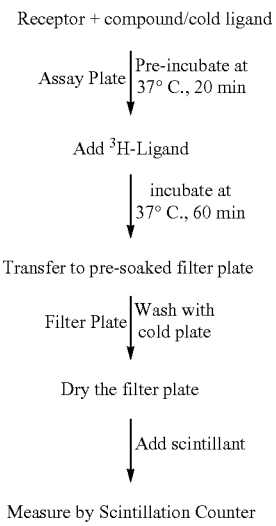

The competition binding experiments (single dose and dose-response) were performed by incubating 0.8 nM of [3H]CP 55,940 (specific activity 101 Ci/mmol, Perkin Elmer) and different concentrations of compounds disclosed herein with membranes prepared as above from CHO-K1 cells expressing human CB1 receptor (6 μg of protein/well), 50 mM Tris-HCl (pH 7.4), 5 mM MgCl$_2$, 1 mM CaCl$_2$, and 2 mg/mL BSA.

For the single dose experiments, the compound stocks (usually 10 mM in DMSO) were diluted to working stocks in the binding buffer to give the final compound concentrations of 10 μM and 1 μM. For the dose-response experiments, the test compounds were sequentially diluted to provide the desired concentration range for the IC$_{50}$ determination. In each case the compounds were pre-incubated with the membrane for 20 min, before adding the radioligand.

After incubation with the radioligand for 60 min at 37° C., the incubation was terminated by rapid filtration of the assay mixture through MultiScreen®$_{HTS}$+96-well filter plates (Millipore, Cat. #MSFCNXB), pre-soaked for 60 min with 50 mM Tris-HCl (pH 7.4) containing 0.33% polyethylenimine (PEI). The nonspecific binding (NSB) was determined in the presence of 10 μM unlabelled CP 55,940. After drying the filter plate at 50° C. for at least 60 min, the filter-bound radioactivity was determined by scintillation spectrometry using the 1450 MicroBeta Plate Counter (Perkin Elmer, Boston, MA). From the dose-response experiments, the IC$_{50}$ values were determined (see Table 1, CB1 IC$_{50}$).

In Table 1 below, the fold difference in selectivity between CB1 and CB2 binding is indicated, with the fold difference presented in the column of the receptor that exhibited the higher binding affinity (i.e. CB1 or CB2). Where the test compound had about the same affinity for both receptors, this is represented by a value of 1.00 in the column for both receptors. None of the compounds listed in Table 1 were found to exhibit selectivity for the CB1 receptor.

CB2 Membrane Preparation

The membranes were prepared from CHO-K1 (Chinese hamster ovary) cells stably transfected with the human CB2 receptor (Cat. #ES-111-C; Perkin Elmer, Boston, MA). The cells were grown adherently and maintained in Ham's F12 medium containing 10% fetal bovine serum (FBS), penicillin, streptomycin and geneticin (G418) at 37° C. in a humid atmosphere of 5% CO$_2$ following the manufacturer's instructions.

For membrane preparation the cells were washed with PBS and scraped off the plates in cold homogenization buffer (25 mM HEPES (pH 7.4), 2 mM EDTA) containing protease inhibitor cocktail (Sigma Cat. #P8340). The cell suspension was homogenized with a Pro-PK-01200D Polytron Homogenizer (Pro Scientific) and then centrifuged for 30 min at 120,000×g. The supernatant was discarded and the pellet was re-suspended in the homogenization buffer and stored at −80° C. until the time of use.

CB2 Radioligand Binding Assay

In this experiment, 3H radiolabeled CP 55,940, i.e. [3H]CP 55,940 (Perkin Elmer, Boston, MA), was used as a radioligand for the CB2 receptor to determine the binding affinity of compounds for the CB2 receptor (Scheme 7; above).

The competition binding experiments (single dose and dose-response) were performed by incubating 0.6 nM of [3H]CP55,940 (specific activity 101 Ci/mmol, Perkin Elmer) and different concentrations of compounds disclosed herein with membranes prepared as above from CHO-K1 cells expressing human CB2 receptor (1 μg of protein/well), 50 mM Tris-HCl (pH 7.4), 5 mM MgCl$_2$, 1 mM CaCl$_2$, and 2 mg/mL BSA.

For the single dose experiments, the compound stocks (usually 10 mM in DMSO) were diluted to working stocks in the binding buffer to give the final compound concentrations of 10 μM and 1 μM. For the dose-response experiments the test compounds were sequentially diluted to provide the desired concentration range for the IC50 determination. In each case the compounds were pre-incubated with the membrane for 20 min, before adding the radioligand.

After incubation with the radioligand for 60 min at 37° C., the incubation was terminated by rapid filtration of assay mixture through MultiScreen®$_{HTS}$+ 96-well filter plates (Millipore, Cat. #MSFCNXB), pre-soaked for 60 min with 50 mM Tris-HCl (pH 7.4) containing 0.33% polyethylenimine (PEI). The nonspecific binding (NSB) was determined in the presence of 10 μM unlabelled CP55,940. After drying the filter plate at 50° C. for at least 60 min, the filter-bound radioactivity was determined by scintillation spectrometry using the 1450 MicroBeta Plate Counter (Perkin Elmer, Boston, MA). From the dose-response experiments, the IC$_{50}$ values were determined (see Table 1, CB2 IC$_{50}$).

Compounds of the present disclosure listed in Table 1 exhibited selectivity for the CB2 receptor over the CB1 receptor. Again, in Table 1 below, the fold difference in selectivity between CB1 and CB2 binding is indicated, with the fold difference presented in the column of the receptor that exhibited the higher binding affinity (i.e. CB1 or CB2). Where the test compound had about the same affinity for both receptors, this is represented by a value of 1.00 in the column for both receptors.

TABLE 1

Data from Radioligand Competitive Binding Assays

| Compound | CB1 IC$_{50}$ | CB2 IC$_{50}$ | Selectivity CB1 | CB2 |
|---|---|---|---|---|
| 20 | D | B | | 3.93 |
| 23 | D | B | | 18.43 |
| 24 | B | A | | 61.50 |
| 62 | D | B | | 9.04 |
| 58 | D | D | | 1.88 |
| 65 | D | A | | 25.50 |
| 64 | D | B | | 7.89 |
| 63 | D | A | | 24.80 |
| 66 | D | D | | 1.88 |
| 67 | D | B | | 20.83 |
| 28 | C | A | | 266.67 |
| 3 | D | C | | 1.47 |

A = <0.10 µM
B = 0.10 µM to 0.49 µM
C = 0.50 µM to 0.99 µM
D = ≥1.00 µM

GTPγS Functional Assay

Example 15

Membrane Preparation

The membranes were prepared from CHO-K1 cells stably transfected with the human CB1 receptor (Perkin Elmer, Boston, MA). The cells were grown adherently and maintained in Ham's F12 medium containing 10% fetal bovine serum (FBS), penicillin, streptomycin and geneticin (G418) at 37° C. in a humid atmosphere of 5% $CO_2$ following the manufacturer's instructions.

For membrane preparation the cells were washed with PBS and scraped off the plates in cold homogenization buffer (25 mM HEPES (pH 7.4), 2 mM EDTA) containing protease inhibitor cocktail (Sigma Cat. #P8340). The cell suspension was homogenized with a Polytron and then centrifuged for 30 min at 120,000×g.

GTPγS Assay

GTPγS binding assay was used for direct measurement of the binding of a non-hydrolysable GTP analog [35S]-GTPγS to the cell membranes containing overexpressed CB1 or CB2 receptors. Upon receptor activation by an agonist, the G protein is stimulated to bind the non-hydrolysable [35S] GTPγS, allowing [35S]GTPγS-labeled Ga-subunits to accumulate following receptor activation. The bound [35S] GTPγS can be separated from unbound [35S]GTPγS using filtration and quantified by scintillation counting.

The assays were performed by incubating 5 µg of either CB1 or CB2 membrane in a total volume of 100 µl in assay buffer (50 mM Tris-HCl, 5 mM $MgCl_2$, 150 mM NaCl, 1 mM EDTA, 0.05% BSA and 1 mM DTT, pH 7.4) supplemented with 3 µM GDP and 0.05 mg/ml saponin. In each case, the reaction for maximal (stimulated) level of binding contained 0.3 nM [$^{35}$S]GTPγS and 10 µM CP55,940. Agonist mode was determined, with increasing concentrations of test compounds in the absence of agonist (CP55,940). Antagonist mode for both CB1 and CB2 contained an EC$_{60}$ concentration of (−)—CP55,940 (12 nM). The basal level of [35S]GTPγS binding was measured in untreated membranes containing no CP55,940 and non-specific binding (NSB) was determined with 10 µM GTPγS.

The tested compounds were incubated with membrane/GDP mixture for 30 minutes at room temperature before adding 0.3 nM [$^{35}$]GTPγS. The final reaction mixture was incubated at 30° C. for 45 minutes. Incubations were terminated by rapid vacuum filtration to separate the bound and free radioligand with Multi Screen 96-well filter plate on a MultiScreen$_{HTS}$ vacuum manifold. Filters were subsequently washed 5 times with ice-cold wash buffer containing 50 mM Tris-HCl, pH 7.4 and 5 mM $MgCl_2$. After drying, scintillant was added to each filter. After 1 hour, the filter-bound radioactivity was determined by scintillation spectrometry using a 1450 Microbeta scintillation counter (Perkin Elmer).

Compounds of the present disclosure were tested in agonist and antagonist mode for both the CB1 and CB2 receptors. The tested compounds were generally found to exhibit activity in antagonist mode at the CB1 and CB2 receptor.

Further Biological Examples

Example 16: Simulated Gastric Fluid (SGF) Assay

In a microcentrifuge tube, 626.5 µL of a solution containing 1.1× assay buffer (37.6 mM NaCl, pH 1.2-1.5) is diluted with 70 µL of a 10× pepsin solution (Sigma-Aldrich Co. Cat #: P7012, 80,000 U/mL in milliQ water). The resulting solution is incubated at 37° C. and 1,200 rpm in an orbital mixer for 5 minutes, prior to the addition of 3.5 µL of the test compound (2 mM, DMSO). The sample is incubated in the same conditions for as long as required.

At the specified time points, 150 µL aliquots of the sample are transferred to microcentrifuge tubes containing 24 µL of acid quenching solution (0.5 M $NaHCO_3$). After vortexing the tube for 5 seconds, 348 µL of the protein precipitation solution containing an internal standard (25 µM Glyburide, ACN) are added. The tube is vortexed again for seconds, and stored in ice.

Finally, the tubes are centrifuged at 5,000×g and 4° C. for 15 minutes. The percentage remaining of the test compound, compared to time zero, is quantified in the supernatant by HPLC/LC-MS or LC-MS/MS and the half-life is determined.

Example 17: TRPs Activation: Measurement of Cation Flux Through Intracellular Calcium Detection The transient receptor potential ion channels (TRPs) are non-selective ligand-gated cation channels that integrate a variety of physical and chemical stimuli. When activated, these channels lead to the gating of cations, including $Ca^{2+}$, thus generating changes in intracellular calcium concentration. The single wavelength fluorescent indicator Fluo-4 acetoxymethyl (AM) is used to measure intracellular calcium flux and concentration in cells expressing TRPs and stimulated with cannabinoids. The Fluo-4 Direct™ calcium assay kit (Molecular Probes, Invitrogen, Carlsbad, CA, USA) allows the direct addition of the reagent into microplate wells containing cultured cells, without the requirement of media removal or a wash step, therefore facilitating the process of target screening.

As adapted from Moriello et al. ("Assay of TRPV1 Receptor Signaling" *Methods In Molecular Biology* (2016) 1412:65-76, herein incorporated by reference), human embryonic kidney (HEK-293) cells are used to express different TRPs, including TRPV1 and TRPV2. Cells are grown in Eagle's Minimum Essential Medium supplemented with 10% fetal bovine serum (FBS), 1% penicillin and streptomycin(pen/strep), and maintained in incubators at 37° C. in 5% $CO_2$. Cells are seeded in 96-well plates and polyethylenimine (PEI) used to transiently transfect HEK-293 cells with expression vectors containing the open reading frame (ORF) of the TRPs of interest. Transfection using the empty expression vector is performed as a negative control.

24-48 hours after transfection, cells are treated with Fluo-4 Direct™ (Molecular Probes) for 30-60 minutes and subsequently exposed to cannabinoids and benchmark compounds for different periods of time. Following incubations, fluorescence is measured using a microplate reader (excitation at 494 nm and emission at 516 nm).

Analysis of data is done by generating nonlinear regression curves and all data points corrected for background fluorescence and negative control. The response of agonists is normalized to the effect of a reference agonist and the response of antagonists normalized to the $EC_{80}$ of a reference agonist.

Example 18: PPARγ Activation: Nuclear Hormone Receptor Activation Assay

Peroxisome proliferator activated receptors (PPARs) are ligand-activated transcription factors of nuclear hormone receptors (NHRs). The PathHunter® PPARγ protein interaction assay (DiscoverX, Fremont, CA, USA) reports the activation of NHRs based on enzyme complementation of β-galactosidase, rendering a chemiluminescent signal.

CHO-K1 PPARγ cell lines (DiscoverX) stably expressing the target receptor is used. Cells are grown using reagents provided by the manufacturer (DiscoverX) and maintained in incubators at 37° C. in 5% $CO_2$. Cells are harvested and plated in black skirt, clear bottom 96-well plates and allowed to attach and recover overnight. Subsequently, cells are incubated with cannabinoids and/or benchmark compounds, such as troglitazone and rosiglitazone, for 30-90 minutes at 37° C. in 5% $CO_2$. The detection reagent provided by the manufacturer (DiscoverX) is then added to the wells, and plates are incubated for 1 hour in the dark, followed by chemiluminescence detection using a microplate reader. Analysis of data is done by generating nonlinear regression curves and all data points are corrected for background luminescence and negative control. The response of agonists is normalized to the effect of a reference agonist and the response of antagonists normalized to the $EC_{80}$ of a reference agonist. Basal activity of the cells is set at 0%.

Numerous references have been made to patents and printed publications throughout this specification. Each of the cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:
1. A compound having structural formula:

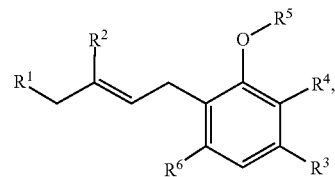

or an enantiomer, diastereomer, racemate, or tautomer thereof, or a pharmaceutically acceptable salt, solvate or hydrate of the compound, enantiomer, diastereomer, racemate, or tautomer, wherein $R^1$ is hydrogen, halo, $C_1$-$C_8$ alkyl, $C_2$-$C_8$ alkenyl, $C_2$-$C_8$ alkynyl, —$CO_2H$, —($C_0$-$C_4$ alkyl)-C(O)O($C_1$-$C_6$ alkyl), —($C_0$-$C_4$ alkyl)-OC(O)O—($C_1$-$C_6$ alkyl), —($C_0$-$C_4$ alkyl)-N($R^{1b}$)—C(O)—O—($C_1$-$C_6$ alkyl), —($C_0$-$C_4$ alkyl)-O—C(O)—$NR^{1b}R^{1c}$, —($C_0$-$C_4$ alkyl)-N(Rib)-C(O)—$NR^{1b}R^{1c}$, —$OR^{1a}$, —($C_1$-$C_4$ alkyl)$OR^{1a}$, —$SR^{1a}$, —($C_1$-$C_4$ alkyl)$S(O)_{0-2}R^{1a}$, —$NR^{1b}R^{1c}$, —($C_1$-$C_4$ alkyl)$NR^{1b}R^{1c}$, —($C_1$-$C_4$ alkyl) $C(O)NR^{1b}R^{1c}$, —($C_0$-$C_4$ alkyl)-aryl, —($C_0$-$C_4$ alkyl)-heteroaryl, —($C_0$-$C_4$ alkyl)-cycloalkyl, or —($C_0$-$C_4$ alkyl)-heterocycloalkyl, wherein $R^{1a}$, $R^{1b}$, and $R^{1c}$ are independently hydrogen, $C_1$-$C_4$ alkyl, or —C(O)($C_1$-$C_4$) alkyl;

$R^2$ is hydrogen, halo, $C_1$-$C_8$ alkyl, $C_2$-$C_8$ alkenyl, $C_2$-$C_8$ alkynyl, —$CO_2H$, —($C_0$-$C_4$ alkyl)-C(O)O($C_1$-$C_6$ alkyl), —($C_0$-$C_4$ alkyl)-OC(O)O—($C_1$-$C_6$ alkyl), —($C_1$-$C_4$ alkyl)$OR^{2a}$, —($C_1$-$C_4$ alkyl)$SR^{2a}$, —$NR^{2b}R^2c$ —($C_1$-$C_4$ alkyl)$NR^{2b}R^2c$, —($C_1$-$C_4$ alkyl) $C(O)NR^{2b}R^2c$, —($C_0$-$C_4$ alkyl)-aryl, —($C_0$-$C_4$ alkyl)-heteroaryl, —($C_0$-$C_4$ alkyl)-cycloalkyl, or —($C_0$-$C_4$ alkyl)-heterocycloalkyl, wherein $R^{2a}$, $R^{2b}$, and $R^{2c}$ are independently hydrogen, $C_1$-$C_4$ alkyl, or —C(O)($C_1$-$C_4$) alkyl;

$R^3$ is hydrogen, $C_1$-$C_{12}$ alkyl, $C_2$-$C_{12}$ alkenyl, $C_2$-$C_{12}$ alkynyl, —$(OCH_2CH_2)_{0-6}O(C_1$-$C_8$ alkyl), —($C_0$-$C_4$ alkyl)-$NR^{3a}R^{3b}$, —($C_0$-$C_4$ alkyl)-aryl, —($C_0$-$C_4$ alkyl)-heteroaryl, —($C_0$-$C_4$ alkyl)-cycloalkyl or —($C_0$-$C_4$ alkyl)-heterocycloalkyl, wherein $R^3a$ and $R^{3b}$ are each independently hydrogen or $C_1$-$C_6$ alkyl;

$R^4$ is

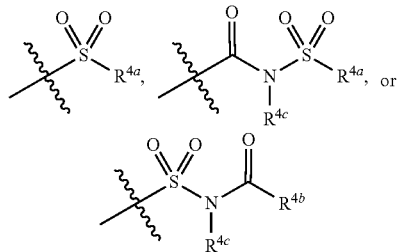

wherein
$R^{4a}$ is $C_1$-$C_8$ alkyl, $C_2$-$C_8$ alkenyl, $C_2$-$C_8$ alkynyl, —$OR^{4a}$, —($C_1$-$C_4$ alkyl)$OR^{4e}$, —($C_1$-$C_4$ alkyl)-C(O)($C_1$-$C_4$ alkyl), —($C_0$-$C_4$ alkyl)-aryl, —($C_0$-$C_4$ alkyl)-heteroaryl, —($C_0$-$C_4$ alkyl)-cycloalkyl, —($C_0$-$C_4$ alkyl)-heterocycloalkyl, —$NR^{4d}R^{4e}$, or —($C_1$-$C_4$ alkyl) $NR^{4d}R^{4e}$, and $R^{4b}$ is $C_1$-$C_8$ alkyl, $C_2$-$C_8$ alkenyl, $C_2$-$C_8$ alkynyl, —$CH_2$—$(OCH_2CH_2)_{0-6}O(C_1$-$C_8$ alkyl), —$(C_1$-$C_4$ alkyl)$OR^{4e}$, —$(C_1$-$C_4$ alkyl)-C(O)($C_1$-$C_4$ alkyl), —$(C_1$-$C_4$ alkyl)-C(O)O($R^{4e}$), —$(C_0$-$C_4$ alkyl)-aryl, —$(C_0$-$C_4$ alkyl)-heteroaryl, —$(C_0$-$C_4$ alkyl)-cycloalkyl, —$(C_0$-$C_4$ alkyl)-heterocycloalkyl, or —$(C_1$-$C_4$ alkyl)$NR^{4d}R^{4e}$, wherein $R^{4d}$ is hydrogen, $C_1$-$C_6$ alkyl, $C_2$-$C_6$ alkenyl, —$(C_1$-$C_4$ alkyl)-C(O)($C_1$-$C_4$ alkyl), —$(C_1$-$C_4$ alkyl)-C(O)O ($R^{4e}$), —$(C_1$-$C_4$ alkyl)-OC(O)($R^{4e}$), —$(C_0$-$C_4$ alkyl)-aryl, —$(C_0$-$C_4$ alkyl)-heteroaryl, —$(C_0$-$C_4$ alkyl)-cycloalkyl, or —$(C_0$-$C_4$ alkyl)-heterocycloalkyl, $R^{4e}$ is hydrogen, $C_1$-$C_4$ alkyl, or aryl, and $R^{4c}$ is hydrogen or $C_1$-$C_4$ alkyl;

$R^5$ is hydrogen, $C_1$-$C_8$ alkyl, —$(C_1$-$C_4$ alkyl)-O—$(C_1$-$C_4$ alkyl), —C(O)($C_1$-$C_4$ alkyl), —C(O)O($C_1$-$C_4$ alkyl), —C(O)$NH_2$, —C(O)NH($C_1$-$C_4$ alkyl), —C(O)N($C_1$-$C_4$ alkyl)$_2$, —$(C_1$-$C_4$ alkyl)C(O)O($C_1$-$C_4$ alkyl), or —$(C_1$-$C_4$ alkyl)OC(O)($C_1$-$C_4$ alkyl); and $R^6$ is hydrogen or —$OR^{6a}$, wherein $R^{6a}$ is hydrogen, $C_1$-$C_8$ alkyl, —$(C_1$-$C_4$ alkyl)-O—$(C_1$-$C_4$ alkyl), —C(O)($C_1$-$C_4$ alkyl), —C(O)O($C_1$-$C_4$ alkyl), —C(O)$NH_2$, —C(O)NH($C_1$-$C_4$ alkyl), —C(O)N($C_1$-$C_4$ alkyl)$_2$, —$(C_1$-$C_4$ alkyl)C(O)O($C_1$-$C_4$ alkyl), or —$(C_1$-$C_4$ alkyl)OC(O)($C_1$-$C_4$ alkyl);

wherein
each alkyl, alkenyl and alkynyl is unsubstituted, halogenated, substituted with one or two hydroxyl or $C_1$-$C_6$ alkoxy groups, or substituted with one or two oxo groups;

each cycloalkyl has 3-10 ring carbons and is saturated or partially unsaturated, and optionally includes one or two fused cycloalkyl rings, each fused cycloalkyl ring having 3-8 ring members, and is substituted with 0-6 $R^7$;

each heterocycloalkyl has 3-10 ring members and 1-3 heteroatoms where each heteroatom is independently nitrogen, oxygen or sulfur and is saturated or partially unsaturated, and optionally includes one or two fused cycloalkyl rings, each fused cycloalkyl ring having 3-8 ring members, and is substituted with 0-6 $R^7$;

each aryl is a phenyl or a naphthyl, and optionally includes one or two fused cycloalkyl or heterocycloalkyl rings, each fused cycloalkyl or heterocycloalkyl ring having 4-8 ring members, and is substituted with 0-5 $R^8$;

each heteroaryl is a 5-6 membered monocyclic heteroaryl ring having 1-4 heteroatoms, where each heteroatom is independently nitrogen, oxygen or sulfur or a 8-10 membered bicyclic heteroaryl having 1-5 heteroatoms where each heteroatom is independently nitrogen, oxygen or sulfur, and optionally includes one or two fused cycloalkyl or heterocycloalkyl rings, each fused cycloalkyl or heterocycloalkyl ring having 4-8 ring members, and is substituted with 0-5 $R^8$, in which
each $R^7$ is independently oxo, $C_1$-$C_4$ alkyl, —$C_1$, —F, —Br, —CN, —$SF_5$, —$N_3$, nitro, —$SR^A$, —$S(O)_{1-2}R^A$, —$OR^A$, —$(C_0$-$C_3$ alkyl)-$OR^B$, —$NR^BR^A$, —$C(O)R^A$, —$C(O)NR^BR^A$, —$NR^BC(O)R^A$, —$C(S)NR^BR^A$, —$NR^BC(S)R^A$, —$CO_2R^A$, —$OC(O)R^A$, —$SO_2R^A$, —$SC(O)R^A$, —$C(S)OR^A$, —$OC(S)R^A$, —$C(S)SR^A$, —$SC(S)R^A$, —$S(O)_{1-2}OR^A$, —$OS(O)_{1-2}R^A$, —$S(O)_{1-2}NR^BR^A$, —$NR^BS(O)_{1-2}R^A$, —$OCO_2R^A$, —$OC(O)NR^BR^A$, —$NR^BCO_2R^A$, —$NR^BC(O)NR^BR^A$, —$SCO_2R^A$, —$OC(O)SR^A$,
—$SC(O)SR^A$, —$SC(O)NR^BR^A$, —$NBC(O)SR^A$, —$OC(S)OR^A$, —$OC(S)NR^BR^A$, —$NR^BC(S)OR^A$, —$NR^BC(S)NR^BR^A$, —$SC(S)OR^A$, —$OC(S)SR^A$, —$SC(S)SR^A$, —$SC(S)NR^BR^A$, —$NR^BC(S)SR^A$, —$NR^BC(NR^B)NR^BR^A$, —$NR^BS(O)_{1-2}NR^BR^A$, phenyl, $C_3$-$C_8$ cycloalkyl, a five to six-membered heteroaryl, or a five to six-membered heterocycloalkyl;
and each $R^7$, is independently optionally-substituted $C_1$-$C_4$ alkyl, —$C_1$, —F, —Br, —CN, —$SF_5$, —$N_3$, nitro, —$SR^A$, —$S(O)_{1-2}R^A$, —$OR^A$, —$(C_0$-$C_3$ alkyl)-$OR^B$, —$NR^BR^A$, —$C(O)R^A$, —$C(O)NR^BR^A$, —$NR^BC(O)$ $R^A$, —$C(S)NR^BR^A$, —$NR^BC(S)R^A$, —$CO_2R^A$, —$OC(O)R^A$, —$SO_3H$, —$C(O)SR^A$, —$SC(O)R^A$, —$C(S)OR^A$, —$OC(S)R^A$, —$C(S)SR^A$, —$SC(S)R^A$, —$S(O)_{1-20}R^A$, —$OS(O)_{1-2}R^A$, —$S(O)_{1-2}NR^BR^A$, —$NR\ BS(O)_{1-2}R^A$, —$OCO_2R^A$, —$OC(O)NR^BR^A$, —$NR^BCO_2R^A$, —$NR^BC(O)NR^BR^A$, —$SCO_2R^A$, —$OC(O)SR^A$, —$SC(O)SR^A$, —$SC(O)NR^BR^A$, —$NR^BC(O)SR^A$, —$OC(S)OR^A$, —$OC(S)NR^BR^A$, —$NR^BC(S)OR^A$, —$NR^BC(S)NR^BR^A$, —$SC(S)OR^A$, —$OC(S)SR^A$, —$SC(S)SR^A$, —$SC(S)NR^BR^A$, —$NR^BC(S)SR^A$, —$NR^BC(NR^B)NR^BR^A$, —$NR^BS(O)_{1-2}NR^BR^A$; phenyl, $C_3$-$C_8$ cycloalkyl, a five to six-membered heteroaryl, or a five to six-membered heterocycloalkyl;

wherein each $R^A$ is independently H or $C_1$-$C_3$ alkyl, and each $R^B$ is independently H, $C_1$-$C_3$ alkyl, $C_1$-$C_3$ fluoroalkyl, $C_1$-$C_3$ hydroxyalkyl, —$S(O)_{1-2}(C_1$-$C_3$ alkyl), —$C(O)(C_1$-$C_3$ alkyl) or —$CO_2(C_1$-$C_3$ alkyl), or $R^A$ and $R^B$ together with the nitrogen atom to which they are attached come together to form an unsubstituted heterocycloalkyl ring of 3-6 ring members.

2. The compound according to claim 1, wherein $R^1$ is hydrogen, halo, $C_1$-$C_8$ alkyl, $C_2$-$C_8$ alkenyl, —$C_{02}H$, —$(C_0$-$C_4$ alkyl)-C(O)O($C_1$-$C_6$ alkyl), —$(C_0$-$C_4$ alkyl)-N($R^{1b}$)—C(O)—O—$(C_1$-$C_6$ alkyl), —$(C_0$-$C_4$ alkyl)-O—C(O)—$NR^{1b}R^{1c}$, —$(C_0$-$C_4$ alkyl)-N($R^{1b}$)—C(O)—$NR^{1b}R^{1c}$, —$OR^{1a}$, —$(C_1$-$C_4$ alkyl)$OR^{1a}$, —$SR^{1a}$, —$(C_1$-$C_4$ alkyl) $SR^{1a}$, —$NR^{1b}R^{1c}$, —$(C_1$-$C_4$ alkyl)$NR^{1b}R^{1c}$, —$(C_1$-$C_4$ alkyl)C(O)$NR^{1b}R^{1c}$, —$(C_0$-$C_4$ alkyl)-aryl, —$(C_0$-$C_4$ alkyl)-heteroaryl, —$(C_0$-$C_4$ alkyl)-cycloalkyl, or —$(C_0$-$C_4$ alkyl)-heterocycloalkyl.

3. The compound according to claim 1, wherein $R^2$ is hydrogen, halo, $C_1$-$C_8$ alkyl, $C_2$-$C_8$ alkenyl, —$C_{02}H$, —$(C_0$-$C_4$ alkyl)-C(O)O($C_1$-$C_6$ alkyl), —$(C_1$-$C_4$ alkyl)$OR^{2a}$, —$(C_1$-$C_4$ alkyl)$SR^{2a}$, —$NR^{2b}R^{2c}$, —$(C_1$-$C_4$ alkyl)$NR^{2b}R^{2c}$, —$(C_1$-$C_4$ alkyl)C(O)$NR^{2b}R^{2c}$, —$(C_0$-$C_4$ alkyl)-aryl, —$(C_0$-$C_4$ alkyl)-heteroaryl, —$(C_0$-$C_4$ alkyl)-cycloalkyl, or —$(C_0$-$C_4$ alkyl)-heterocycloalkyl.

4. The compound according to claim 1, wherein $R^3$ is hydrogen, $C_1$-$C_{12}$ alkyl, $C_2$-$C_{12}$ alkenyl, $C_2$-$C_{12}$ alkynyl, —$(OCH_2CH_2)_{0-6}OCH_3$, —$(C_0$-$C_4$ alkyl)-aryl, —$(C_0$-$C_4$ alkyl)-heteroaryl, —$(C_0$-$C_4$ alkyl)-cycloalkyl or —$(C_0$-$C_4$ alkyl)-heterocycloalkyl.

5. The compound according to claim 1, wherein the compound is of formula:

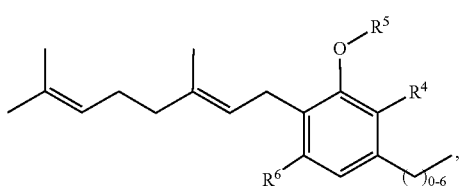

-continued

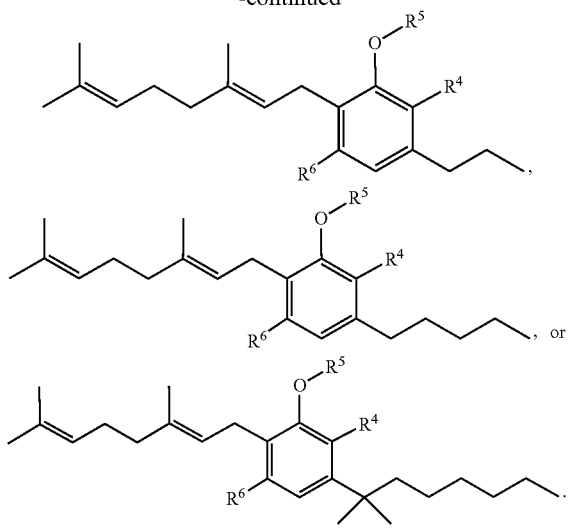

6. The compound according to claim 1, wherein $R^5$ is hydrogen, $C_1$-$C_6$ alkyl, —($C_1$-$C_4$ alkyl)-O—($C_1$-$C_4$ alkyl), —C(O)($C_1$-$C_4$ alkyl), —C(O)O($C_1$-$C_4$ alkyl), —C(O)NH$_2$, —C(O)NH($C_1$-$C_4$ alkyl), or —C(O)N($C_1$-$C_4$ alkyl)$_2$.

7. The compound according to claim 1, wherein $R^6$ is hydrogen or —OR$^{6a}$, wherein $R^{6a}$ is hydrogen, $C_1$-$C_6$ alkyl, —($C_1$-$C_4$ alkyl)-O—($C_1$-$C_4$ alkyl), —C(O)($C_1$-$C_4$ alkyl), —C(O)O($C_1$-$C_4$ alkyl), —C(O)NH$_2$, —C(O)NH($C_1$-$C_4$ alkyl), or NH$_2$, —($C_1$-$C_4$ alkyl)$_2$.

8. The compound according to claim 1, wherein $R^{4a}$ is $C_1$-$C_8$ alkyl, $C_2$-$C_8$ alkenyl, —OR$^{4a}$, —($C_1$-$C_4$ alkyl)OR$^{4e}$, —($C_1$-$C_4$ alkyl)-C(O)($C_1$-$C_4$ alkyl), —($C_0$-$C_4$ alkyl)-aryl, —($C_0$-$C_4$ alkyl)-heteroaryl, —($C_0$-$C_4$ alkyl)-cycloalkyl, —($C_0$-$C_4$ alkyl)-heterocycloalkyl, —NR$^{4d}$R$^{4e}$ or —($C_1$-$C_4$ alkyl)NR$^{4d}$R$^{4e}$.

9. The compound according to claim 1, wherein each alkyl is unsubstituted.

10. The compound according to claim 1, wherein each $R^7$ is independently oxo, $C_1$-$C_4$ alkyl, —Cl, —F, —Br, —CN, —SF$_5$, —N$_3$, nitro, —SR$^A$, —S(O)$_{1-2}$R$^A$, —OR$^A$, —NR$^B$R$^A$, —C(O)R$^A$, —C(O)NR$^B$R$^A$, —NR$^B$C(O)R$^A$, —C(S) NR$^B$ R$^A$, —NR$^B$C(S)R$^A$, —CO$_2$R$^A$, —OC(O)R$^A$, —C(O) SR$^A$, —SC(O)R$^A$, —C(S)OR$^A$, —OC(S)R$^A$, —C(S)SR$^A$, —SC(S)R$^A$, —S(O)$_{1-2}$OR$^A$, —OS(O)$_{1-2}$R$^A$, —S(O)$_{1-2}$NR$^B$R$^A$, or —NR$^B$S(O)$_{1-2}$R$^A$.

11. The compound according to claim 1, which is:
3-(3,7-dimethylocta-2,6-dien-1-yl)-2,4-dihydroxy-6-pentylbenzenesulfonic acid;
sodium 3-(3,7-dimethylocta-2,6-dien-1-yl)-2,4-dihydroxy-6-pentylbenzenesulfonate;
2-(3,7-dimethylocta-2,6-dien-1-yl)-4-(methylsulfonyl)-5-pentylbenzene-1,3-diol;
4-(cyclopropylsulfonyl)-2-(3,7-dimethylocta-2,6-dien-1-yl)-5-pentylbenzene-1,3-diol;
4-(tert-butylsulfonyl)-2-(3,7-dimethylocta-2,6-dien-1-yl)-5-pentylbenzene-1,3-diol;
4-(benzylsulfonyl)-2-(3,7-dimethylocta-2,6-dien-1-yl)-5-pentylbenzene-1,3-diol;
2-(3,7-dimethylocta-2,6-dien-1-yl)-5-pentyl-4-(phenylsulfonyl)benzene-1,3-diol;
2-(3,7-dimethylocta-2,6-dien-1-yl)-4-((4-nitrophenyl)sulfonyl)-5-pentylbenzene-1,3-diol;
2-(3,7-dimethylocta-2,6-dien-1-yl)-5-pentyl-4-(pyridin-3-ylsulfonyl)benzene-1,3-diol;
2-(3,7-dimethylocta-2,6-dien-1-yl)-4-(furan-3-ylsulfonyl)-5-pentylbenzene-1,3-diol;
4-((1H-imidazol-4-yl)sulfonyl)-2-(3,7-dimethylocta-2,6-dien-1-yl)-5-pentylbenzene-1,3-diol;
2-(3,7-dimethylocta-2,6-dien-1-yl)-4-(oxetan-3-ylsulfonyl)-5-pentylbenzene-1,3-diol;
2-(3,7-dimethylocta-2,6-dien-1-yl)-5-pentyl-4-((perfluorophenyl)sulfonyl)benzene-1,3-diol;
4-((3-(3,7-dimethylocta-2,6-dien-1-yl)-2,4-dihydroxy-6-pentylphenyl)sulfonyl)cyclohexa n-1-one;
1-(2-((3-(3,7-dimethylocta-2,6-dien-1-yl)-2,4-dihydroxy-6-pentylphenyl)sulfonyl)ethyl)pyrrolidine-2,5-dione;
4-((2-(dimethylamino)ethyl)sulfonyl)-2-(3,7-dimethylocta-2,6-dien-1-yl)-5-pentylbenzene-1,3-diol;
1-(3-((3-(3,7-dimethylocta-2,6-dien-1-yl)-2,4-dihydroxy-6-pentylphenyl)sulfonyl)piperidin-1-yl)ethan-1-one;
4-((2-chloropyrimidin-5-yl)sulfonyl)-2-(3,7-dimethylocta-2,6-dien-1-yl)-5-pentylbenzene-1,3-diol;
3-(3,7-dimethylocta-2,6-dien-1-yl)-2,4-dihydroxy-6-pentylbenzenesulfonamide;
3-(3,7-dimethylocta-2,6-dien-1-yl)-2,4-dihydroxy-N-methyl-6-pentylbenzenesulfonamide;
3-(3,7-dimethylocta-2,6-dien-1-yl)-2,4-dihydroxy-N,N-dimethyl-6-pentylbenzenesulfonamide;
N-cyclopropyl-3-(3,7-dimethylocta-2,6-dien-1-yl)-2,4-dihydroxy-6-pentylbenzenesulfonamide;
3-(3,7-dimethylocta-2,6-dien-1-yl)-2,4-dihydroxy-N-isopropyl-6-pentylbenzenesulfonamide;
3-(3,7-dimethylocta-2,6-dien-1-yl)-2,4-dihydroxy-6-pentyl-N-phenylbenzenesulfonamide;
N-benzyl-3-(3,7-dimethylocta-2,6-dien-1-yl)-2,4-dihydroxy-6-pentylbenzenesulfonamide;
2-(3,7-dimethylocta-2,6-dien-1-yl)-4-((4-methylpiperazin-1-yl)sulfonyl)-5-pentylbenzene-1,3-diol;
2-(3,7-dimethylocta-2,6-dien-1-yl)-5-pentyl-4-(piperidin-1-ylsulfonyl)benzene-1,3-diol;
2-(3,7-dimethylocta-2,6-dien-1-yl)-4-(morpholinosulfonyl)-5-pentylbenzene-1,3-diol;
3-(3,7-dimethylocta-2,6-dien-1-yl)-2,4-dihydroxy-6-pentyl-N-(pyridin-3-yl)benzenesulfonamide;
3-(3,7-dimethylocta-2,6-dien-1-yl)-2,4-dihydroxy-6-pentyl-N-(pyrimidin-2-yl)benzenesulfonamide;
3-(3,7-dimethylocta-2,6-dien-1-yl)-2,4-dihydroxy-N-(2-oxopropyl)-6-pentylbenzenesulfonamide;
1-((3-(3,7-dimethylocta-2,6-dien-1-yl)-2,4-dihydroxy-6-pentylphenyl)sulfonyl)azetidin-3-one;
3-(3,7-dimethylocta-2,6-dien-1-yl)-2,4-dihydroxy-N-(oxetan-2-ylmethyl)-6-pentylbenzenesulfonamide;
4-((2-azaspiro[3.3]heptan-2-yl)sulfonyl)-2-(3,7-dimethylocta-2,6-dien-1-yl)-5-pentylbenzene-1,3-diol;
4-((2,6-diazaspiro[3.3]heptan-2-yl)sulfonyl)-2-(3,7-dimethylocta-2,6-dien-1-yl)-5-pentylbenzene-1,3-diol;
((3-(3,7-dimethylocta-2,6-dien-1-yl)-2,4-dihydroxy-6-pentylphenyl)sulfonyl)alanine;
methyl ((3-(3,7-dimethylocta-2,6-dien-1-yl)-2,4-dihydroxy-6-pentylphenyl)sulfonyl)alaninate;
N-((3-(3,7-dimethylocta-2,6-dien-1-yl)-2,4-dihydroxy-6-pentylphenyl)sulfonyl)-3-morpholinopropanamide;
4-((3-(3,7-dimethylocta-2,6-dien-1-yl)-2,4-dihydroxy-6-pentylphenyl)sulfonamido)-4-oxobutanoic acid;
N-((3-(3,7-dimethylocta-2,6-dien-1-yl)-2,4-dihydroxy-6-pentylphenyl)sulfonyl)-3-(4-methylpiperazin-1-yl)propanamide;
2-amino-N-((3-(3,7-dimethylocta-2,6-dien-1-yl)-2,4-dihydroxy-6-pentylphenyl)sulfonyl) acetamide;

N-((3-(3,7-dimethylocta-2,6-dien-1-yl)-2,4-dihydroxy-6-pentylphenyl)sulfonyl)-2-(2-methoxyethoxy)acetamide;

2-amino-N-((3-(3,7-dimethylocta-2,6-dien-1-yl)-2,4-dihydroxy-6-pentylphenyl)sulfonyl)-3-hydroxypropanamide;

2-amino-N-((3-(3,7-dimethylocta-2,6-dien-1-yl)-2,4-dihydroxy-6-pentylphenyl)sulfonyl)propanamide;

3-amino-N-((3-(3,7-dimethylocta-2,6-dien-1-yl)-2,4-dihydroxy-6-pentylphenyl)sulfonyl)-2-methylpropanamide;

N-((3-(3,7-dimethylocta-2,6-dien-1-yl)-2,4-dihydroxy-6-pentylphenyl)sulfonyl)acetamide;

N-((3-(3,7-dimethylocta-2,6-dien-1-yl)-2,4-dihydroxy-6-pentylphenyl)sulfonyl)-3-oxobutanamide;

N-((3-(3,7-dimethylocta-2,6-dien-1-yl)-2,4-dihydroxy-6-pentylphenyl)sulfonyl)-2-(3-methyl-1H-1,2,4-triazol-5-yl)acetamide;

N-((3-(3,7-dimethylocta-2,6-dien-1-yl)-2,4-dihydroxy-6-pentylphenyl)sulfonyl)-1H-1,2,4-triazole-5-carboxamide;

N-((3-(3,7-dimethylocta-2,6-dien-1-yl)-2,4-dihydroxy-6-pentylphenyl)sulfonyl)oxetane-2-carboxamide;

N-((3-(3,7-dimethylocta-2,6-dien-1-yl)-2,4-dihydroxy-6-pentylphenyl)sulfonyl)benzamide;

N-((3-(3,7-dimethylocta-2,6-dien-1-yl)-2,4-dihydroxy-6-pentylphenyl)sulfonyl)nicotinamide;

N-((3-(3,7-dimethylocta-2,6-dien-1-yl)-2,4-dihydroxy-6-pentylphenyl)sulfonyl)-2-phenylacetamide;

N-((3-(3,7-dimethylocta-2,6-dien-1-yl)-2,4-dihydroxy-6-pentylphenyl)sulfonyl)-2-(furan-2-yl)acetamide;

N-((3-(3,7-dimethylocta-2,6-dien-1-yl)-2,4-dihydroxy-6-pentylphenyl)sulfonyl)-2-(oxazol-2-yl)acetamide;

N-((3-(3,7-dimethylocta-2,6-dien-1-yl)-2,4-dihydroxy-6-pentylphenyl)sulfonyl)-2-(thiazol-2-yl)acetamide;

2-(1H-benzo[d]imidazol-2-yl)-N-((3-(3,7-dimethylocta-2,6-dien-1-yl)-2,4-dihydroxy-6-pentylphenyl)sulfonyl)acetamide;

3-(3,7-dimethylocta-2,6-dien-1-yl)-2,4-dihydroxy-6-pentyl-N-(phenylsulfonyl)benzamide;

N-(cyclohexylsulfonyl)-3-(3,7-dimethylocta-2,6-dien-1-yl)-2,4-dihydroxy-6-pentylbenzamide;

3-(3,7-dimethylocta-2,6-dien-1-yl)-2,4-dihydroxy-6-pentyl-N-((prop-1-en-1-yl)sulfonyl)benzamide;

N-((1H-benzo[d]imidazol-2-yl)sulfonyl)-3-(3,7-dimethylocta-2,6-dien-1-yl)-2,4-dihydroxy-6-pentylbenzamide;

N-cyclohexyl-3-(3,7-dimethylocta-2,6-dien-1-yl)-2,4-dihydroxy-6-pentylbenzenesulfonamide;

N-cyclobutyl-3-(3,7-dimethylocta-2,6-dien-1-yl)-2,4-dihydroxy-6-pentylbenzenesulfonamide;

3-(3,7-dimethylocta-2,6-dien-1-yl)-N-hexyl-2,4-dihydroxy-6-pentylbenzenesulfonamide;

N-allyl-3-(3,7-dimethylocta-2,6-dien-1-yl)-2,4-dihydroxy-6-pentylbenzenesulfonamide;

3-(3,7-dimethylocta-2,6-dien-1-yl)-2,4-dihydroxy-6-pentyl-N-(pyridin-3-ylsulfonyl)benzamide; or phenyl-3-(3,7-dimethylocta-2,6-dien-1-yl)-2,4-dihydroxy-6-pentylbenzenesulfonate.

12. A pharmaceutical composition comprising a compound according to claim 1, or an enantiomer, diastereomer, racemate, or tautomer thereof, or a pharmaceutically acceptable salt, solvate or hydrate of the compound, enantiomer, diastereomer, racemate, or tautomer, together with a pharmaceutically acceptable excipient, diluent, or carrier.

13. A method of treating a disease associated with a cannabinoid receptor in a subject in need thereof, the method comprising administering to the subject a therapeutically effective amount of a compound according to claim 1 or a pharmaceutical composition thereof.

14. The method according to claim 13, wherein the cannabinoid receptor is one or more of CB1, CB2, 5HT1A, 5HT2A, GPR18, GPR55, GPR119, TRPV1, TPRV2, PPARγ or a μ-opioid receptor.

15. The method according to claim 13, wherein the cannabinoid receptor is CB1 or CB2.

16. A method of treating a subject in need thereof, the method comprising administering to the subject a therapeutically effective amount of a compound according to claim 1 or a pharmaceutical composition thereof, wherein the treatment is of acute pain, attention deficit hyperactivity disorder, attention deficit disorder, alcohol use disorder, allergic asthma, Amyotrophic lateral sclerosis, Alzheimer's disease, anorexia, anxiety disorders, arthritis, atherosclerosis, autism, bipolar disorder, burns, cancer, cancer pain, Charcot-Marie-Tooth disease, chronic inflammatory demyelinating polyneuropathies, chronic pain, chronic allograft nephropathy, cocaine use disorder, complex regional pain syndrome, congestive heart failure, depression, fibromyalgia, fragile X syndrome, fragile X-associated tremor/ataxia syndrome, frontotemporal dementias, gingivitis pyrexia, glaucoma, glioblastoma, glomerulonephropathy, Huntington's disease, hypertrophic scars, inflammatory bowel disorder, irritable bowel syndrome, inflammation, Inflammatory myopathies, ischemia, kidney fibrosis, keloids, leukodystrophies, liver fibrosis, liver cirrhosis, lung fibrosis, migraine, multiple sclerosis, myocardial infarction, nausea, neuropathic pain, nightmare disorder, non-alcoholic fatty liver disease, obesity, obsessive-compulsive disorder, opioid use disorder, osteoarthritis, osteoporosis, Parkinson's disease, post-concussion syndrome/traumatic brain injury, psychosis/schizophrenia, post traumatic stress syndrome, random eye movement sleep behaviour disorder, reperfusion injury, Rett syndrome, rheumatoid arthritis, skin conditions, sleep disorders, spinocerebellar ataxias, systemic fibrosis, systemic sclerosis, thermal injury, tobacco use disorder/nicotine dependence, Tourette's, tumors, or trigeminal neuralgia.

17. A method of opioid sparing or regulation of bone mass in a subject in need thereof, the method comprising administering to the subject a therapeutically effective amount of a compound according to claim 1 or a pharmaceutical composition thereof.

* * * * *